(12) United States Patent
Sundermann et al.

(10) Patent No.: US 8,048,879 B2
(45) Date of Patent: Nov. 1, 2011

(54) SUBSTITUTED 4,5,6,7-TETRAHYDRO-ISOXAZOLO[4,5-C]PYRIDINE COMPOUNDS AND USE THEREOF FOR PRODUCING MEDICAMENTS

(75) Inventors: Corinna Sundermann, Aachen (DE); Bernd Sundermann, Aachen (DE); Jörg Holenz, Enhörna (SE); HagenHeinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 648 days.

(21) Appl. No.: 11/887,969

(22) PCT Filed: Apr. 5, 2006

(86) PCT No.: PCT/EP2006/003084
§ 371 (c)(1),
(2), (4) Date: Nov. 21, 2008

(87) PCT Pub. No.: WO2006/105945
PCT Pub. Date: Oct. 12, 2006

(65) Prior Publication Data
US 2009/0076001 A1    Mar. 19, 2009

(30) Foreign Application Priority Data

Apr. 7, 2005 (DE) .......................... 10 2005 016 170

(51) Int. Cl.
*A61K 31/5377* (2006.01)
*A61K 31/437* (2006.01)
*A61K 31/496* (2006.01)
*C07D 498/04* (2006.01)

(52) U.S. Cl. ................ 514/234.2; 514/302; 514/253.04; 546/115; 544/127; 544/362

(58) Field of Classification Search ............... 514/234.2, 514/302, 253.04; 544/127, 362; 546/115
See application file for complete search history.

(56) References Cited

U.S. PATENT DOCUMENTS

| 4,309,433 A | * | 1/1982 | Hirai et al. | .................. 514/343 |
| 4,482,566 A | | 11/1984 | Hirai et al. | |
| 4,564,623 A | | 1/1986 | Hirai et al. | |
| 2004/0192916 A1 | | 9/2004 | Buschmann et al. | |

FOREIGN PATENT DOCUMENTS

| EP | 0 023 578 A1 | 2/1981 |
| WO | WO 2004/018428 A1 | 3/2004 |
| WO | WO 2005/110971 A1 | 11/2005 |

OTHER PUBLICATIONS

Nitu, A N et al., "Emerging trends in the pharmacotherapy of chronic pain", Expert Opinion on Investigating Drugs, 2003, pp. 545-559, vol. 12, No. 4, Ashley Publications Ltd., London, Great Britain, XP-002335568.
International Search Report dated Jul. 28, 2006 including English translation of the pertinent portion (Thirteen (13) pages).
German Search Report dated Feb. 9, 2006 including English translation of the pertinent portion (Nine (9) pages).
English translation of the International Preliminary Report on Patentability (Seven (7) pages), (Mar. 13, 2008).

* cited by examiner

*Primary Examiner* — D M Seaman
*Assistant Examiner* — Niloofar Rahmani
(74) *Attorney, Agent, or Firm* — Crowell & Moring LLP

(57) ABSTRACT

The present invention relates to substituted 4,5,6,7-tetrahydro-isoxazolo[4,5-c]pyridine compound corresponding to formula I, methods for producing them, to medicaments containing these compounds, the use of these compounds for producing medicaments and related treatment methods

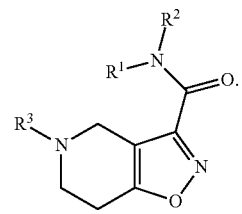

I

24 Claims, No Drawings

SUBSTITUTED 4,5,6,7-TETRAHYDRO-ISOXAZOLO[4,5-C]PYRIDINE COMPOUNDS AND USE THEREOF FOR PRODUCING MEDICAMENTS

The present invention relates to substituted 4,5,6,7-tetrahydro-isoxazolo[4,5-c]pyridine compounds, to a method for producing them, to medicaments containing these compounds and to the use of these compounds for producing medicaments.

The treatment of pain, in particular neuropathic pain, is of great medical significance. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

Conventional opioids, such as for example morphine, are effective in the treatment of severe to very severe pain, but they often lead to unwanted accompanying symptoms, such as for example respiratory depression, vomiting, sedation, constipation or the development of tolerance. Moreover, they are frequently insufficiently effective in the case of neuropathic pain, suffered in particular by tumour patients.

One object of the present invention was accordingly to provide novel compounds which are suitable in particular as pharmaceutical active ingredients in medicaments, preferably in medicaments for the prevention and/or treatment of pain, in particular acute pain, chronic pain and/or neuropathic pain.

It has now surprisingly been found that substituted 4,5,6,7-tetrahydro-isoxazolo[4,5-c]pyridine compounds of the general formula I stated hereinafter are suitable for noradrenalin receptor regulation, in particular for inhibiting noradrenalin reuptake (NA uptake), for 5-HT receptor regulation, in particular for inhibiting 5-hydroxy tryptophan reuptake (5-HT uptake) and/or for batrachotoxin (BTX) receptor regulation and may therefore be used in particular as pharmaceutical active ingredients in medicaments for the prevention and/or treatment disorders or diseases associated with these receptors or processes.

The present invention accordingly provides substituted 4,5,6,7-tetrahydro-isoxazolo[4,5-c]pyridine compounds of the general formula I,

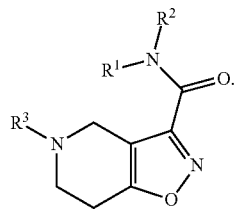

I in which
$R^1$ denotes —(CHR$^4$)—(CH$_2$)$_c$—(CH$_2$)$_d$—C(=O)—OR$^5$
with c=0 or 1 and d=0 or 1;
—(CHR$^6$)—(CHR$^7$)$_e$—V$_f$—(CH$_2$)$_g$—W$_h$—(CH$_2$)$_i$—R$^8$
with e=0 or 1, f=0 or 1, g=0 or 1, h=0 or 1 and i=0 or 1,
in which V and W mutually independently in each case denote O, S, NH, N(CH$_3$) or N(C$_2$H$_5$);

a linear or branched, saturated or unsaturated, optionally substituted C$_{1-10}$ aliphatic residue;
an unsaturated or saturated, optionally substituted 3-, 4-, 5-, 6-, 7-, 8- or 9-membered cycloaliphatic residue, which may be fused with a saturated or unsaturated, optionally aromatic, optionally substituted mono- or polycyclic ring system and/or be bridged with a linear or branched, optionally substituted C$_{1-5}$ alkylene group,
or an optionally substituted 5- to 14-membered aryl or heteroaryl residue, which may be fused with a saturated or unsaturated, optionally substituted mono- or polycyclic ring system;
$R^2$ denotes a hydrogen residue;
—(CH$_2$)—R$^9$
or a linear or branched, saturated or unsaturated, optionally substituted C$_{1-10}$ aliphatic residue;
or
$R^1$ and $R^2$, together with the nitrogen atom joining them together as a ring member, form a saturated or unsaturated, optionally substituted 4-, 5-, 6-, 7-, 8- or 9-membered heterocycloaliphatic residue,
wherein the heterocycloaliphatic residue may in each case be substituted with 1, 2, 3, 4 or 5 substituents mutually independently selected from the group consisting of R$^{10}$, —C(=O)—R$^{11}$ and —(CH$_2$)—NH—C(=O)—R$^{12}$ and/or may in each case comprise a further 1, 2, 3, 4 or 5 heteroatom(s) mutually independently selected from the group consisting of oxygen, nitrogen and sulfur as ring member(s);
$R^3$ denotes —C(=O)—NR$^{13}$R$^{14}$;
—C(=O)—R$^{15}$;
—C(=O)—(CH$_2$)$_j$X$_k$—(CH$_2$)$_m$—(CH$_2$)$_n$—C(=O)—OR$^{16}$ with j=0 or 1, k=0 or 1, m=0 or 1 and n=0 or 1, in which X denotes O, S, NH, N(CH$_3$), N(C$_2$H$_5$) or CR$^{17}$R$^{18}$;
—C(=O)—(CHR$^{19}$)—NH—C(=O)—OR$^{20}$;
—C(=O)—(CH$_2$)—(CH$_2$)$_p$—(CH$_2$)$_q$—Y$_r$—(CH$_2$)$_s$—R$^{21}$ with p=0 or 1, q=0 or 1, r 0 or 1 and s=0 or 1, in which Y denotes O, S, NH, N(CH$_3$) or N(C$_2$H$_5$);
—C(=O)—(CH=CH)—R$^{22}$;
—S(=O)$_2$—R$^{23}$;
—S(=O)$_2$—NR$^{24}$R$^{25}$;
—C(=S)—NR$^{26}$—(CH$_2$)$_t$—(CH$_2$)$_u$—Z$_v$—R$^{27}$ with t=0 or 1, u=0 or 1 and v=0 or 1, in which Z denotes O, S, NH, N(CH$_3$) or N(C$_2$H$_5$);
—C(=S)—NR$^{26}$—(CHR$^{28}$)—R$^{29}$;
—C(=S)—NR$^{26}$—C(=O)—R$^{30}$;
or —(CH$_2$)—R$^{31}$;
$R^4$ denotes —C(=O)—NH$_2$;
a hydrogen residue
or a linear or branched, saturated or unsaturated, optionally substituted C$_{1-10}$ aliphatic residue;
$R^5$, $R^{17}$, $R^{18}$, $R^{24}$ and $R^{25}$, mutually independently, in each case denote
a linear or branched, saturated or unsaturated, optionally substituted C$_{1-10}$ aliphatic residue,
$R^6$, $R^7$, $R^{13}$, $R^{16}$ and $R^{26}$, mutually independently, in each case denote
a hydrogen residue
or a linear or branched, saturated or unsaturated, optionally substituted C$_{1-10}$ aliphatic residue;
$R^8$, $R^9$, $R^{21}$, $R^{22}$, $R^{23}$, $R^{30}$ and $R^{31}$, mutually independently, in each case denote
an unsaturated or saturated, optionally substituted 3-, 4-, 5-, 6-, 7-, 8- or 9-membered cycloaliphatic residue, which may be fused with a saturated or unsaturated, optionally aromatic, optionally substituted mono- or polycyclic ring system, or an optionally substituted 5- to 14-membered aryl or heteroaryl residue, which may be fused with a saturated or unsaturated, optionally substituted mono- or polycyclic ring system;

$R^{10}$, $R^{11}$, $R^{12}$, $R^{14}$ and $R^{20}$, mutually independently, in each case denote a linear or branched, saturated or unsaturated, optionally substituted $C_{1-10}$ aliphatic residue, an unsaturated or saturated, optionally substituted 3-, 4-, 5-, 6-, 7-, 8- or 9-membered cycloaliphatic residue, which may be fused with a saturated or unsaturated, optionally aromatic, optionally substituted mono- or polycyclic ring system and/or be attached via a linear or branched, optionally substituted $C_{1-5}$ alkylene, $C_{2-5}$ alkenylene or $C_{2-5}$ alkynylene group, or an optionally substituted 5- to 14-membered aryl or heteroaryl residue, which may be attached via a linear or branched, optionally substituted $C_{1-5}$ alkylene, $C_{2-5}$ alkenylene or $C_{2-5}$ alkynylene group;

$R^{15}$ and $R^{27}$, mutually independently, in each case denote a linear or branched, saturated or unsaturated, optionally substituted $C_{1-10}$ aliphatic residue, an unsaturated or saturated, optionally substituted 3-, 4-, 5-, 6-, 7-, 8- or 9-membered cycloaliphatic residue, which may be bridged with a linear or branched, optionally substituted $C_{1-5}$ alkylene group, or an optionally substituted 5- to 14-membered aryl or heteroaryl residue, which may be fused with a saturated or unsaturated, optionally substituted mono- or polycyclic ring system;

$R^{19}$ denotes an optionally substituted 5- to 14-membered aryl or heteroaryl residue, which may be attached via a linear or branched, optionally substituted $C_{1-5}$ alkylene, $C_{2-5}$ alkenylene or $C_{2-5}$ alkynylene group optionally comprising 1 or 2 heteroatom(s) as chain link(s);

$R^{28}$ and $R^{29}$, mutually independently, in each case denote a linear or branched, saturated or unsaturated, optionally substituted $C_{1-10}$ aliphatic residue or an optionally substituted 5- to 14-membered aryl or heteroaryl residue, which may be fused with a saturated or unsaturated, optionally substituted mono- or polycyclic ring system;

wherein the above-stated $C_{1-10}$ aliphatic residues may in each case be substituted with 1, 2, 3, 4 or 5 substituents mutually independently selected from the group consisting of F, Cl, Br, I, —CN, —NO$_2$, —OH, —O—$C_{1-5}$ alkyl, —SH, —S—$C_{1-5}$ alkyl, —NH$_2$, —NH—$C_{1-5}$ alkyl and —N($C_{1-5}$ alkyl)($C_{1-5}$ alkyl);

the above-stated cycloaliphatic residues may in each case be substituted with 1, 2, 3, 4 or 5 substituents mutually independently selected from the group consisting of oxo (═O), thioxo (═S), F, Cl, Br, I, —CN, —CF$_3$, —SF$_5$, —OH, —O—$C_{1-5}$ alkyl, —NH$_2$, —NO$_2$, —O—CF$_3$, —S—CF$_3$, —SH, —S—$C_{1-5}$ alkyl, —$C_{1-5}$ alkyl, —C(═O)—H, —C(═O)—$C_{1-5}$ alkyl, —C(═O)—OH, —C(═O)—O—$C_{1-5}$ alkyl, —(CH$_2$)—C(═O)—OH, —(CH$_2$)—C(═O)—O—$C_{1-5}$ alkyl, —NH—$C_{1-5}$ alkyl, —N($C_{1-5}$ alkyl)$_2$, —(CH$_2$)-benzo[b]furanyl, —O-phenyl, —O-benzyl, phenyl, benzyl, naphthyl and —(CH$_2$)-naphthyl, wherein in each case the cyclic moiety of the residues —O-phenyl, —O-benzyl, phenyl, —(CH$_2$)-benzo[b]furanyl, benzyl, naphthyl and —(CH$_2$)-naphthyl may be substituted with 1, 2, 3, 4 or 5 substituents mutually independently selected from the group consisting of F, Cl, Br, —OH, —CF$_3$, —SF$_5$, —CN, —NO$_2$, —O—$C_{1-5}$ alkyl, —$C_{1-5}$ alkyl, —O—CF$_3$, —S—CF$_3$, phenyl and —O-benzyl, and the above-stated cycloaliphatic residues may in each case optionally comprise 1, 2, 3, 4 or 5 heteroatom(s) mutually independently selected from the group consisting of oxygen, nitrogen and sulfur as ring member(s);

the above-stated $C_{1-5}$ alkylene, $C_{2-5}$ alkenylene or $C_{2-5}$ alkynylene groups may in each case be substituted with 1, 2, 3, 4 or 5 substituents mutually independently selected from the group consisting of F, Cl, Br, —OH, —SH, —NH$_2$, —CN, NO$_2$ and phenyl, and the above-stated $C_{1-5}$ alkylene, $C_{2-5}$ alkenylene or $C_{2-5}$ alkynylene groups may optionally in each case comprise 1 or 2 heteroatom(s) selected from the group consisting of oxygen, nitrogen and sulfur as chain link(s);

the rings of the above-stated mono- or polycyclic ring systems may optionally in each case be substituted with 1, 2, 3, 4 or 5 substituents mutually independently selected from the group consisting of oxo (═O), thioxo (═S), F, Cl, Br, I, —CN, —CF$_3$, —SF$_5$, —OH, —O—$C_{1-5}$ alkyl, —O—$C_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—$C_{1-5}$ alkyl, —$C_{1-5}$ alkyl, —C(═O)—OH, —C(═O)—O—$C_{1-5}$ alkyl, —NH—$C_{1-5}$ alkyl, —N($C_{1-5}$ alkyl)$_2$, —NH—C(═O)—O—$C_{1-5}$ alkyl, —NH—C(═O)—$C_{1-5}$ alkyl, —C(═O)—H, —C(═O)—$C_{1-5}$ alkyl, —C(═O)—NH$_2$, —C(═O)—NH—$C_{1-5}$ alkyl, —C(═O)—N—($C_{1-5}$ alkyl)$_2$, —S(═O)$_2$—NH$_2$, —S(═O)$_2$—NH—$C_{1-5}$ alkyl, —(CH$_2$)-benzo[b]furanyl, —O-phenyl, —O-benzyl, phenyl and benzyl, wherein in each case the cyclic moiety of the residues —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—$C_{1-5}$ alkyl, —$C_{1-5}$ alkyl, —O—CF$_3$, —S—CF$_3$, phenyl and —O-benzyl, and the rings of the above-stated mono- or polycyclic ring systems are in each case 5-, 6- or 7-membered and may in each case comprise 1, 2, 3, 4 or 5 heteroatom(s) as ring member(s) which are mutually independently selected from the group consisting of oxygen, nitrogen and sulfur;

and the above-stated aryl or heteroaryl residues may in each case be substituted with 1, 2, 3, 4 or 5 substituents mutually independently selected from the group consisting of F, Cl, Br, I, —CN, —CF$_3$, —SF$_5$, —OH, —O—$C_{1-5}$ alkyl, —O—$C_{2-5}$-alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—$C_{1-5}$ alkyl, —$C_{1-5}$ alkyl, —C(═O)—O—$C_{1-5}$ alkyl, —NH—$C_{1-5}$ alkyl, —N($C_{1-5}$ alkyl)$_2$, —NH—C(═O)—O—$C_{1-5}$ alkyl, —NH—C(═O)—$C_{1-5}$ alkyl, —C(═O)—H, —C(═O)—$C_{1-5}$ alkyl, —C(═O)—NH$_2$, —C(═O)—NH—$C_{1-5}$ alkyl, —C(═O)—N—($C_{1-5}$ alkyl)$_2$, —S(═O)$_2$—NH$_2$, —S(═O)$_2$—NH—$C_{1-5}$ alkyl, —(CH$_2$)-benzo[b]furanyl, —O-phenyl, —O-benzyl, phenyl and benzyl, wherein in each case the cyclic moiety of the residues —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—$C_{1-5}$ alkyl, —$C_{1-5}$ alkyl, —O—CF$_3$, —S—CF$_3$, phenyl and —O-benzyl, and the above-stated heteroaryl residues may in each case comprise 1, 2, 3, 4 or 5 heteroatom(s) mutually independently selected from the group consisting of oxygen, nitrogen and sulfur as ring member(s);

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

For the purposes of the present invention, a mono- or polycyclic ring system should be understood to mean mono- or polycyclic hydrocarbon residues which may be saturated, unsaturated or aromatic and optionally comprise one or more heteroatoms as ring members. Such a mono- or polycyclic ring system may, for example, be fused (anellated) with a cycloaliphatic residue, an aryl residue or a heteroaryl residue.

If a polycyclic ring system, such as for example a bicyclic ring system, is present, the various rings may in each case mutually independently be of a different degree of saturation, i.e. be saturated, unsaturated or aromatic. A polycyclic ring system is preferably a bicyclic ring system.

A person skilled in the art will understand that some of the substituted 4,5,6,7-tetrahydro-isoxazolo[4,5-c]pyridine compounds of the general formula I according to the invention may be present in the form of rotamers, which the present invention also provides and which may in each case also be present as active ingredients in the medicaments described below.

Examples of suitable aryl residues which may be mentioned are phenyl, 1-naphthyl and 2-naphthyl.

Suitable heteroaryl residues which may be mentioned by way of example are pyridinyl, thiophenyl (thienyl), furanyl (furyl), pyrazolinyl, pyrimidinyl, pyridinyl, 2-pyridinyl, 3-pyridinyl, 4-pyridinyl, 2-pyrimidinyl, 4-pyrimidinyl, 5-pyrimidinyl, pyridazinyl, 3-pyridazinyl, 4-pyridazinyl, pyrazinyl, 3-pyrazinyl, imidazolyl, 2-imidazolyl, 4-imidazolyl, isoxazolyl, 3-isoxazolyl, 4-isoxazolyl, 5-isoxazolyl, pyrazolyl, 3-pyrazolyl, 4-pyrazolyl, 5-pyrazolyl, oxazolyl, 2-oxazolyl, 4-oxazolyl, 5-oxazolyl, 1,2,3-oxathiazolyl, 1,2,3-oxadiazolyl, 1,2,4-oxadiazolyl, 1,2,5-oxadiazolyl, 1,3,4-oxadiazolyl, thiazolyl, 2-thiazolyl, 4-thiazolyl, 5-thiazolyl, 3-isothiazolyl, 4-isothiazolyl, 5-isothiazolyl, 2-thiophenyl, 3-thiophenyl, pyrrolyl, 2-pyrrolyl, 3-pyrrolyl, 3-isopyrrolyl, 4-isopyrrolyl, 5-isopyrrolyl, 1,2,4-oxadiazol-3-yl, 1,2,4-oxadiazol-5-yl, 1,2,4-thiadiazolyl-3-yl, 1,2,4-thiadiazolyl-5-yl, 1,3,4-thiadiazolyl-5-yl, triazolyl, 1,2,4-triazol-3-yl, 1,2,4-triazol-5-yl, 1,2,3,4-tetrazol-5-yl, 1,2,3,4-thiatriazolyl, quinolinyl, triazinyl, quinoxalinyl, pyranyl, indolyl, isoindolyl, benzo[b]furanyl, benzo[b]thiophenyl, indazolyl and isoquinolinyl.

A person skilled in the art is aware that the 4,5,6,7-tetrahydroisoxazolo[4,5-c]pyridine compounds of the general formula I according to the invention may also be designated 6,7-dihydro-4H-isoxazolo[4,5-c]pyridine compounds.

Preferred substituted 4,5,6,7-tetrahydro-isoxazolo[4,5-c]pyridine compounds of the above-stated general formula I are those in which $R^1$ denotes —(CHR$^4$)—(CH$_2$)$_c$—(CH$_2$)$_d$—C(=O)—OR$^5$
with c=0 or 1 and d 0 or 1;
—(CHR$^6$)—(CHR$^7$)$_e$—V$_f$—(CH$_2$)$_g$—W$_h$—(CH$_2$)$_i$R$^8$
with e=0 or 1, f=0 or 1, g=0 or 1, h=0 or 1 and i=0 or 1,
in which V and W in each case mutually independently denote O, S, NH, N(CH$_3$) or N(C$_2$H$_5$);
an alkyl residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl residue may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);
an alkenyl residue selected from the group consisting of vinyl, 1-propenyl, 2-propenyl, 1-butenyl, 2-butenyl and 3-butenyl, wherein the alkenyl residue may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);
an alkynyl residue selected from the group consisting of ethynyl, 1-propynyl, 2-propynyl, 1-butynyl, 2-butynyl and 3-butynyl, wherein the alkynyl residue may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);
a (hetero)cycloaliphatic residue selected from the group consisting of cyclopropyl, cyclobutyl, cyclopentyl, cyclohexyl, cycloheptyl, (6,6)-dimethyl-[3.1.1]-bicycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, wherein the (hetero)cycloaliphatic residue may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—OH, —C(=O)—O—C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —(CH$_2$)-benzo[b]furanyl, —O-phenyl, —O-benzyl, phenyl, benzyl, naphthyl and —(CH$_2$)-naphthyl, wherein in each case the cyclic moiety of the substituents —O-phenyl, —O-benzyl, phenyl, —(CH$_2$)-benzo[b]furanyl, benzyl, naphthyl and —(CH$_2$)-naphthyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;
or a residue selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrimidinyl, indazolyl, quinazolinyl, quinolinyl and isoquinolinyl, wherein the residue may in each case be substituted with 1, 2, 3, 4 or 5 substituents mutually independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—O—C$_{1-5}$ alkyl, —NH—C$_{1-5}$ alkyl, —N(C$_{1-5}$ alkyl)$_2$, —NH—C(=O)—O—C$_{1-5}$ alkyl, —NH—C(=O)—

$C_{1-5}$ alkyl, —C(=O)—H, —C(=O)—$C_{1-5}$ alkyl, —C(=O)—NH$_2$, —C(=O)—NH—$C_{1-5}$ alkyl, —C(=O)—N—($C_{1-5}$ alkyl)$_2$, —S(=O)$_2$—NH$_2$, —S(=O)$_2$—NH—$C_{1-5}$ alkyl, —(CH$_2$)-benzo[b]furanyl, —O-phenyl, —O-benzyl, phenyl and benzyl, wherein in each case the cyclic moiety of the residues —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—$C_{1-5}$ alkyl, —$C_{1-5}$ alkyl, —O—CF$_3$, —S—CF$_3$, phenyl and —O-benzyl;

$R^2$ denotes a hydrogen residue;
—(CH$_2$)—$R^9$ or an alkyl residue selected from the group consisting of methyl, ethyl, n-propyl, isopropyl, n-butyl, sec-butyl, isobutyl, tert-butyl, n-pentyl, sec-pentyl —(CH$_2$)—(CH$_2$)(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl residue may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

or $R^1$ and $R^2$, together with the nitrogen atom joining them together as a ring member, form a heterocycloaliphatic residue selected from the group consisting of imidazolidinyl, (1,3)-thiazolidinyl, piperazinyl, morpholinyl, thiomorpholinyl, pyrrolidinyl; piperidinyl; (1,2,3,6)-tetrahydropyridinyl and (1,2,3,4)-tetrahydropyridinyl, wherein the heterocycloaliphatic residue may in each case be substituted with 1, 2 or 3 substituents mutually independently selected from the group consisting of $R^{10}$, —C(=O)—$R^{11}$ and —(CH$_2$)—NH—C(=O)—$R^{12}$;

$R^3$ denotes —C(=O)—NR$^{13}$R$^{14}$;
—C(=O)—$R^{15}$;
—C(=O)—(CH$_2$)—X—(CH$_2$)—C(=O)—OR$^{16}$ or —C(=O)—X—(CH$_2$)—C(=O)—OR$^{16}$, in which X in each case denotes O, S, NH, N(CH$_3$), N(C$_2$H$_5$) or CR$^{17}$R$^{18}$; or
—C(=O)—(CH$_2$)—(CH$_2$)—(CH$_2$)—C(=O)—OR$^{16}$
—C(=O)—(CHR$^{19}$)—NH—C(=O)—OR$^{20}$;
—C(=O)—(CH$_2$)—$R^{21}$, —C(=O)—(CH$_2$)—$R^{21}$, —C(=O)—(CH$_2$)—Y—(CH$_2$)—$R^{21}$ or —C(=O)—(CH$_2$)—(CH$_2$)—(CH$_2$)—Y—$R^{21}$, in which Y in each case denotes O, S, NH, N(CH$_3$) or N(C$_2$H$_5$);
—C(=O)—(CH=CH)—$R^{22}$;
—S(=O)$_2$—$R^{23}$;
—S(=O)$_2$—NR$^{24}$R$^{25}$;
—C(=S)—NR$^{26}$—$R^{27}$, —C(=S)—NR$^{26}$—(CH$_2$)—$R^{27}$, —C(=S)—NR$^{26}$—(CH$_2$)—(CH$_2$)—$R^{27}$ or —C(=S)—NR$^{26}$—(CH$_2$)—(CH$_2$)—Z—$R^{27}$, in which Z denotes O, S, NH, N(CH$_3$) or N(C$_2$H$_5$);
—C(=S)—NR$^{26}$—(CHR$^{28}$)—$R^{29}$;
—C(=S)—NR$^{26}$—C(=O)—$R^{30}$; or
—(CH$_2$)—$R^{31}$;

$R^4$ denotes —C(=O)—NH$_2$;
a hydrogen residue;
an alkyl residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl residue may in each case be substituted with 1, 2, 3, 4 or 5 substituents mutually independently selected from the group consisting of F, Cl, Br, I, —CN, —NO$_2$, —OH, —O—$C_{1-5}$ alkyl, —SH, —S—$C_{1-5}$ alkyl, —NH$_2$, —NH—$C_{1-5}$ alkyl and —N($C_{1-5}$ alkyl)($C_{1-5}$ alkyl);

or an alkenyl residue selected from the group consisting of vinyl, 1-propenyl, 2-propenyl, 1-butenyl, 2-butenyl and 3-butenyl, wherein the alkenyl residue may in each case be substituted with 1, 2, 3, 4 or 5 substituents mutually independently selected from the group consisting of F, Cl, Br, I, —CN, —NO$_2$, —OH, —O—$C_{1-5}$ alkyl, —SH, —S—$C_{1-5}$ alkyl, —NH$_2$, —NH—$C_{1-5}$ alkyl and —N($C_{1-5}$ alkyl)($C_{1-5}$ alkyl);

$R^5$, $R^{17}$, $R^{18}$, $R^{24}$ and $R^{25}$ mutually independently in each case denote
an alkyl residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl residue may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$),
or an alkenyl residue selected from the group consisting of vinyl, 1-propenyl, 2-propenyl, 1-butenyl, 2-butenyl and 3-butenyl, wherein the alkenyl residue may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

$R^6$, $R^7$, $R^{13}$, $R^{16}$ and $R^{26}$, mutually independently, in each case denote
a hydrogen residue
an alkyl residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl residue may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$),
or an alkenyl residue selected from the group consisting of vinyl, 1-propenyl, 2-propenyl, 1-butenyl, 2-butenyl and 3-butenyl, wherein the alkenyl residue may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$HO)$_2$ and —N(CH$_3$)(C$_2$H$_5$);

$R^8$, $R^9$, $R^{21}$, $R^{22}$, $R^{23}$, $R^{30}$ and $R^{31}$, mutually independently, in each case denote
a (hetero)cycloaliphatic residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, wherein the (hetero)cycloaliphatic residue may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—OH, —C(=O)—O—C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —(CH$_2$)-benzo[b]furanyl, —O-phenyl, —O-benzyl, phenyl, benzyl, naphthyl and —(CH$_2$)-naphthyl, wherein in each case the cyclic moiety of the residues —O-phenyl, —O-benzyl, phenyl, —(CH$_2$)-benzo[b]furanyl, benzyl, naphthyl and —(CH$_2$)-naphthyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

or a residue selected from the group consisting of phenyl, naphthyl, (1,3)-benzodioxolyl, (1,4)-benzodioxanyl, thiophenyl, furanyl, pyrrolyl, pyrazolyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, wherein the residue may in each case be substituted with 1, 2, 3, 4 or 5 substituents mutually independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—O—C$_{1-5}$ alkyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —S(=O)$_2$—NH$_2$, —S(=O)$_2$—NH—C$_{1-5}$ alkyl, —(CH$_2$)-benzo[b]furanyl, —O-phenyl, —O-benzyl, phenyl and benzyl, wherein in each case the cyclic moiety of the residues —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

$R^{10}$, $R^{11}$, $R^{12}$, $R^{14}$ and $R^{20}$, mutually independently, in each case denote an alkyl residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl residue may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);

a (hetero)cycloaliphatic residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl and indenyl, wherein the (hetero)cycloaliphatic residue may be in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—O—C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —(CH$_2$)-benzo[b]furanyl, —O-phenyl, —O-benzyl, phenyl, benzyl, naphthyl and —(CH$_2$)-naphthyl, wherein in each case the cyclic moiety of the substituents —O-phenyl, —O-benzyl, phenyl, —(CH$_2$)-benzo[b]furanyl, benzyl, naphthyl and —(CH$_2$)-naphthyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —C$_{1-5}$ alkyl, —S—CF$_3$, phenyl and —O-benzyl and optionally the (hetero)cycloaliphatic residue may be attached via a —(CH$_2$)—, —CH(CH$_3$)—, —(CH$_2$)—(CH$_2$)—, —(CH$_2$)—(CH$_2$)—(CH$_2$)— or —(CH$_2$)—(CH=CH)-—group;

or a residue selected from the group consisting of phenyl, naphthyl, thiophenyl, furanyl, pyrrolyl, pyrazolyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl and thieno[2,3-d]pyrimidinyl, wherein the residue may in each case be substituted with 1, 2, 3, 4 or 5 substituents mutually independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—O—C$_{1-5}$ alkyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —S(=O)$_2$—NH$_2$, —S(=O)$_2$—NH—C$_{1-5}$ alkyl, —(CH$_2$)-benzo[b]furanyl, —O-phenyl, —O-benzyl, phenyl and benzyl and/or be attached via a —(CH$_2$)—, —CH(CH$_3$)—, —(CH$_2$)—(CH$_2$)—, —(CH$_2$)—(CH$_2$)—(CH$_2$)— or —(CH$_2$)—(CH=CH)— group, wherein in each case the cyclic moiety of the substituents —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

$R^{15}$ and $R^{27}$, mutually independently, in each case denote an alkyl residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl residue may in each case be substituted with 1, 2, 3, 4 or 5 substituents mutually independently selected from F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

an alkenyl residue selected from the group consisting of vinyl, 1-propenyl, 2-propenyl, 1-butenyl, 2-butenyl and 3-butenyl, wherein the alkenyl-residue may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

a (hetero)cycloaliphatic residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl and 7,7-dimethyl-2-oxa-bicyclo[2.2.1]heptyl, wherein the (hetero)cycloaliphatic residue may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—OH, —C(=O)—O—C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

or a residue selected from the group consisting of phenyl, naphthyl, (1,3)-benzodioxolyl, (1,4)-benzodioxanyl, thiophenyl, furanyl, pyrrolyl, pyrazolyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, wherein the residue may in each case be substituted with 1, 2, 3, 4 or 5 substituents mutually independently selected from the group consisting of F, Cl, Br, I, —CN, —CF$_3$, —SF$_5$, —OH, O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—O—C$_{1-5}$ alkyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —S(=O)$_2$—NH$_2$, —S(=O)$_2$—NH—C$_{1-5}$ alkyl, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

$R^{19}$ denotes a residue selected from the group consisting of phenyl, naphthyl, thiophenyl, furanyl and pyridinyl, wherein the residue may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, methyl, ethyl, n-propyl, isopropyl, n-butyl, sec-butyl, isobutyl, tert-butyl, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —NH—C(=O)—CH$_3$, —NH—C(=O)—C$_2$H$_5$, —C(=O)—H, —C(=O)—CH$_3$, —C(=O)—C$_2$H$_5$, —C(=O)—NH$_2$, —C(=O)—NH—CH$_3$, —C(=O)—N—(CH$_3$)$_2$, phenyl and benzyl and/or be attached via a —(CH$_2$)—, —(CH$_2$)—(CH$_2$)— or —(CH$_2$)—O—(CH$_2$)— group;

and $R^{28}$ and $R^{29}$, mutually independently, in each case denote an alkyl residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl residue may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

or a residue selected from the group consisting of phenyl, naphthyl, thiophenyl, furanyl, pyrrolyl, pyrazolyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, wherein the residue may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, O—CH$_2$F, —S—CF$_3$, —S—CHF$_2$, —S—CH$_2$F, —SH, —S—CH$_3$, —S—C$_2$H$_5$, methyl, ethyl, n-propyl, isopropyl, n-butyl, sec-butyl, isobutyl, tert-butyl, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —NH—C(=O)—CH$_3$, —NH—C(=O)—C$_2$H$_5$, —C(=O)—H, —C(=O)—CH$_3$, —C(=O)—C$_2$H$_5$, —C(=O)—NH$_2$, —C(=O)—NH—CH$_3$, —C(=O)—N—(CH$_2$)$_2$, —S(=O)$_2$—NH$_2$, —S(=O)$_2$—CH$_3$, phenyl and benzyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred substituted 4,5,6,7-tetrahydro-isoxazolo[4,5-c]pyridine compounds of the above-stated general formula I are those in which $R^1$ denotes —(CHR$^4$)—C(=O)—OR$^5$, —(CHR$^4$)—(CH$_2$)—C(=O)—OR$^5$ or —(CHR$^4$)—(CH$_2$)—(CH$_2$)—C(=O)—OR$^5$;

—(CHR⁶)—R⁸, —(CHR⁶)—(CHR⁷)—R⁸, —(CHR⁶)—(CHR⁷)—V—R⁸, —(CHR⁶)—(CHR⁷)—(CH₂)—R⁸, —(CHR⁶)—(CHR⁷)—(CH₂)—W—R⁸ or —(CHR⁶)—(CHR⁷)—(CH₂)—W—(CH₂)—R⁸, in which V and W mutually independently in each case denote O, S, NH, N(CH₃) or N(C₂H₅);

an alkyl residue selected from the group consisting of methyl, ethyl, n-propyl, isopropyl, n-butyl, sec-butyl, isobutyl, tert-butyl, n-pentyl, sec-pentyl, —(CH₂)—(CH₂)—(C(CH₃)₃), n-hexyl, n-heptyl, n-octyl and —(CH₂)—(CH)(C₂H₅)—(CH₂)—(CH₂)—(CH₂)—(CH₃), wherein the alkyl residue may in each case be substituted with 1, 2, 3, 4 or 5 substituents mutually independently selected from the group consisting of F, Cl, Br, I, —CN, —NO₂, —OH, —O—CH₃, —O—C₂H₅, —SH, —S—CH₃, —S—C₂H₅, —NH₂, —NH—CH₃, —NH—C₂H₅, —N(CH₃)₂, —N(C₂H₅)₂ and —N(CH₃)(C₂H₅);

an alkynyl residue selected from the group consisting of ethynyl, 1-propynyl, 2-propynyl, 1-butynyl, 2-butynyl and 3-butynyl;

a (hetero)cycloaliphatic residue selected from the group consisting of cyclopropyl, cyclobutyl, cyclopentyl, cyclohexyl, cycloheptyl, (6,6)-dimethyl-[3.1.1]-bicycloheptyl, pyrrolidinyl, piperidinyl, morpholinyl, thiomorpholinyl, indanyl and indenyl, wherein the (hetero) cycloaliphatic residue may in each case be substituted with 1, 2, 3, 4 or 5 substituents mutually independently selected from the group consisting of oxo (=O), thioxo (=S), F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, isopropyl, n-butyl, sec-butyl, isobutyl, tert-butyl, —C(=O)—H, —C(=O)—CH₃, —C(=O)—C₂H₅, —C(=O)—C(CH₃)₃, —C(=O)—OH, —C(=O)—O—CH₃, —C(=O)—O—C₂H₅, —(CH₂)—C(=O)—OH, —(CH₂)—C(=O)—O—CH₃, —(CH₂)—C(=O)—O—C₂H₅, —N(CH₃)₂, —N(C₂H₅)₂, —N(H)(CH₃), —N(H)(C₂H₅), —(CH₂)-benzo[b]furanyl, —O-phenyl, —O-benzyl, phenyl, benzyl, naphthyl and —(CH₂)-naphthyl, wherein the cyclic moiety of the benzyl residue may be substituted with 1, 2, 3, 4 or 5 substituents mutually independently selected from the group consisting of F, Cl, Br, —OH, —CF₃, —SF₅, —CN, —NO₂, —O—CH₃, —O—C₂H₅ and —O—CF₃, or a residue selected from the group consisting of phenyl, naphthyl, (1,3)-benzodioxolyl, (1,4)-benzodioxanyl, thiophenyl, furanyl, pyridinyl, imidazolyl and indolyl, wherein the residue may in each case be substituted with 1, 2, 3, 4 or 5 substituents mutually independently selected from the group consisting of F, Cl, Br, I, —CN, —CF₃, —SF₅, —OH, —O—CH₃, —O—C₂H₅, —NH₂, —NO₂, —O—CF₃, —O—CHF₂, —O—CH₂F, —S—CF₃, —S—CHF₂, —S—CH₂F, —SH, methyl, ethyl, n-propyl, isopropyl, n-butyl, sec-butyl, isobutyl and tert-butyl;

$R^2$ denotes a hydrogen residue or

—(CH₂)—R⁹, or $R^1$ and $R^2$, together with the nitrogen atom joining them together as a ring member, form a residue which is selected from the group consisting of

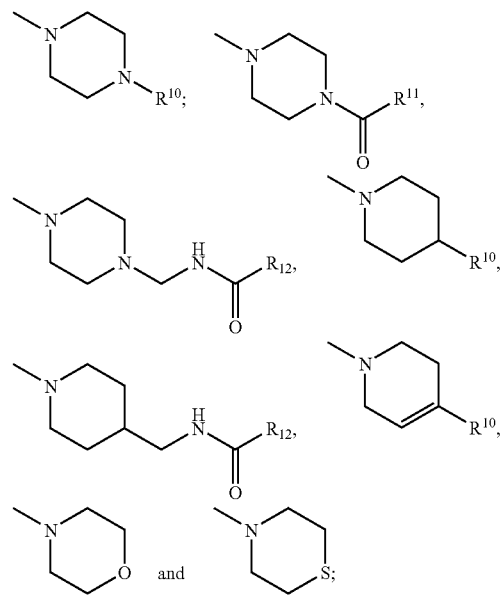

$R^3$ denotes —C(=O)—NR¹³R¹⁴;
—C(=O)—R¹⁵;
—C(=O)—(CH₂)—O—(CH₂)—C(=O)—OR¹⁶, —C(=O)—(CH₂)—CR¹⁷R¹⁸—(CH₂)—C(=O)—OR¹⁶, —C(=O)—CR¹⁷R¹⁸—(CH₂)—C(=O)—OR¹⁶ or —C(=O)—(CH₂)—(CH₂)—(CH₂)—C(=O)—OR¹⁶;
—C(=O)—(CHR¹⁹)—NH—C(=O)—OR²⁰;
—C(=O)—(CH₂)—R²¹, —C(=O)—(CH₂)—O—R²¹, —C(=O)—(CH₂)—O—(CH₂)—R²¹ or —C(=O)—(CH₂)—(CH₂)—(CH₂)—O—R²¹;
—C(=O)—(CH=CH)—R²²;
—S(=O)₂—R²³;
—S(=O)₂—NR²⁴R²⁵;
—C(=S)—NR²⁶—R²⁷, —C(=S)—NR²⁶—(CH₂)—R²⁷, —C(=S)—NR²⁶—(CH₂)—(CH₂)—R²⁷ or —C(=S)—NR²⁶—(CH₂)—(CH₂)—O—R²⁷;
—C(=S)—NR²⁶—(CHR²⁸)—R²⁹;
—C(=S)—NR²⁶—C(=O)—R³⁰;
or —(CH₂)—R³¹;

$R^4$ denotes —C(=O)—NH₂;
a hydrogen residue or
an alkyl residue selected from the group consisting of methyl, ethyl, n-propyl, isopropyl, n-butyl, sec-butyl, isobutyl, tert-butyl, -n-pentyl, sec-pentyl, —(CH₂)—(CH₂)—(C(CH₃)₃), n-hexyl, n-heptyl, n-octyl and —(CH₂)—(CH)(C₂H₅)—(CH₂)—(CH₂)—(CH₂)—(CH₃), wherein the alkyl residue may in each case be substituted with 1, 2, 3, 4 or 5 substituents mutually independently selected from the group consisting of F, Cl, Br, I, —CN, —NO₂, —OH, —O—CH₃, —O—C₂H₅, —SH, —S—CH₃, —S—C₂H₅, —NH₂, —NH—CH₃, —NH—C₂H₅, —N(CH₃)₂, —N(C₂H₅)₂ and —N(CH₃)(C₂H₅);

$R^5$ denotes an alkyl residue selected from the group consisting of methyl, ethyl, n-propyl, isopropyl, n-butyl, sec-butyl, isobutyl and tert-butyl;

$R^6$, $R^7$ and $R^{16}$, mutually independently, in each case denote a hydrogen residue or an alkyl residue selected from the group consisting of methyl, ethyl, n-propyl and isopropyl;

$R^8, R^9, R^{21}, R^{22}, R^{23}, R^{30}$ and $R^{31}$, mutually independently, in each case denote a (hetero)cycloaliphatic residue selected from the group consisting of cyclopropyl, cyclobutyl, cyclopentyl, cyclohexyl, cycloheptyl, pyrrolidinyl, piperidinyl, morpholinyl, thiomorpholinyl, indanyl and indenyl, wherein the (hetero)cycloaliphatic residue may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—H, —C(=O)—CH$_3$, —C(=O)—C$_2$H$_5$, —C(=O)—C(CH$_3$)$_3$, —C(=O)—OH, —C(=O)—O—CH$_3$, —C(=O)—O—C$_2$H$_5$, —(CH$_2$)—C(=O)—OH, —(CH$_2$)—C(=O)—O—CH$_3$, —(CH$_2$)—C(=O)—O—C$_2$H$_5$, —N(CH$_5$)$_2$, —N(C$_2$H$_5$)$_2$, —N(H)(CH$_3$), —N(H)(C$_2$H$_5$), phenyl and benzyl;

or a residue selected from the group consisting of phenyl, naphthyl, (1,3)-benzodioxolyl, (1,4)-benzodioxanyl, thiophenyl, furanyl, pyridinyl, imidazolyl, indolyl and isoindolyl, wherein the residue may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, methyl, ethyl, n-propyl, isopropyl, n-butyl, sec-butyl, isobutyl, tert-butyl, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), —C(=O)—H, —C(=O)—CH$_3$, —C(=O)—C$_2$H$_5$, —C(=O)—NH$_2$, —S(=O)$_2$—NH$_2$, —S(=O)$_2$—NH—CH$_3$, —O-phenyl, —O-benzyl, phenyl and benzyl;

$R^{10}, R^{11}, R^{12}, R^{14}$ and $R^{20}$, mutually independently, in each case denote an alkyl residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl and n-octyl, wherein the alkyl residue may in each case be substituted with 1, 2, 3, 4 or 5 substituents mutually independently selected from the group consisting of —N(CH$_3$)$_2$, —N(C$_2$H$_5$)$_2$, F, Cl and Br;

a cycloaliphatic residue selected from the group consisting of morpholinyl, piperidinyl, piperazinyl, pyrrolidinyl, cyclopropyl, cyclobutyl, cyclopentyl and cyclohexyl, wherein the cycloaliphatic residue may in each case be substituted with 1, 2 or 3 substituents mutually independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—H, —C(=O)—CH$_3$, —C(=O)—C$_2$H$_5$, —C(=O)—C(CH$_3$)$_3$, —C(=O)—OH, —C(=O)—O—CH$_3$, —C(=O)—O—C$_2$H$_5$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), phenyl and benzyl and/or be attached via a —(CH$_2$)— or —(CH$_2$)—(CH$_2$) group;

or a residue selected from the group consisting of phenyl, naphthyl, thiophenyl, furanyl, pyrrolyl, pyrazolyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl, isoquinolinyl and thieno[2,3-d]pyrimidinyl, wherein the residue may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, methyl, ethyl, n-propyl, isopropyl, n-butyl, sec-butyl, isobutyl, tert-butyl, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —C(=O)—H, —C(=O)—CH$_3$, —C(=O)—C$_2$H$_5$, —C(=O)—NH$_2$, —C(=O)—NH—CH$_3$, —C(=O)—N—(CH$_3$)$_2$, —S(=O)$_2$—NH$_2$, —S(=O)$_2$—CH$_3$, phenyl and benzyl and/or be attached via a —(CH$_2$)—, —CH(CH$_3$)—, —(CH$_2$)—(CH$_2$)—, —(CH$_2$)—(CH$_2$)—(CH$_2$)— or —(CH$_2$)—(CH=CH)— group;

$R^{13}$ and $R^{26}$ denote a hydrogen residue;

$R^{15}$ and $R^{27}$, mutually independently, in each case denote a residue selected from the group consisting of methyl, ethyl, n-propyl, isopropyl, n-butyl, sec-butyl, isobutyl, tert-butyl, vinyl, 1-propenyl, 2-propenyl, 1-butenyl, 2-butenyl and 3-butenyl;

a (hetero)cycloaliphatic residue selected from the group consisting of cyclopropyl, cyclobutyl, cyclopentyl, cyclohexyl and 7,7-dimethyl-2-oxa-bicyclo[2.2.1]heptyl, wherein the (hetero)cycloaliphatic residue may in each case be substituted with 1, 2 or 3 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—H, —C(=O)—CH$_3$, —C(=O)—C$_2$H$_5$, —C(=O)—C(CH$_3$)$_3$, —C(=O)—OH, —C(=O)—O—CH$_3$, —C(=O)—O—C$_2$H$_5$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), phenyl and benzyl;

or a residue selected from the group consisting of phenyl, naphthyl, thiophenyl, furanyl, pyrrolyl, pyrazolyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, wherein the residue may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, methyl, ethyl, n-propyl, isopropyl, n-butyl, sec-butyl, isobutyl, tert-butyl, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —NH—C(=O)—CH$_3$, —NH—C(=O)—C$_2$H$_5$, —C(=O)—H, —C(=O)—CH$_3$, —C(=O)—

C₂H₅, —C(=O)—NH₂, —C(=O)—NH—CH₃, —C(=O)—N—(CH₃)₂, —S(=O)₂—NH₂, —S(=O)₂—CH₃, phenyl and benzyl;

R¹⁷ and R¹⁸, mutually independently, in each case denote a methyl or ethyl residue;

R¹⁹ denotes a phenyl residue, which may be attached a —(CH₂)—, —(CH₂)—(CH₂)— or —(CH₂)—O—(CH₂)— group;

R²⁴ and R²⁵, mutually independently, in each case denote a methyl or ethyl residue;

R²⁸ denotes a phenyl residue, which may be substituted with 1, 2, 3, 4 or 5 substituents mutually independently selected from the group consisting of F, Cl, Br, I, —CN, —CF₃, —SF₅, —OH, —O—CH₃, —O—C₂H₅, —NH₂, —NO₂, —O—CF₃, —O—CHF₂, —O—CH₂F, —S—CF₃, —S—CHF₂, —S—CH₂F, —SH, —S—CH₃, —S—C₂H₅, methyl, ethyl, n-propyl, isopropyl, n-butyl, sec-butyl, isobutyl, tert-butyl; and R²⁹ denotes an alkyl residue selected from the group consisting of methyl, ethyl, n-propyl, isopropyl, n-butyl, isobutyl and tert-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred substituted 4,5,6,7-tetrahydroisoxazolo[4,5-c]pyridine compounds of the above-stated general formula I are those in which R¹ denotes —(CHR⁴)—C(=O)—OR⁵, —(CHR⁴)—(CH₂)—C(=O)—OR⁵ or —(CHR⁴)—(CH₂)—(CH₂)—C(=O)—OR⁵;
—(CHR⁶)—R⁸, —(CHR⁶)—(CHR⁷)—R⁸, —(CHR⁶)—(CHR⁷)—O—R⁸, —(CHR⁶)—(CHR⁷)—(CH₂)—R⁸ or —(CHR⁶)—(CHR⁷)—(CH₂)—N(CH₃)—R⁸;

an optionally substituted alkyl residue selected from the group consisting of methyl, ethyl, n-propyl, isopropyl, —(CH₂)—(CH₂)—CN, —(CH₂)—(CH₂)—N(CH₃)₂, —(CH₂)—(CH₂)—O—CH₃, —(CH₂)—(CH₂)—S—C₂H₅, -n-butyl, sec-butyl, isobutyl, tert-butyl, —(CH₂)—(CH₂)—O—CH₃, n-pentyl, sec-pentyl, —(CH₂)—(CH₂)—(C(CH₃)₃), n-hexyl, n-heptyl, n-octyl and —(CH₂)—(CH)(C₂H₅)—(CH₂)—(CH₂)—(CH₂)—(CH₃);

an alkynyl residue selected from the group consisting of 1-propynyl and 2-propynyl;

a cycloaliphatic residue selected from the group consisting of cyclopropyl, cyclobutyl, cyclopentyl, cyclohexyl, cycloheptyl, (6,6)-dimethyl-[3.1.1]-bicycloheptyl, indanyl and indenyl, wherein the cycloaliphatic residue may in each case be substituted with an —O-benzyl residue or a methyl residue, a pyrrolidinyl or piperidinyl residue, which may in each case be substituted on the nitrogen atom with a substituent selected from the group consisting of —C(=O)—CH₃, —C(=O)—C₂H₅, —C(=O)—C(CH₃)₃, benzyl, —C(=O)—OC₂H₅ and —(CH₂)-naphthyl, wherein the cyclic moiety of the benzyl residue may be substituted with 1, 2 or 3 substituents mutually independently selected from the group consisting of F, Cl, Br, —CF₃ and —O—CF₃, or a phenyl residue, which may be substituted with 1, 2 or 3 substituents mutually independently selected from the group consisting of —O—CH₃, —O—C₂H₅, methyl, ethyl, n-propyl, isopropyl, n-butyl, sec-butyl, isobutyl and tert-butyl;

R² denotes a hydrogen residue or
—(CH₂)—R⁹;
or
R¹ and R², together with the nitrogen atom joining them together as a ring member, form a residue which is selected from the group consisting of

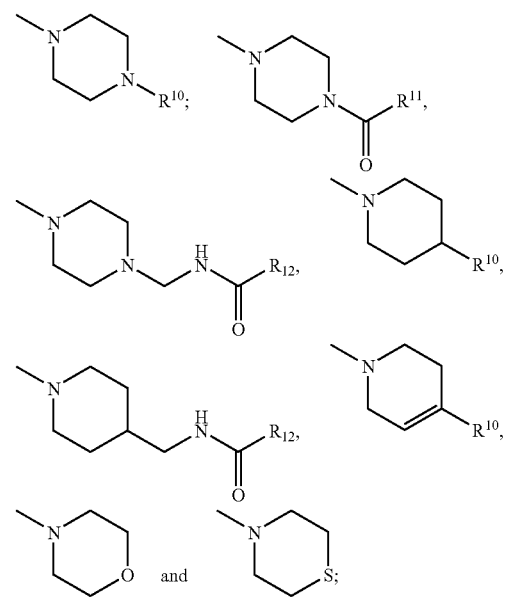

R³ denotes —C(=O)—NR¹³R¹⁴;
—C(=O)—R¹⁵;
—C(=O)—(CH₂)—O—(CH₂)—C(=O)—OR¹⁶,
—C(=O)—(CH₂)—CR¹⁷R¹⁸—(CH₂)—C(=O)—OR¹⁶, —C(=O)—CR¹⁷R¹⁸—(CH₂)—C(=O)—OR¹⁶ or —C(=O)—(CH₂)—(CH₂)—(CH₂)—C(=O)—OR¹⁶;
—C(=O)—(CHR¹⁹)—NH—C(=O)—OR²⁰;
—C(=O)—(CH₂)—R²¹, —C(=O)—(CH₂)—O—R²¹, —C(=O)—(CH₂)—O—(CH₂)—R²¹ or —C(=O)—(CH₂)—(CH₂)—(CH₂)—O—R²¹;
—C(=O)—(CH=CH)—R²²;
—S(=O)₂—R²³;
—S(=O)₂—NR²⁴R²⁵;
—C(=S)—NR²⁶—R²⁷, —C(=S)—NR²⁶—(CH₂)R²⁷, —C(=S)—NR²⁶—(CH₂)—(CH₂)—R²⁷ or —C(=S)—NR²⁶—(CH₂)—(CH₂)—O—R²⁷;
—C(=S)—NR²⁶—(CHR²⁸)—R²⁹;
—C(=S)—NR²⁶—C(=O)—R³⁰; or —(CH₂)—R³¹;

R⁴ denotes —C(=O)—NH₂;
a hydrogen residue or
an alkyl residue selected from the group consisting of methyl, ethyl, n-propyl, isopropyl and n-butyl;

R⁵ denotes an alkyl residue selected from the group consisting of methyl, ethyl, n-propyl, isopropyl, n-butyl, sec-butyl, isobutyl and tert-butyl;

R⁶, R⁷ and R¹⁶, mutually independently, in each case denote a hydrogen residue or an alkyl residue selected from the group consisting of methyl, ethyl, n-propyl and isopropyl;

R⁸ denotes a (hetero)cycloaliphatic residue selected from the group consisting of cyclopropyl, cyclobutyl, cyclopentyl, cyclohexyl, pyrrolidinyl, piperidinyl, morpholinyl and thiomorpholinyl or a residue selected from the group consisting of phenyl, naphthyl, thiophenyl, furanyl, pyridinyl and indolyl, wherein the residue may in each case be substituted with 1, 2 or 3 substituents mutually independently selected from the group consisting of F, Cl, Br, —$CF_3$, —O—$CH_3$, —O—$C_2H_5$, —O—$CH_2$—CH=$CH_2$, methyl, ethyl, n-propyl, isopropyl, n-butyl, tert-butyl, —S—$CH_3$, —S—$C_2H_5$, —S(=O)$_2$—$NH_2$ and —S(=O)$_2$—NH—$CH_3$;

$R^9$ denotes a residue selected from the group consisting of phenyl, naphthyl, thiophenyl, furanyl and pyridinyl;

$R^{10}$ denotes an optionally substituted alkyl residue selected from the group consisting of —($CH_2$)—N($CH_3$)$_2$, —($CH_2$)—($CH_2$)—N($CH_3$)$_2$, —($CH_2$)—($CH_2$)—($CH_2$)—N($CH_3$)$_2$, —($CH_2$)—N($C_2H_5$)$_2$, —($CH_2$)—($CH_2$)—N($C_2H_5$)$_2$ and —($CH_2$)—($CH_2$)—($CH_2$)—N($C_2H_5$)$_2$;

a cycloaliphatic residue selected from the group consisting of piperazinyl, pyrrolidinyl, piperidinyl, morpholinyl, cyclopropyl, cyclobutyl, cyclopentyl and cyclohexyl, wherein the cycloaliphatic residue may be attached via a —($CH_2$)— or —($CH_2$)—($CH_2$)— or —($CH_2$)—($CH_2$)—($CH_2$)— group;

or a residue selected from the group consisting of phenyl, thiazolyl, naphthyl and thieno[2,3-d]pyrimidinyl, wherein the residue may in each case be substituted with 1, 2 or 3 substituents mutually independently selected from the group consisting of F, Cl, Br, methyl, ethyl, n-propyl, —C(=O)—$CH_3$ and —C(=O)—$C_2H_5$ and/or be attached via a —($CH_2$)—, —CH($CH_3$)—, —($CH_2$)—($CH_2$)—, —($CH_2$)—($CH_2$)—($CH_2$)— or —($CH_2$)—(CH=CH)— group;

$R^{11}$ denotes an optionally substituted alkyl residue selected from the group consisting of methyl, ethyl, n-propyl, —$CF_3$ and —$CF_2$—$CF_3$, or a residue selected from the group consisting of phenyl, and naphthyl, wherein the residue may in each case be substituted with 1, 2 or 3 substituents mutually independently selected from the group consisting of F, Cl and Br and/or be attached via a —($CH_2$)— or —($CH_2$)—($CH_2$)— group;

$R^{12}$ denotes an optionally substituted alkyl residue selected from the group consisting of methyl, ethyl, n-propyl, —$CF_3$ and —$CF_2$—$CF_3$;

$R^{13}$ denotes a hydrogen residue;

$R^{14}$ denotes a residue selected from the group consisting of phenyl and naphthyl, wherein the residue may in each case be substituted with 1, 2 or 3 substituents mutually independently selected from the group consisting of F, Cl, Br, —CN, —$CF_3$, —O—$CH_3$, —O—$C_2H_5$, —O—CH($CH_3$)$_2$, —O—$CH_2$—$CH_2$—$CH_2$—$CH_3$, —$NO_2$, —O—$CF_3$, —O—$CHF_2$, —O—$CH_2F$, —S—$CF_3$, —S—$CHF_2$, —S—$CH_2F$, methyl, ethyl, n-propyl, isopropyl, n-butyl, sec-butyl, isobutyl, tert-butyl, —C(=O)—O—$CH_3$, —C(=O)—O—$C_2H_5$, —C(=O)—$CH_3$ and —C(=O)—$C_2H_5$ and/or be attached via a —($CH_2$)—, —CH($CH_3$)— or —($CH_2$)—($CH_2$)-group;

$R^{15}$ denotes a residue selected from the group consisting of 1-butenyl, 2-butenyl and 3-butenyl;

a 4,7,7-trimethyl-3-oxo-2-oxa-bicyclo[2.2.1]heptyl residue or a residue selected from the group consisting of phenyl, naphthyl, thiophenyl, furanyl, triazolyl, pyridinyl, quinolinyl, pyrazolyl and isoquinolinyl, wherein the residue may in each case be substituted with 1, 2 or 3 substituents mutually independently selected from the group consisting of F, Cl, Br, —$CF_3$, —O—$CH_3$, —O—$C_2H_5$, —O—CH($CH_3$)$_2$, —O—$CH_2$—$CH_2$—$CH_2$—$CH_3$, —O—$CF_3$, —O—$CHF_2$, —O—$CH_2F$, —S—$CF_3$, —S—$CHF_2$, —S—$CH_2F$, methyl, ethyl, n-propyl, isopropyl, n-butyl, sec-butyl, isobutyl, tert-butyl, phenyl, —NH—C(=O)—$CH_3$ and —NH—C(=O)—$C_2H_5$;

$R^{17}$ and $R^{18}$ mutually independently in each case denote a methyl or ethyl residue;

$R^{19}$ denotes a phenyl residue, which may be attached via a —($CH_2$)—, —($CH_2$)—($CH_2$)— or —($CH_2$)—O—($CH_2$)— group;

$R^{20}$ denotes an alkyl residue selected from the group consisting of methyl, ethyl, n-propyl, isopropyl, n-butyl, sec-butyl, isobutyl and tert-butyl or a benzyl residue;

$R^{21}$ denotes a cycloaliphatic residue selected from the group consisting of cyclopropyl, cyclobutyl, cyclopentyl, cyclohexyl, cycloheptyl, wherein the cycloaliphatic residue may in each case be substituted with 1, 2 or 3 substituents mutually independently selected from the group consisting of —C(=O)—OH and —($CH_2$)—C(=O)—OH, or a residue selected from the group consisting of phenyl, naphthyl, (1,3)-benzodioxolyl and (1,4)-benzodioxanyl, wherein the residue may in each case be substituted with 1, 2 or 3 substituents mutually independently selected from the group consisting of F, Cl, Br, —O—$CH_3$ and —O—$C_2H_5$;

$R^{22}$ denotes a phenyl residue;

$R^{23}$ denotes a residue selected from the group consisting of phenyl, naphthyl, thiophenyl, furanyl and pyridinyl, wherein the residue may in each case be substituted with 1, 2 or 3 substituents mutually independently selected from the group consisting of F, Cl, Br, —$CF_3$, —O—$CH_3$, —O—$C_2H_5$, —O—CH($CH_3$)$_2$, —O—$CH_2$—$CH_2$—$CH_2$—$CH_3$, —O—$CF_3$, O—$CHF_2$, —O—$CH_2F$, methyl, ethyl, n-propyl, isopropyl, n-butyl, sec-butyl, isobutyl and tert-butyl;

$R^{24}$ and $R^{25}$, mutually independently, in each case denote a methyl or ethyl residue;

$R^{26}$ denotes a hydrogen residue;

$R^{27}$ denotes an alkyl residue selected from the group consisting of methyl, ethyl, n-propyl, isopropyl and n-butyl;

a cyclohexyl residue or a phenyl residue, which may be substituted with 1, 2, 3, 4 or 5 substituents mutually independently selected from the group consisting of F, Cl, Br, —O—$CH_3$ and —O—$C_2H_5$;

$R^{28}$ denotes a phenyl residue, which may be substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —O—$CHF_2$, —O—$CH_2F$, —S—$CF_3$, —S—$CHF_2$, —S—$CH_2F$, —SH, —S—$CH_3$, —S—$C_2H_5$, methyl, ethyl, n-propyl, isopropyl, n-butyl, sec-butyl, isobutyl, tert-butyl;

$R^{29}$ denotes an alkyl residue selected from the group consisting of methyl, ethyl, n-propyl, isopropyl, n-butyl, isobutyl and tert-butyl;

$R^{30}$ denotes a phenyl residue and $R^{31}$ denotes a residue selected from the group consisting of phenyl and naphthyl, wherein the residue may in each case be substituted with 1, 2 or 3 substituents mutually independently selected from the group consisting of F, Cl and Br;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted 4,5,6,7-tetrahydro-isoxazolo[4,5-c]pyridine compounds of the above-stated general formula I which are in particular preferred are those selected from the group consisting of

[1] 6,7-dihydro-4H-isoxazolo[4,5-c]pyridine-3,5-dicarboxylic acid 3-[(2-methoxy-ethyl) amide] 5-[(3-methoxyphenyl) amide],
[2] 6,7-dihydro-4H-isoxazolo[4,5-c]pyridine-3,5-dicarboxylic acid 3-cyclopentyl amide 5-(4-fluorobenzyl amide),
[3] 6,7-dihydro-4H-isoxazolo[4,5-c]pyridine-3,5-dicarboxylic acid 3-phenyl amide 5-[(4-trifluoromethoxy-phenyl) amide],
[4] 6,7-dihydro-4H-isoxazolo[4,5-c]pyridine-3,5-dicarboxylic acid 5-[(4-methyl-3-nitro-phenyl) amide] 3-(phenethyl amide),
[5] 6,7-dihydro-4H-isoxazolo[4,5-c]pyridine-3,5-dicarboxylic acid 3-[(2-methoxy-ethyl) amide] 5-[(4-methyl-3-nitro-phenyl) amide],
[6] 3-{[5-(2,5-difluoro-phenylcarbamoyl)-4,5,6,7-tetrahydro-isoxazolo[4,5-c]pyridine-3-carbonyl]-amino}-propionic acid ethyl ester,
[7] 6,7-dihydro-4H-isoxazolo[4,5-c]pyridine-3,5-dicarboxylic acid 5-[(4-butoxy-phenyl) amide] 3-[(2-methoxy-ethyl) amide],
[8] 6,7-dihydro-4H-isoxazolo[4,5-c]pyridine-3,5-dicarboxylic acid 5-[(4-fluorophenyl) amide] 3-(phenethyl amide),
[9] 6,7-dihydro-4H-isoxazolo[4,5-c]pyridine-3,5-dicarboxylic acid 5-[(4-methyl-3-nitro-phenyl) amide] 3-[(thiophen-2-ylmethyl) amide],
[10] 6,7-dihydro-4H-isoxazolo[4,5-c]pyridine-3,5-dicarboxylic acid 3-benzyl amide 5-(phenethyl amide),
[11] 6,7-dihydro-4H-isoxazolo[4,5-c]pyridine-3,5-dicarboxylic acid 3-[(2-ethylsulfanyl-ethyl) amide] 5-[(3-methoxyphenyl) amide],
[12] 6,7-dihydro-4H-isoxazolo[4,5-c]pyridine-3,5-dicarboxylic acid 5-[(3-cyano-phenyl) amide] 3-[(thiophen-2-ylmethyl) amide],
[13] 6,7-dihydro-4H-isoxazolo[4,5-c]pyridine-3,5-dicarboxylic acid 5-[(4-ethoxy-phenyl) amide] 3-phenyl amide,
[14] 6,7-dihydro-4H-isoxazolo[4,5-c]pyridine-3,5-dicarboxylic acid 3-(4-fluorobenzyl amide) 5-[(4-methyl-3-nitro-phenyl) amide],
[15] 6,7-dihydro-4H-isoxazolo[4,5-c]pyridine-3,5-dicarboxylic acid 5-[(3-acetyl-phenyl) amide] 3-[(5-methyl-furan-2-ylmethyl) amide],
[16] 6,7-dihydro-4H-isoxazolo[4,5-c]pyridine-3,5-dicarboxylic acid 5-[(4-methyl-3-nitro-phenyl) amide] 3-prop-2-ynyl amide,
[17] 6,7-dihydro-4H-isoxazolo[4,5-c]pyridine-3,5-dicarboxylic acid 3-benzyl amide 5-phenyl amide,
[18] 6,7-dihydro-4H-isoxazolo[4,5-c]pyridine-3,5-dicarboxylic acid 5-[(1-naphthalen-1-yl-ethyl) amide] 3-(phenethyl amide),
[19] 6,7-dihydro-4H-isoxazolo[4,5-c]pyridine-3,5-dicarboxylic acid 5-[(3-fluorophenyl) amide] 3-prop-2-ynyl amide,
[20] 3-{[5-(2,5-dimethoxy-phenylcarbamoyl)-4,5,6,7-tetrahydro-isoxazolo[4,5-c]pyridine-3-carbonyl]-amino}-propionic acid ethyl ester,
[21] 6,7-dihydro-4H-isoxazolo[4,5-c]pyridine-3,5-dicarboxylic acid 5-[(4-ethoxy-phenyl) amide] 3-(4-fluorobenzyl amide),
[22] 6,7-dihydro-4H-isoxazolo[4,5-c]pyridine-3,5-dicarboxylic acid 5-[(5-chloro-2-methoxyphenyl) amide] 3-(phenethyl amide),
[23] 3-({3-[(5-methyl-furan-2-ylmethyl)-carbamoyl]-6,7-dihydro-4H-isoxazolo[4,5-c]pyridine-5-carbonyl}-amino)-benzoic acid ethyl ester,
[24] 6,7-dihydro-4H-isoxazolo[4,5-c]pyridine-3,5-dicarboxylic acid 5-[(5-chloro-2-methoxyphenyl) amide] 3-(isobutyl-amide),
[25] [2-oxo-2-(3-prop-2-ynylcarbamoyl-6,7-dihydro-4H-isoxazolo[4,5-c]pyridin-5-yl)-ethoxy]acetic acid,
[26] 3-ethyl-5-[3-(2-methoxy-ethylcarbamoyl)-6,7-dihydro-4H-isoxazolo[4,5-c]pyridin-5-yl]-3-methyl-5-oxo-pentanoic acid,
[27] (1-benzyloxymethyl-2-oxo-2-{3-[(pyridin-3-ylmethyl)-carbamoyl]-6,7-dihydro-4H-isoxazolo[4,5-c]pyridin-5-yl}-ethyl)-carbamic acid tert-butyl ester,
[28] {1-[2-oxo-2-(3-phenylcarbamoyl-6,7-dihydro-4H-isoxazolo[4,5-c]pyridin-5-yl)-ethyl]-cyclopentyl}acetic acid,
[29] 3-ethyl-3-methyl-5-oxo-5-(3-phenylcarbamoyl-6,7-dihydro-4H-isoxazolo[4,5-c]pyridin-5-yl)-pentanoic acid,
[30] (2-oxo-2-{3-[(thiophen-2-ylmethyl)-carbamoyl]-6,7-dihydro-4H-isoxazolo[4,5-c]pyridin-5-yl}-ethoxy)acetic acid,
[31] 3,3-dimethyl-4-{3-[(5-methyl-furan-2-ylmethyl)-carbamoyl]-6,7-dihydro-4H-isoxazolo[4,5-c]pyridin-5-yl}-4-oxo-butanoic acid,
[32] 5-(4-trifluoromethoxy-benzenesulfonyl)-4,5,6,7-tetrahydro-isoxazolo[4,5-c]pyridine-3-carboxylic acid benzyl-phenethyl amide,
[33] 5-benzenesulfonyl-4,5,6,7-tetrahydro-isoxazolo[4,5-c]pyridine-3-carboxylic acid (1-naphthalen-2-ylmethyl-pyrrolidin-3-yl) amide,
[34] [5-(4-fluoro-benzenesulfonyl)-4,5,6,7-tetrahydro-isoxazolo[4,5-c]pyridin-3-yl]-(4-thieno[2,3-d]pyrimidine-4-yl-piperazin-1-yl)-methanone,
[35] 5-(4-fluoro-benzenesulfonyl)-4,5,6,7-tetrahydro-isoxazolo[4,5-c]pyridine-3-carboxylic acid (3-phenyl-propyl) amide,
[36] 5-(3-phenyl-acryloyl)-4,5,6,7-tetrahydro-isoxazolo[4,5-c]pyridine-3-carboxylic acid (2-dimethylamino-ethyl) amide,
[37] 5-(2-phenoxy-acetyl)-4,5,6,7-tetrahydro-isoxazolo[4,5-c]pyridine-3-carboxylic acid (2-dimethylamino-ethyl) amide,
[38] 5-(4-fluoro-benzenesulfonyl)-4,5,6,7-tetrahydro-isoxazolo[4,5-c]pyridine-3-carboxylic acid (1-methyl-3-phenyl-propyl) amide,
[39] 5-(4-fluoro-benzenesulfonyl)-4,5,6,7-tetrahydro-isoxazolo[4,5-c]pyridine-3-carboxylic acid [1-(4-trifluoromethyl-benzyl)-pyrrolidin-3-yl] amide,
[40] 5(2,5-dichloro-benzenesulfonyl)-4,5,6,7-tetrahydro-isoxazolo[4,5-c]pyridine-3-carboxylic acid (2-benzyloxy-cyclopentyl) amide,
[41] 5-(5-tert-butyl-2-methyl-2H-pyrazole-3-carbonyl)-4,5,6,7-tetrahydro-isoxazolo[4,5-c]pyridine-3-carboxylic acid (2-dimethylamino-ethyl) amide,
[42] [5-(4-fluoro-benzenesulfonyl)-4,5,6,7-tetrahydro-isoxazolo[4,5-c]pyridin-3-yl]-[4-(4-fluorophenyl)-3,6-dihydro-2H-pyridin-1-yl]-methanone,
[43] 4-{[5-(4-fluoro-benzenesulfonyl)-4,5,6,7-tetrahydro-isoxazolo[4,5-c]pyridine-3-carbonyl]-amino}-piperidine-1-carboxylic acid ethyl ester,
[44] 5-(3-phenyl-acryloyl)-4,5,6,7-tetrahydro-isoxazolo[4,5-c]pyridine-3-carboxylic acid cyclopentyl amide,

[45] 5-(4-acetylamino-benzoyl)-4,5,6,7-tetrahydro-isoxazolo[4,5-c]pyridine-3-carboxylic acid cyclopropylmethyl amide,

[46] 5-(5-methyl-2-phenyl-2H-[1,2,3]triazole-4-carbonyl)-4,5,6,7-tetrahydro-isoxazolo[4,5-c]pyridine-3-carboxylic acid (pyridin-3-ylmethyl)-amide,

[47] 5-benzenesulfonyl-4,5,6,7-tetrahydro-isoxazolo[4,5-c]pyridine-3-carboxylic acid 3,4-dimethoxy-benzyl amide,

[48] 2-(3,4-difluoro-phenyl)-1-{4-[5-(4-fluoro-benzenesulfonyl)-4,5,6,7-tetrahydro-isoxazolo[4,5-c]pyridine-3-carbonyl]-piperazin-1-yl}-ethanone,

[49] 3-(morpholine-4-carbonyl)-6,7-dihydro-4H-isoxazolo[4,5-c]pyridine-5-sulfonic acid dimethyl amide,

[50] 6-(furan-2-carbonyl)-4,5,6,7-tetrahydro-isoxazolo[4,5-c]pyridine-3-carboxylic acid (thiophen-2-ylmethyl) amide,

[51] 5-(4,7,7-trimethyl-3-oxo-2-oxa-bicyclo[2.2.1]heptane-1-carbonyl)-4,5,6,7-tetrahydro-isoxazolo[4,5-c]pyridine-3-carboxylic acid (2-pyrrolidin-1-yl-ethyl) amide,

[52] 5-(2,5-dichloro-benzenesulfonyl)-4,5,6,7-tetrahydro-isoxazolo[4,5-c]pyridine-3-carboxylic acid [2-(2-chlorophenyl)-ethyl]amide,

[53] 5-(4-methoxy-benzenesulfonyl)-4,5,6,7-tetrahydro-isoxazolo[4,5-c]pyridine-3-carboxylic acid p-tolyl amide,

[54] 6-(2-phenoxy-acetyl)-4,5,6,7-tetrahydro-isoxazolo[4,5-c]pyridine-3-carboxylic acid 4-fluorobenzyl amide,

[55] 1-{4-[5-(4-methoxy-benzenesulfonyl)-4,5,6,7-tetrahydro-isoxazolo[4,5-c]pyridine-3-carbonyl]-piperazin-1-yl}-ethanone,

[56] 5-(toluene-4-sulfonyl)-4,5,6,7-tetrahydro-isoxazolo[4,5-c]pyridine-3-carboxylic acid 4-sulfamoyl-benzyl amide,

[57] 5-(thiophene-2-sulfonyl)-4,5,6,7-tetrahydro-isoxazolo[4,5-c]pyridine-3-carboxylic acid (2-morpholin-4-yl-ethyl) amide,

[58] 5-(4-methoxy-benzoyl)-4,5,6,7-tetrahydro-isoxazolo[4,5-c]pyridine-3-carboxylic acid (2-dimethylamino-ethyl) amide,

[59] 5(2,5-dichloro-benzenesulfonyl)-4,5,6,7-tetrahydro-isoxazolo[4,5-c]pyridine-3-carboxylic acid benzyl-phenethyl amide,

[60] 5-dimethylsulfamoyl-4,5,6,7-tetrahydro-isoxazolo[4,5-c]pyridine-3-carboxylic acid (2,6,6-trimethyl-bicyclo[3.1.1]hept-3-yl) amide,

[61] 5-benzenesulfonyl-4,5,6,7-tetrahydro-isoxazolo[4,5-c]pyridine-3-carboxylic acid indan-1-yl amide,

[62] 5-(4-methoxy-benzenesulfonyl)-4,5,6,7-tetrahydro-isoxazolo[4,5-c]pyridine-3-carboxylic acid (3-methoxy-propyl) amide,

[63] 5-(4,5-dichloro-thiophene-2-sulfonyl)-4,5,6,7-tetrahydro-isoxazolo[4,5-c]pyridine-3-carboxylic acid (2-morpholin-4-yl-ethyl) amide,

[64] 5-(2-benzyloxy-acetyl)-4,5,6,7-tetrahydro-isoxazolo[4,5-c]pyridine-3-carboxylic acid (2-pyrrolidin-1-yl-ethyl) amide,

[65] [5-(2,5-dichloro-benzenesulfonyl)-4,5,6,7-tetrahydro-isoxazolo[4,5-c]pyridin-3-yl]-[4-(2,4-dimethyl-phenyl)-piperazin-1-yl]-methanone,

[66] 5-pent-4-enoyl-4,5,6,7-tetrahydro-isoxazolo[4,5-c]pyridine-3-carboxylic acid cyclopropylmethyl amide,

[67] 3-methyl-2-{[5-(3-trifluoromethyl-benzenesulfonyl)-4,5,6,7-tetrahydro-isoxazolo[4,5-c]pyridine-3-carbonyl]-amino}-butanoic acid tert-butyl ester,

[68] 5-(3-trifluoromethyl-benzenesulfonyl)-4,5,6,7-tetrahydro-isoxazolo[4,5-c]pyridine-3-carboxylic acid benzyl-phenethyl amide,

[69] 5-(3-trifluoromethyl-benzenesulfonyl)-4,5,6,7-tetrahydro-isoxazolo[4,5-c]pyridine-3-carboxylic acid 2,4-dichloro-benzyl amide,

[70] 5-dimethylsulfamoyl-4,5,6,7-tetrahydro-isoxazolo[4,5-c]pyridine-3-carboxylic acid (2-cyano-ethyl)-pyridin-3-ylmethyl amide,

[71] 5-(2-cyclopentyl-acetyl)-4,5,6,7-tetrahydro-isoxazolo[4,5-c]pyridine-3-carboxylic acid (2-pyrrolidin-1-yl-ethyl) amide,

[72] 5-(5-methyl-2-phenyl-2H-[1,2,3]triazole-4-carbonyl)-4,5,6,7-tetrahydro-isoxazolo[4,5-c]pyridine-3-carboxylic acid 4-fluorobenzyl amide,

[73] 5-(3-trifluoromethyl-benzenesulfonyl)-4,5,6,7-tetrahydro-isoxazolo[4,5-c]pyridine-3-carboxylic acid (2-ethyl-hexyl)-amide,

[74] 5-(2,3-difluoro-4-methyl-benzoyl)-4,5,6,7-tetrahydro-isoxazolo[4,5-c]pyridine-3-carboxylic acid (2-dimethylamino-ethyl) amide,

[75] 5-(4-trifluoromethoxy-benzenesulfonyl)-4,5,6,7-tetrahydro-isoxazolo[4,5-c]pyridine-3-carboxylic acid 2,3-dichloro-benzyl amide,

[76] 5-dimethylsulfamoyl-4,5,6,7-tetrahydro-isoxazolo[4,5-c]pyridine-3-carboxylic acid [2-(4-chlorophenyl)-ethyl] amide,

[77] 5-(6-chloro-pyridine-3-carbonyl)-4,5,6,7-tetrahydro-isoxazolo[4,5-c]pyridine-3-carboxylic acid (2-pyrrolidin-1-yl-ethyl) amide,

[78] 5-[3-(4-fluoro-benzylcarbamoyl)-6,7-dihydro-4H-isoxazolo[4,5-c]pyridin-5-yl]-5-oxo-pentanoic acid methyl ester,

[79] 5-[2-(4-methoxyphenyl)-acetyl]-4,5,6,7-tetrahydro-isoxazolo[4,5-c]pyridine-3-carboxylic acid benzyl amide,

[80] 5-(4-trifluoromethoxy-benzenesulfonyl)-4,5,6,7-tetrahydro-isoxazolo[4,5-c]pyridine-3-carboxylic acid [3-(methylphenyl-amino)-propyl] amide,

[81] 5-[2-(4-chlorophenoxy)-acetyl]-4,5,6,7-tetrahydro-isoxazolo[4,5-c]pyridine-3-carboxylic acid cyclopentyl amide,

[82] [4-(2-cyclohexyl-ethyl)-piperazin-1-yl]-[5-(toluene-4-sulfonyl)-4,5,6,7-tetrahydro-isoxazolo[4,5-c]pyridin-3-yl]-methanone,

[83] N-{1-[5-(2,5-dichloro-benzenesulfonyl)-4,5,6,7-tetrahydro-isoxazolo[4,5-c]pyridine-3-carbonyl]-piperidin-4-ylmethyl}-2,2,2-trifluoroacetamide,

[84] 5-(4-methoxy-benzenesulfonyl)-4,5,6,7-tetrahydro-isoxazolo[4,5-c]pyridine-3-carboxylic acid [1-(4-methoxyphenyl)-ethyl]amide,

[85] 2-{[5-(thiophene-2-sulfonyl)-4,5,6,7-tetrahydro-isoxazolo[4,5-c]pyridine-3-carbonyl]-amino}-propionic acid ethyl ester,

[86] 1-(4-{4-[5-(toluene-4-sulfonyl)-4,5,6,7-tetrahydro-isoxazolo[4,5-c]pyridine-3-carbonyl]-piperazin-1-yl}-phenyl)-ethanone,

[87] 5-(3-trifluoromethyl-benzenesulfonyl-4,5,6,7-tetrahydro-isoxazolo[4,5-c]pyridine-3-carboxylic acid (4-allyloxy-benzyl)-furan-2-ylmethyl amide,

[88] 4-carbamoyl-4-{[5-(4-methoxy-benzenesulfonyl)-4,5,6,7-tetrahydro-isoxazolo[4,5-c]pyridine-3-carbonyl]-amino}-butanoic acid tert-butyl ester,

[89] 5-dimethylsulfamoyl-4,5,6,7-tetrahydro-isoxazolo[4,5-c]pyridine-3-carboxylic acid furan-2-ylmethyl-(4-methylsulfanyl-benzyl) amide,

[90] 5-(4-bromo-3-methyl-benzoyl)-4,5,6,7-tetrahydro-isoxazolo[4,5-c]pyridine-3-carboxylic acid (2-morpholin-4-yl-ethyl) amide,

[91] 5-(toluene-4-sulfonyl-4,5,6,7-tetrahydro-isoxazolo[4,5-c]pyridine-3-carboxylic acid [1-(2,6-dichloro-benzyl)-pyrrolidin-3-yl] amide,

[92] 5-benzenesulfonyl-4,5,6,7-tetrahydro-isoxazolo[4,5-c]pyridine-3-carboxylic acid [2-(3,4-dichloro-phenyl)-ethyl]amide,

[93] 5-(3-difluoromethylsulfanyl-benzoyl)-4,5,6,7-tetrahydro-isoxazolo[4,5-c]pyridine-3-carboxylic acid (2-dimethylamino-ethyl) amide,

[94] 5-[2-(3-chlorophenoxy)-acetyl]-4,5,6,7-tetrahydro-isoxazolo[4,5-c]pyridine-3-carboxylic acid (2-pyrrolidin-1-yl-ethyl) amide,

[95] 5-(4-methoxy-benzenesulfonyl)-4,5,6,7-tetrahydro-isoxazolo[4,5-c]pyridine-3-carboxylic acid 2,3-dimethoxy-benzyl amide,

[96] 5-(4-trifluoromethoxy-benzenesulfonyl)-4,5,6,7-tetrahydro-isoxazolo[4,5-c]pyridine-3-carboxylic acid (1-methyl-3-phenyl-propyl) amide,

[97] (5-benzenesulfonyl-4,5,6,7-tetrahydro-isoxazolo[4,5-c]pyridin-3-yl)-[4-(3-phenyl-allyl)-piperazin-1-yl]-methanone,

[98] 3-{[5-(4-methoxy-benzoyl)-4,5,6,7-tetrahydro-isoxazolo[4,5-c]pyridine-3-carbonyl]-amino}-propionic acid ethyl ester,

[99] 5-(4-phenoxy-butyryl)-4,5,6,7-tetrahydro-isoxazolo[4,5-c]pyridine-3-carboxylic acid (2-dimethylamino-ethyl)-amide,

[100] 5-(4-trifluoromethoxy-benzenesulfonyl)-4,5,6,7-tetrahydro-isoxazolo[4,5-c]pyridine-3-carboxylic acid [2-(7-methyl-1H-indol-3-yl)-ethyl] amide,

[101] [4-(3-phenyl-allyl)-piperazin-1-yl]-[6-(thiophene-2-sulfonyl)-4,5,6,7-tetrahydro-isoxazolo[4,5-c]pyridin-3-yl]-methanone,

[102] 5-(4-bromo-3-methyl-benzoyl)-4,5,6,7-tetrahydro-isoxazolo[4,5-c]pyridine-3-carboxylic acid (2-pyrrolidin-1-yl-ethyl) amide,

[103] 5-benzenesulfonyl-4,5,6,7-tetrahydro-isoxazolo[4,5-c]pyridine-3-carboxylic acid [1-(4-trifluoromethyl-benzyl)-pyrrolidin-3-yl] amide,

[104] 5-(thiophene-2-sulfonyl)-4,5,6,7-tetrahydro-isoxazolo[4,5-c]pyridine-3-carboxylic acid (2-phenyl-propyl) amide,

[105] 5-(3-chloro-4-fluoro-benzoyl)-4,5,6,7-tetrahydro-isoxazolo[4,5-c]pyridine-3-carboxylic acid phenethyl amide,

[106] 5-benzenesulfonyl-4,5,6,7-tetrahydro-isoxazolo[4,5-c]pyridine-3-carboxylic acid [2-(4-methoxy-phenoxy)-ethyl]amide,

[107] 5-dimethylsulfamoyl-4,5,6,7-tetrahydro-isoxazolo[4,5-c]pyridine-3-carboxylic acid 3-fluoro-4-trifluoromethyl-benzyl amide,

[108] 5-(3-methyl-benzoyl)-4,5,6,7-tetrahydro-isoxazolo[4,5-c]pyridine-3-carboxylic acid prop-2-ynyl amide,

[109] 5-(toluene-4-sulfonyl)-4,5,6,7-tetrahydro-isoxazolo[4,5-c]pyridine-3-carboxylic acid [2-(4-methoxy-phenoxy)-ethyl]amide,

[110] [4-(2-chlorophenyl)-piperazin-1-yl]-[5-(2,5-dichloro-benzenesulfonyl)-4,5,6,7-tetrahydro-isoxazolo[4,5-c]pyridin-3-yl]-methanone,

[111] 3-{[5-(2,6-difluoro-3-methyl-benzoyl)-4,5,6,7-tetrahydro-isoxazolo[4,5-c]pyridine-3-carbonyl]-amino}-propionic acid ethyl ester,

[112] 5-(2,5-dichloro-benzenesulfonyl)-4,5,6,7-tetrahydro-isoxazolo[4,5-c]pyridine-3-carboxylic acid 2,4-difluoro-benzyl amide,

[113] 5-benzenesulfonyl-4,5,6,7-tetrahydro-isoxazolo[4,5-c]pyridine-3-carboxylic acid 3-fluoro-4-trifluoromethyl-benzyl amide,

[114] 5-(4-butoxy-benzenesulfonyl)-4,5,6,7-tetrahydro-isoxazolo[4,5-c]pyridine-3-carboxylic acid isobutyl amide,

[115] 5-(3-fluoro-4-methyl-benzoyl)-4,5,6,7-tetrahydro-isoxazolo[4,5-c]pyridine-3-carboxylic acid (2-pyrrolidin-1-yl-ethyl) amide,

[116] 5-(2-chloro-5-trifluoromethyl-benzoyl)-4,5,6,7-tetrahydro-isoxazolo[4,5-c]pyridine-3-carboxylic acid isobutyl amide,

[117] 5-(4-trifluoromethoxy-benzenesulfonyl)-4,5,6,7-tetrahydro-isoxazolo[4,5-c]pyridine-3-carboxylic acid (1-benzyl-pyrrolidin-3-yl) amide,

[118] 5-(3-chloro-benzenesulfonyl)-4,5,6,7-tetrahydro-isoxazolo[4,5-c]pyridine-3-carboxylic acid (2-pyrrolidin-1-yl-ethyl) amide,

[119] 5-(3-trifluoromethoxy-benzoyl)-4,5,6,7-tetrahydro-isoxazolo[4,5-c]pyridine-3-carboxylic acid (2-dimethylamino-ethyl) amide,

[120] 2-{[5-(toluene-4-sulfonyl)-4,5,6,7-tetrahydro-isoxazolo[4,5-c]pyridine-3-carbonyl]-amino}-propionic acid tert-butyl ester,

[121] 3-{[5-(4-chloro-benzenesulfonyl)-4,5,6,7-tetrahydro-isoxazolo[4,5-c]pyridine-3-carbonyl]-amino}-propionic acid ethyl ester,

[122] 5-dimethylsulfamoyl-4,5,6,7-tetrahydro-isoxazolo[4,5-c]pyridine-3-carboxylic acid [2-(3,4-dichloro-phenyl)-ethyl]amide,

[123] 5-(thiophene-2-sulfonyl)-4,5,6,7-tetrahydro-isoxazolo[4,5-c]pyridine-3-carboxylic acid cyclopropylmethyl amide,

[124] 5-(quinoline-6-carbonyl)-4,5,6,7-tetrahydro-isoxazolo[4,5-c]pyridine-3-carboxylic acid 4-fluorobenzyl amide,

[125] 3-{[5-(2-naphthalen-2-yl-acetyl)-4,5,6,7-tetrahydro-isoxazolo[4,5-c]pyridine-3-carbonyl]-amino}-propionic acid ethyl ester,

[126] [2-(3-isobutylcarbamoyl-6,7-dihydro-4H-isoxazolo[4,5-c]pyridin-5-yl)-2-oxo-1-phenyl-ethyl]-carbamic acid benzyl ester,

[127] 5-(4-methoxy-benzylthiocarbamoyl)-4,5,6,7-tetrahydro-isoxazolo[4,5-c]pyridine-3-carboxylic acid cyclopentyl amide,

[128] 5-benzoylaminocarbothioyl-4,5,6,7-tetrahydro-isoxazolo[4,5-c]pyridine-3-carboxylic acid (2-pyrrolidin-1-yl-ethyl) amide,

[129] 5-(4-chloro-benzylthiocarbamoyl)-4,5,6,7-tetrahydro-isoxazolo[4,5-c]pyridine-3-carboxylic acid cyclopropyl-methyl amide,

[130] 5-(2-methoxy-ethylthiocarbamoyl)-4,5,6,7-tetrahydro-isoxazolo[4,5-c]pyridine-3-carboxylic acid phenethyl amide,

[131] 5-pentafluorophenylthiocarbamoyl-4,5,6,7-tetrahydro-isoxazolo[4,5-c]pyridine-3-carboxylic acid phenethyl amide,

[132] 5-(1-phenyl-ethylthiocarbamoyl)-4,5,6,7-tetrahydro-isoxazolo[4,5-c]pyridine-3-carboxylic acid phenethyl amide,

[133] 5-pentafluorophenylthiocarbamoyl-4,5,6,7-tetrahydro-isoxazolo[4,5-c]pyridine-3-carboxylic acid (5-methyl-furan-2-ylmethyl) amide,

[134] 3-{[5-(cyclohexylmethyl-thiocarbamoyl)-4,5,6,7-tetrahydro-isoxazolo[4,5-c]pyridine-3-carbonyl]-amino}-propionic acid ethyl ester,

[135] 5-(1-bromo-naphthalen-2-ylmethyl)-4,5,6,7-tetrahydro-isoxazolo[4,5-c]pyridine-3-carboxylic acid phenyl amide,
[136] $N^5$-(4-methoxyphenyl)-$N^3$-(4-sulfamoylbenzyl)-6,7-dihydroisoxazolo[4,5-c]pyridine-3,5(4H)-dicarboxamide,
[137] 5-(2-(3-chlorophenoxy)acetyl)-N-(2-(pyrrolidin-1-yl)ethyl)-4,5,6,7-tetrahydroisoxazolo[4,5-c]pyridino-3-carboxamide,
[138] 5-(2-fluorobenzoyl)-N-phenyl-4,5,6,7-tetrahydroisoxazolo[4,5-c]pyridine-3-carboxamide,
[139] N-(4-sulfamoylbenzyl)-5-tosyl-4,5,6,7-tetrahydroisoxazolo[4,5-c]pyridine-3-carboxamide,
[140] (5-(3,4-dichlorophenylsulfonyl)-4,5,6,7-tetrahydroisoxazolo[4,5-c]pyridin-3-yl)(4-(thiazol-2-yl)piperazin-1-yl)methanone,
[141] (5-(mesitylsulfonyl)-4,5,6,7-tetrahydroisoxazolo[4,5-c]pyridin-3-yl)(4-(thiazol-2-yl)piperazin-1-yl)methanone,
[142] (5-(naphthalen-1-ylsulfonyl)-4,5,6,7-tetrahydroisoxazolo[4,5-c]pyridin-3-yl)(4-(thiazol-2-yl)piperazin-1-yl)methanone,
[143] (5-(naphthalen-2-ylsulfonyl)-4,5,6,7-tetrahydroisoxazolo[4,5-c]pyridin-3-yl)(4-(thiazol-2-yl)piperazin-1-yl)methanone,
[144] (4-(3-(dimethylamino)propyl)piperazin-1-yl)(5-(mesitylsulfonyl)-4,5,6,7-tetrahydroisoxazolo[4,5-c]pyridin-3-yl)methanone dihydrochloride,
[145] (5-(3,4-dichlorophenylsulfonyl)-4,5,6,7-tetrahydroisoxazolo[4,5-c]pyridin-3-yl)(4-(3-(dimethylamino)propyl)piperazin-1-yl)methanone dihydrochloride,
[146] (5-(mesitylsulfonyl)-4,5,6,7-tetrahydroisoxazolo[4,5-c]pyridin-3-yl)(4-(2-(pyrrolidin-1-yl)ethyl)piperidin-1-yl)methanone,
[147] (5-(3,4-dichlorophenylsulfonyl)-4,5,6,7-tetrahydroisoxazolo[4,5-c]pyridin-3-yl)(4-(2-(pyrrolidin-1-yl)ethyl)piperidin-1-yl)methanone,
[148] (5-(naphthalen-2-ylsulfonyl)-4,5,6,7-tetrahydroisoxazolo[4,5-c]pyridin-3-yl)(4-(2-(pyrrolidin-1-yl)ethyl)piperidin-1-yl)methanone,
[149] (5-(naphthalen-1-ylsulfonyl)-4,5,6,7-tetrahydroisoxazolo[4,5-c]pyridin-3-yl)(4-(2-(pyrrolidin-1-yl)ethyl)piperidin-1-yl)methanone hydrochloride,
[150] $N^3$-benzyl-$N^5$-(1-phenylethyl)-6,7-dihydroisoxazolo[4,5-c]pyridine-3,5(4H)-dicarboxamide,
[151] $N^3$-benzyl-$N^5$-(4-methoxyphenyl)-6,7-dihydroisoxazolo[4,5-c]pyridine-3,5(4H)-dicarboxamide,
[152] N-p-tolyl-5-tosyl-4,5,6,7-tetrahydroisoxazolo[4,5-c]pyridine-3-carboxamide,
[153] 5-(3-fluoro-4-(trifluoromethyl)benzoyl)-N-(2-methoxyethyl)-4,5,6,7-tetrahydroisoxazolo[4,5-c]pyridine-3-carboxamide,
[154] $N^5$-(4-methoxyphenyl)-$N^3$-(4-sulfamoylbenzyl)-6,7-dihydroisoxazolo[4,5-c]pyridine-3,5(4H)-dicarboxamide,
[155] 5-(2-(3-chlorophenoxy)acetyl)-N-(2-(pyrrolidin-1-yl)ethyl)-4,5,6,7-tetrahydroisoxazolo[4,5-c]pyridine-3-carboxamide,
[156] 5-(2-fluorobenzoyl)-N-phenyl-4,5,6,7-tetrahydroisoxazolo[4,5-c]pyridine-3-carboxamide and
[157] N-(4-sulfamoylbenzyl)-5-tosyl-4,5,6,7-tetrahydroisoxazolo[4,5-c]pyridine-3-carboxamide,
in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The present invention also provides a method for producing compounds of the above-stated general formula I, in accordance with which at least one compound of the general formula II,

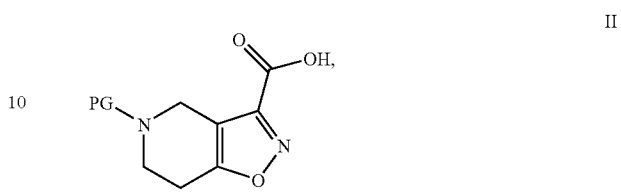

in which PG denotes a protective group, preferably a tert-butyloxycarbonyl or benzyloxycarbonyl group, is reacted in a reaction medium, in the presence of at least one coupling reagent, optionally in the presence of at least one base, preferably in the presence of at least one base selected from the group consisting of pyridine, N-methylmorpholine, diisopropylethylamine, triethylamine and 4,4-dimethylaminopyridine, with at least one amine of the general formula $HNR^1R^2$, in which the residues $R^1$ and $R^2$ have the above-stated meaning, to yield at least one compound of the general formula III,

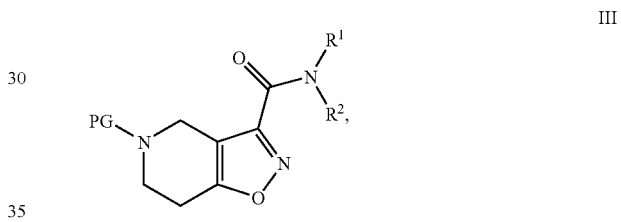

in which $R^1$, $R^2$ and PG have the above-stated meaning and said compound is optionally purified and/or isolated, and at least one compound of the general formula III is reacted by elimination of the protective group PG in a reaction medium, preferably by elimination in the presence of at least one acid or in the presence of at least one base for the tert-butyloxy-carbonyl group or in the presence of hydrogen and catalyst, preferably palladium on carbon for the benzyloxycarbonyl group, to yield at least one compound of the general formula IV, optionally in the form of a corresponding salt, preferably in the form of the corresponding hydrochloride,

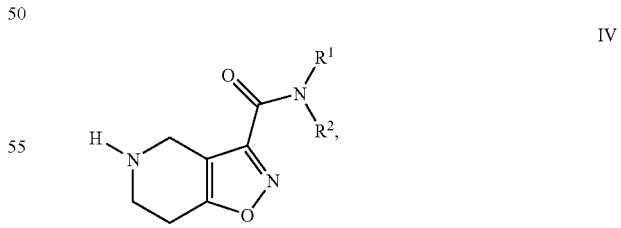

in which $R^1$ and $R^2$ have the above-stated meaning and said compound is optionally purified and/or isolated,
and
optionally at least one compound of the general formula IV in the form of a corresponding salt, preferably in the form of a corresponding hydrochloride, is reacted in a reaction medium in the presence of at least one base, preferably in the presence of at least one metal hydroxide, particularly preferably in the presence of potassium hydroxide and/or sodium hydroxide, to yield at least one compound of the general formula IV, and said compound is optionally purified and/or isolated,
and
at least one compound of the general formula IV is reacted in a reaction medium, optionally in the presence of at least one base, preferably in the presence of at least one base selected from the group consisting of pyridine, triethylamine, 4,4-dimethylaminopyridine, diisopropylethylamine and diisopropylamine, with at least one carboxylic acid derivative of the general formula LG-C(=O)—$R^{15}$, LG-C(=O)—$(CH_2)_j X_k$—$(CH_2)_m$—$(CH_2)_n$—C(=O)—$OR^{16}$, LG-C(=O)—$(CHR^{19})$—NH—C(=O)—$OR^{20}$, LG-C(=O)—$(CH_2)$—$(CH_2)_p(CH_2)_q Y_r$—$(CH_2)_s$—$R^{21}$ or LG-C(=O)—(CH=CH)—$R^{22}$, in which $R^{15}$, $R^{16}$, $R^{19}$, $R^{20}$, $R^{21}$, $R^{22}$, j, k, m, n, p, q, r, s, X and Y have the above-stated meaning and LG denotes a leaving group, preferably a halogen atom, particularly preferably a chlorine atom, to yield at least one compound of the general formula I, in which $R^1$ and $R^2$ have the above-stated meaning and $R^3$ denotes —C(=O)—$R^{15}$, —C(=O)—$(CH_2)_j X_k$—$(CH_2)_m$—$(CH_2)_n$—C(=O)—$OR^{16}$, —C(=O)—$(CHR^{19})$—NH—C(=O)—$R^{20}$, —C(=O)—$(CH_2)$—$(CH_2)_p$—$(CH_2)_q$—$Y_r$—$(CH_2)_s$—$R^{21}$ or —C(=O)—(CH=CH—)—$R^{22}$, wherein $R^{15}$, $R^{16}$, $R^{19}$, $R^{20}$, $R^{21}$, $R^{22}$, j, k, m, n, p, q, r, s, X and Y have the above-stated meaning, and said compound is optionally purified and/or isolated
or
at least one compound of the general formula IV is reacted in a reaction medium, in the presence of a coupling reagent, optionally in the presence of at least one base, preferably in the presence of at least one base selected from the group consisting of pyridine, N-methylmorpholine, diisopropylethylamine, triethylamine and 4,4-dimethylaminopyridine, with at least one carboxylic acid of the general formula HO—C(=O)—$R^{15}$, HO—C(=O)—$(CH_2)_j X_k$—$(CH_2)_m$—$(CH_2)_n$—C(=O)—$OR^{16}$, HO—C(=O)—$(CHR^{19})$—NH—C(=O)—$OR^{20}$, HO—C(=O)—$(CH_2)$—$(CH_2)_p(CH_2)_q Y_r$—$(CH_2)_s R^{21}$ or HO—C(=O)—(CH=CH)—$R^{22}$, in which $R^{15}$, $R^{16}$, $R^{19}$, $R^{20}$, $R^{21}$, $R^{22}$, j, k, m, n, p, q, r, s, X and Y have the above-stated meaning, to yield at least one compound of the general formula I, in which $R^1$ and $R^2$ have the above-stated meaning and $R^3$ denotes —C(=O)—$R^{15}$, —C(=O)—$(CH_2)_j X_k$—$(CH_2)_m$—$(CH_2)_n$—C(=O)—$OR^{16}$, —C(=O)—$(CHR^{19})$—NH—C(=O)—$OR^{20}$, —C(=O)—$(CH_2)$—$(CH_2)_p$—$(CH_2)_q$—$Y_r(CH_2)_s$—$R^{21}$ or —C(=O)—(CH=CH)—$R^{22}$, wherein $R^{15}$, $R^{16}$, $R^{19}$, $R^{20}$, $R^{21}$, $R^{22}$, j, k, m, n, p, q, r, s, X and Y have the above-stated meaning, and said compound is optionally purified and/or isolated
or
at least one compound of the general formula IV is reacted in a reaction medium, optionally in the presence of at least one base, preferably in the presence of at least one base selected from the group consisting of pyridine, triethylamine, 4,4-dimethylaminopyridine, diisopropylethylamine and diisopropylamine, with at least one sulfonic acid derivative of the general formula LG-S(=O)$_2$—$R^{23}$ or LG-S(=O)$_2$—$NR^{24}R^{25}$, in which $R^{23}$, $R^{24}$ and $R^{25}$ have the above-stated meaning and LG denotes a leaving group, preferably a halogen atom, particularly preferably a chlorine atom, to yield at least one compound of the general formula I, in which $R^1$ and $R^2$ have the above-stated meaning and $R^3$ denotes —S(=O)$_2$—$R^{23}$ or —S(=O)$_2$—$NR^{24}R^{25}$, wherein $R^{23}$, $R^{24}$ and $R^{25}$ have the above-stated meaning, and said compound is optionally purified and/or isolated
or
at least one compound of the general formula IV is reacted in a reaction medium with at least one isocyanate of the general formula $R^{14}$—N=C=O, in which $R^{14}$ has the above-stated meaning, optionally in the presence of at least one base, preferably in the presence of at least one base selected from the group consisting of triethylamine, 4,4-dimethylaminopyridine and diisopropylethylamine, to yield at least one compound of the general formula I, in which $R^1$ and $R^2$ have the above-stated meaning and $R^3$ denotes —C(=O)—$NR^{13}R^{14}$, wherein $R^{14}$ has the above-stated meaning and $R^{13}$ denotes hydrogen, and said compound is optionally purified and/or isolated
or
at least one compound of the general formula IV is reacted in a reaction medium with at least one isothiocyanate of the general formula S=C=N—$(CH_2)_t(CH_2)_u$—$Z_v R^{27}$, S=C=N—$(CHR^{28})$—$R^{29}$ or S=C=N—C(=O)—$R^{30}$, in which $R^{27}$, $R^{28}$, $R^{29}$, $R^{30}$, Z, t, u and v have the above-stated meaning, optionally in the presence of at least one base, preferably in the presence of at least one base selected from the group consisting of triethylamine, 4,4-dimethylaminopyridine and diisopropylethylamine, to yield at least one compound of the general formula I, in which $R^1$ and $R^2$ have the above-stated meaning and $R^3$ denotes —C(=S)—$NR^{26}$—$(CH_2)_t(CH_2)_u$—$Z_v$—$R^{27}$, —C(=S)—$NR^{26}$—$(CHR^{28})$—$R^{29}$ or —C(=S)—$NR^{26}$—C(=O)—$R^{30}$, wherein $R^{27}$, $R^{28}$, $R^{29}$, $R^{30}$, Z, t, u and v have the above-stated meaning and $R^{26}$ denotes hydrogen, and said compound is optionally purified and/or isolated
and optionally at least one compound of the general formula I, in which $R^1$ and $R^2$ have the above-stated meaning and $R^3$ denotes —C(=S)—$NR^{26}$—$(CH_2)_t$—$(CH_2)_u$—$Z_v$—$R^{27}$, —C(=S)—$NR^{26}$—$(CHR^{28})$—$R^{29}$, —C(=S)—$NR^{26}$—C(=O)—$R^{30}$ or —C(=O)—$NR^{13}R^{14}$ wherein $R^{14}$, $R^{27}$, $R^{28}$, $R^{29}$, $R^{30}$, Z, t, u and v have the above-stated meaning and $R^{13}$ and $R^{26}$ denote hydrogen, is reacted in a reaction medium, optionally in the presence of at least one base, preferably in the presence of at least one metal hydride salt, particularly preferably in the presence of sodium hydride and/or potassium hydride, with at least one compound of the general formula LG-$R^{13}$ or LG-$R^{26}$, in which $R^{13}$ and $R^{26}$ have the above-stated meaning with the exception of a hydrogen residue and LG denotes a leaving group, preferably a halogen atom, particularly preferably a chlorine atom, to yield at least one compound of the general formula I, in which $R^1$ and $R^2$ have the above-stated meaning and $R^3$ denotes —C(=S)—$NR^{26}$—$(CH_2)_t$—$(CH_2)_u$—$Z_v$—$R^{27}$, —C(=S)—$NR^{26}$—$(CHR^{28})$—$R^{29}$, —C(=S)—$NR^{26}$—C(=O)—$R^{30}$ or —C(=O)—$NR^{13}R^{14}$ wherein $R^{13}$, $R^{26}$, $R^{14}$, $R^{27}$, $R^{28}$, $R^{29}$, $R^{30}$, Z, t, u and v have the above-stated meaning, and said compound is optionally purified and/or isolated
or
at least one compound of the general formula IV is reacted in a reaction medium, optionally in the presence of at least one base, preferably in the presence of at least one metal hydride salt, particularly preferably in the presence of sodium hydride and/or potassium hydride, with at least one compound of the general formula LG-$(CH_2)$—$R^{31}$, in which $R^{31}$ has the above-stated meaning and LG denotes a leaving group, preferably a halogen atom, particularly preferably a chlorine atom, to yield at least one compound of the general formula I, in which $R^1$ and $R^2$ have the above-stated meaning and $R^3$ denotes —$(CH_2)$—$R^{31}$, wherein $R^{31}$ has the above-stated meaning, and said compound is optionally purified and/or isolated
or at least one compound of the general formula IV is reacted in a reaction medium, in the presence of at least one reducing agent, with at least one compound of the general formula $R^{31}$—C(=O)—H, in which $R^{31}$ has the above-stated meaning, to yield at least one compound of the general formula I, in which $R^1$ and $R^2$ have the above-stated meaning and $R^3$ denotes —(CH₂)—R³¹, wherein R³¹ has the above-stated meaning, and said compound is optionally purified and/or isolated.

The method according to the invention for producing substituted 4,5,6,7-tetrahydro-isoxazolo[4,5-c]pyridine compounds of the above-stated general formula I is also shown in Scheme 1 below.

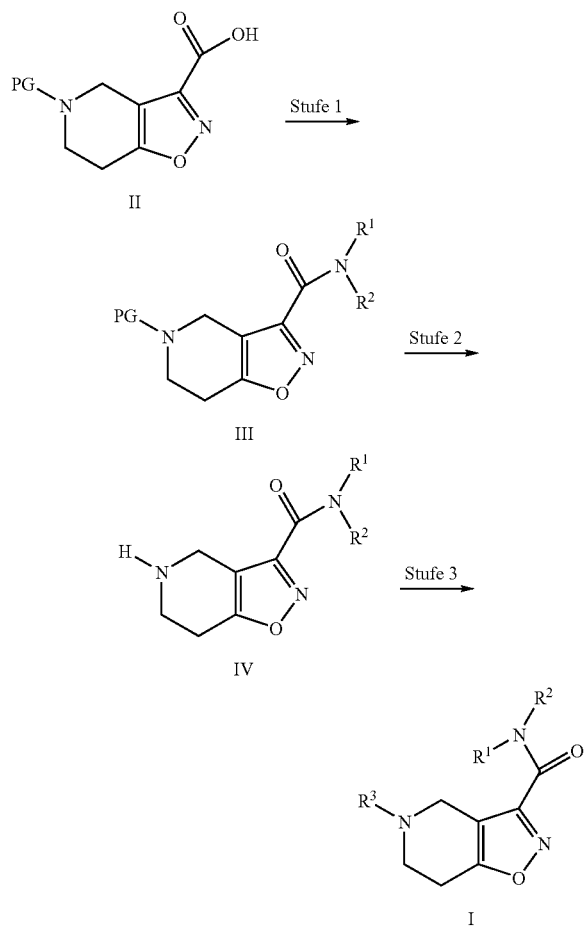

[Key: Stufe = stage]

In stage 1, compounds of the above-stated general formula II are reacted with amines of the general formula HNR¹R², in which R¹ and R² have the above-stated meaning, in a reaction medium, preferably selected from the group consisting of diethyl ether, tetrahydrofuran, acetonitrile, methanol, ethanol, dimethylformamide and dichloromethane or corresponding mixtures, optionally in the presence of at least one coupling reagent preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), N-[(dimethylamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU) and 1-hydroxy-7-azabenzotriazole (HOAt), optionally in the presence of at least one inorganic base, preferably selected from the group consisting of potassium carbonate and caesium carbonate, or an organic base, preferably selected from the group consisting of triethylamine, pyridine, N-methylmorpholine, 4,4-dimethylaminopyridine and diisopropylethylamine preferably at temperatures of preferably −70° C. to 100° C. to yield compounds of the general formula III.

In stage 2, compounds of the general formula III, in which PG denotes a tert-butyloxy-carbonyl group, are reacted in a reaction medium preferably selected from the group consisting of methanol, ethanol, isopropanol, water, diethyl ether, tetrahydrofuran and corresponding mixtures in the presence of at least one acid preferably selected from the group consisting of hydrochloric acid, sulfuric acid, trifluoroacetic acid and acetic acid at temperatures of preferably 20 to 30° C. to yield compounds of the general formula IV. The reaction of the compound of the general formula III particularly preferably proceeds in a 4 M hydrochloric acid solution in methanol at a temperature of preferably 20 to 30° C. to yield a compound of the general formula IV in the form of a corresponding hydrochloride.

Alternatively, compounds of the general formula III, in which PG denotes a benzyloxycarbonyl group, are reacted in a reaction medium preferably selected from the group consisting of diethyl ether, tetrahydrofuran, dioxane, acetonitrile, toluene and corresponding mixtures in the presence of hydrogen and palladium on carbon at a temperature of preferably 20 to 80° C. to yield a compound of the general formula IV. If compounds of the general formula IV are present in the form of a corresponding hydrochloride, they are converted in a reaction medium preferably selected from the group consisting of dioxane, tetrahydrofuran, diethyl ether, methanol, ethanol, isopropanol, water and corresponding mixtures, in the presence of an inorganic base, preferably with addition of a metal hydroxide, for example sodium hydroxide, potassium hydroxide or lithium hydroxide, at temperatures of preferably 0° C. to 30° C. into the corresponding bases of the general formula IV.

In stage 3, compounds of the general formula IV are reacted with carboxylic acid derivatives of the general formula LG-C(=O)—R¹⁵, LG-C(=O)—(CH₂)ⱼXₖ—(CH₂)ₘ—(CH₂)ₙ—C(=O)—OR¹⁶, LG-C(=O)—(CHR¹⁹)—NH—C(=O)—OR²⁰, LG-C(=O)—(CH₂)—(CH₂)ₚ—(CH₂)_q—Y_r—(CH₂)_s—R²¹ or LG-C(=O)—(CH=CH)—R²², in which R¹⁵, R¹⁶, R¹⁹, R²⁰, R²¹, R²², j, k, m, n, p, q, r, s, X and Y has the above-stated meaning have and LG denotes a leaving group, preferably a halogen atom, particularly preferably a chlorine atom, in a reaction medium, preferably selected from the group consisting of diethyl ether, tetrahydrofuran, acetonitrile, methanol, ethanol, dimethylformamide, dichloromethane and corresponding mixtures, optionally in the presence of an organic base, preferably selected from the group consisting of triethylamine, 4,4-dimethylaminopyridine, pyridine and diisopropylethylamine, or an inorganic base, at temperatures of preferably −70° C. to 100° C. to yield compounds of the general formula I, in which R³ denotes —C(=O)—R¹⁵, —C(=O)—(CH₂)ⱼXₖ—(CH₂)ₘ—(CH₂)ₙ—C(=O)—OR¹⁶, —C(=O)—(CHR¹⁹)—NH—C(=O)—OR²⁰, —C(=O)—(CH₂)—(CH₂)ₚ—(CH₂)_q—Y_r—(CH₂)_s—R²¹ or —C(=O)—(CH=CH)—R²².

Alternatively, compounds of the above-stated general formula IV are reacted with carboxylic acids of the general formula OH—C(=O)—R¹⁵, OH—C(=O)—(CH₂)ⱼXₖ—(CH₂)ₘ—(CH₂)ₙ—C(=O)—OR¹⁶, OH—C(=O)—(CHR¹⁹)—NH—C(=O)—OR²⁰, OH—C(=O)—(CH₂)—(CH₂)ₚ—(CH₂)_q—Y_r—(CH₂)_s—R²¹ or OH—C(=O)—(CH=CH)—R²², in which R¹⁵, R¹⁶, R¹⁹, R²⁰, R²¹, R²², j, k, m, n, p, q, r, s, X and Y have the above-stated meaning, in a reaction medium, preferably selected from the group consisting of diethyl ether, tetrahydrofuran, acetonitrile, methanol, ethanol, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), N-[(dimethylamino)-1°H.-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU) and 1-hydroxy-7-azabenzotriazole (HOAt), optionally in the presence of at least one inorganic base, preferably selected from the group consisting of potassium carbonate and caesium carbonate, or an organic base, preferably selected from the group consisting of triethylamine, pyridine, N-methylmorpholine, 4,4-dimethylaminopyridine and diisopropylethylamine preferably at temperatures of preferably −70° C. to 100° C. to yield compounds of the general formula I, in which $R^3$ denotes —C(=O)—$R^{15}$, —C(=O)—$(CH_2)_j$—$X_k$—$(CH_2)_m$—$(CH_2)_n$—C(=O)—$OR^{16}$, —C(=O)—$(CHR^{19})$—NH—C(=O)—$OR^{20}$, —C(=O)$(CH_2)$—$(CH_2)_p$—$(CH_2)_q$—$Y_r(CH_2)_s$—$R^{21}$ or —C(=O)—(CH=CH)—$R^{22}$.

Compounds of the general formula IV may likewise be reacted with sulfonic acid derivatives of the general formula LG-S(=O)$_2$—$R^{23}$ or LG-S(=O)$_2$—$NR^{24}R^{25}$, in which $R^{23}$, $R^{24}$ and $R^{25}$ have the above-stated meaning and LG denotes a leaving group, preferably a halogen atom, particularly preferably a chlorine atom, in a reaction medium, preferably selected from the group consisting of diethyl ether, tetrahydrofuran, acetonitrile, methanol, ethanol, dimethylformamide, dichloromethane and corresponding mixtures, optionally in the presence of an organic base, preferably selected from the group consisting of triethylamine, 4,4-dimethylaminopyridine, pyridine and diisopropylethylamine, or an inorganic base, at temperatures of preferably −70° C. to 100° C. to yield compounds of the general formula I, in which $R^3$ denotes —S(=O)$_2$—$R^{23}$ or —S(=O)$_2$—$NR^{24}R^{25}$.

Alternatively, compounds of the general formula IV are reacted with an isocyanate of the general formula $R^{14}$—N=C=O, in which $R^{14}$ has the above-stated meaning, in a reaction medium, preferably selected from the group consisting of acetonitrile, toluene, benzene, ethanol, methanol, water and corresponding mixtures, optionally in the presence of at least one base, preferably in the presence of at least one base selected from the group consisting of triethylamine, N-methylmorpholine, pyridine, 4,4-dimethylaminopyridine and diisopropylethylamine, to yield compounds of the general formula I, in which $R^3$ denotes —C(=O)—$NR^{13}R^{14}$.

Alternatively, in stage 3, compounds of the general formula IV are reacted with isothiocyanates of the general formula S=C=N—$(CH_2)_t(CH_2)_u$—$Z_v$—$R^{27}$, S=C=N—$(CHR^{28})$—$R^{29}$ or S=C=N—C(=O)—$R^{30}$, in which $R^{27}$, $R^{28}$, $R^{29}$, $R^{30}$, Z, t, u and v have the above-stated meaning, in a reaction medium, preferably selected from the group consisting of acetonitrile, toluene, benzene, ethanol, methanol, water and corresponding mixtures, optionally in the presence of at least one base, preferably in the presence of at least one base selected from the group consisting of triethylamine, 4,4-dimethylaminopyridine, pyridine, N-methylmorpholine and diisopropylethylamine, to yield compounds of the general formula I, in which $R^3$ denotes —C(=S)—$NR^{26}$—$(CH_2)_t(CH_2)_u$—$Z_v$—$R^{27}$, —C(=S)—$NR^{26}$—$(CHR^{28})$—$R^{29}$ or —C(=S)—$NR^{26}C(=O)$—$R^{30}$.

Likewise in stage 3, compounds of the general formula IV are reacted with compounds of the general formula LG-$(CH_2)$—$R^{31}$, in which $R^{31}$ has the above-stated meaning and LG denotes a leaving group, preferably a halogen atom, particularly preferably a chlorine atom, in a reaction medium, preferably selected from the group consisting of dichloromethane, toluene, tetrahydrofuran, acetonitrile, diethyl ether, dioxane and corresponding mixtures optionally in the presence of at least one base, preferably in the presence of at least one metal hydride salt, particularly preferably in the presence of sodium hydride and/or potassium hydride, to yield compounds of the general formula I, in which $R^3$ denotes —$(CH_2)$—$R^{31}$.

Alternatively, in stage 3, compounds of the general formula IV are reacted with compounds of the general formula $R^{31}$—C(=O)—H, in which $R^{31}$ has the above-stated meaning, in a reaction medium, preferably selected from the group consisting of diethyl ether, tetrahydrofuran, methanol, ethanol, dichloromethane, toluene and corresponding mixtures, with addition of at least one reducing agent, preferably with addition of at least one reducing agent selected from the group consisting of sodium borohydride, sodium acetoxyborohydride, sodium cyanoborohydride and borane-pyridine complex (pyridine-borane, $BH_3 \cdot C_5H_5N$), particularly preferably in the presence of borane-pyridine complex, to yield compounds of the general formula I, in which $R^3$ denotes —$(CH_2)$—$R^{31}$.

The compounds of the general formula II may be preferably be obtained as described in Scheme 2.

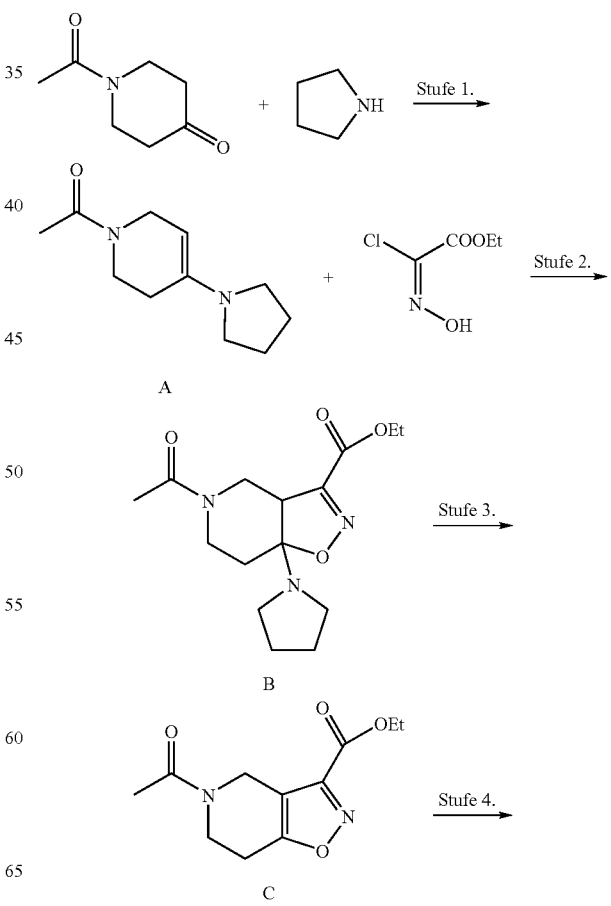

Scheme 2.

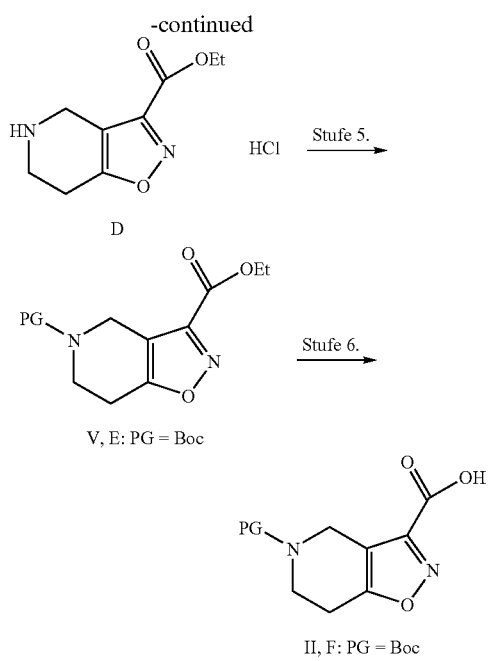

[Key: Stufe = stage]

In stage 1, the compound 1-acetyl-4-piperidinone is reacted in a reaction medium, preferably selected from the group consisting of toluene and benzene, with pyrrolidine in the presence of a catalytic quantity of an acid, preferably in the presence of p-toluenesulfonic acid, with refluxing on a water separator to yield the compound 1-(4-pyrrolidin-1-yl-3,6-dihydro-2H-pyridin-1-yl)-ethanone (A).

In stage 2, 1-(4-pyrrolidin-1-yl-3,6-dihydro-2H-pyridin-1-yl)-ethanone (A) is reacted with 2-chlorohydroxyiminoacetic acid ethyl ester in a reaction medium, preferably selected from the group consisting of acetonitrile, dichloromethane, chloroform, dimethylformamide, dimethylacetamide, dimethyl sulfoxide and corresponding mixtures, in the presence of at least one base, preferably selected from the group consisting of triethylamine, pyridine, 4,4-dimethylaminopyridine, N-methylmorpholine and diisopropylethylamine, at a temperature of preferably 0 to 30° C. to yield the compound 5-acetyl-7° a.-pyrrolidin-1-yl-3° a.,4,5,6,7,7a-hexahydro-isoxazolo[4,5-c]pyridine-3-carboxylic acid ethyl ester (B).

In stage 3, 5-acetyl-7° a.-pyrrolidin-1-yl-3a,4,5,6,7,7a-hexahydro-isoxazolo[4,5-c]pyridine-3-carboxylic acid ethyl ester (B) is reacted in a reaction medium, preferably selected from the group consisting of acetonitrile, dichloromethane, chloroform, dimethylformamide, dimethylacetamide, dimethyl sulfoxide and corresponding mixtures, in the presence of an organic acid, preferably in the presence of trifluoroacetic acid, with refluxing to yield the compound 5-acetyl-4,5,6,7-tetrahydro-isoxazolo[4,5-c]pyridine-3-carboxylic acid ethyl ester (C).

In stage 4, the compound 5-acetyl-4,5,6,7-tetrahydro-isoxazolo[4,5-c]pyridine-3-carboxylic acid ethyl ester (C) is reacted in a reaction medium, preferably selected from the group consisting of methanol, ethanol, isopropanol, tetrahydrofuran, water and corresponding mixtures, in the presence of an inorganic acid, preferably in the presence of hydrochloric acid and/or sulfuric acid with refluxing to yield the compound 4,5,6,7-tetrahydro-isoxazolo[4,5-c]pyridine-3-carboxylic acid ethyl ester hydrochloride (D) in the form of the corresponding hydrochloride.

In stage 5, the compound 4,5,6,7-tetrahydro-isoxazolo[4,5-c]pyridine-3-carboxylic acid ethyl ester hydrochloride (D) is reacted in a reaction medium, preferably selected from the group consisting of dioxane, ethanol, methanol, isopropanol, water and corresponding mixtures, in the presence of at least one organic base, preferably selected from the group consisting of triethylamine, diisopropylethylamine, pyridine, 4,4-dimethylaminopyridine and N-methylmorpholine, with a protective group-transferring reagent, preferably with a reagent selected from the group consisting of di-tert-butyl dicarbonate [(Boc)$_2$O] and benzyl chloroformate, at 0° C. and then at 20 to 30° C. to yield a compound of the general formula V (with PG=Boc: 6,7-dihydro-4H-isoxazolo[4,5-c]pyridine-3,5-dicarboxylic acid 3-ethyl ester 5-tert-butyl ester (E)). A dioxane/water mixture (2:1) is preferably used as the reaction medium.

In stage 6, a compound of the general formula V is reacted in a reaction medium, preferably selected from the group consisting of methanol, ethanol, isopropanol, water and corresponding mixtures, with an inorganic base, preferably with a base selected from the group consisting of lithium hydroxide, potassium hydroxide and sodium hydroxide at a temperature of preferably 20 to 30° C. to yield a compound of the general formula II (PG=Boc: 6,7-dihydro-4H-isoxazolo[4,5-c]pyridine-3,5-dicarboxylic acid 5-tert-butyl ester (F)).

The compounds of the above-stated general formulae LG-C(=O)—R$^{15}$, LG-C(=O)—(CH$_2$)$_j$—X$_k$—(CH$_2$)$_m$—(CH$_2$)$_n$—C(=O)—OR$^{16}$, LG-C(=O)—(CHR$^{19}$)—NH—C(=O)—OR$^{20}$, LG-C(=O)—(CH$_2$)—(CH$_2$)$_p$—(CH$_2$)$_q$—Y$_r$—(CH$_2$)$_s$—R$^{21}$, LG-C(=O)—(CH=CH)—R$^{22}$, —NH—C(=O)—OR$^{20}$, —C(=O)—(CH$_2$)—(CH$_2$)$_p$—(CH$_2$)$_q$—Y$_r$—(CH$_2$)$_s$—R$^{21}$, —C(=O)—(CH=CH)—R$^{22}$, OH—C(=O)—R$^{15}$, OH—C(=O)—(CH$_2$)$_j$X$_k$—(CH$_2$)$_m$—(CH$_2$)$_n$—C(=O)—OR$^{16}$, OH—C(=O)—(CHR$^{19}$)—NH—C(=O)—OR$^{20}$, OH—C(=O)—(CH$_2$)—(CH$_2$)$_p$—(CH$_2$)$_q$—Y$_r$—(CH$_2$)$_s$—R$^{21}$, OH—C(=O)—(CH=CH)—R$^{22}$, LG-R$^{13}$, LG-R$^{26}$, LG-S(=O)$_2$—R$^{23}$, LG-S(=O)$_2$—NR$^{24}$R$^{25}$, R$^{14}$—N=C=O, S=C=N—(CH$_2$)$_t$—(CH$_2$)$_u$—Z$_v$—R$^{27}$, S=C=N—(CHR$^{28}$)—R$^{29}$, S=C=N—C(=O)—R$^{30}$ and LG-(CH$_2$)—R$^{31}$ are in each case commercially available and/or may be produced using conventional methods known to a person skilled in the art.

The above-described reactions may in each case be performed under conventional conditions familiar to the person skilled in the art, for example with regard to pressure or the sequence of addition of the components. Optimum control of the process under the respective conditions may optionally be established by a person skilled in the art by simple preliminary testing.

The intermediate and final products obtained from the above-described reactions may in each case, if desired and/or necessary, be purified and/or isolated using conventional methods known to a person skilled in the art. Suitable purification methods are, for example, extraction methods and chromatographic methods such as column chromatography or preparative chromatography.

All the above-described process steps and in each case also the purification and/or isolation of intermediate or final products may be performed in part or entirely under an inert gas atmosphere, preferably under a nitrogen atmosphere.

The substituted 4,5,6,7-tetrahydro-isoxazolo[4,5-c]pyridine compounds according to the invention of the above-stated general formula I and corresponding stereoisomers may be isolated not only in the form of the free bases or free acids thereof, but also in the form of corresponding salts, in particular physiologically acceptable salts.

The free bases of the particular substituted 4,5,6,7-tetrahydro-isoxazolo[4,5-c]pyridine compounds according to the invention of the above-stated general formula I and corresponding stereoisomers may, for example, be converted into the corresponding salts, preferably physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid.

The free bases of the respective substituted 4,5,6,7-tetrahydro-isoxazolo[4,5-c]pyridine compounds of the above-stated general formula I and corresponding stereoisomers may likewise be converted into the corresponding physiologically acceptable salts with the free acid or a salt of a sugar substitute, such as for example saccharin, cyclamate or acesulfame.

The free acids of the substituted 4,5,6,7-tetrahydro-isoxazolo[4,5-c]pyridine compounds of the above-stated general formula I and corresponding stereoisomers may correspondingly be converted into the corresponding physiologically acceptable salts by reaction with a suitable base. Examples which may be mentioned are alkali metal salts, alkaline earth metal salts or ammonium salts $NH_xR_{4-x}]^+$, in which x=0, 1, 2, 3 or 4 and R denotes a linear or branched residue.

The substituted 4,5,6,7-tetrahydro-isoxazolo[4,5-c]pyridine compounds according to the invention of the above-stated general formula I and corresponding stereoisomers may optionally, like the corresponding acids, the corresponding bases or salts of this compounds, also be obtained in the form of the solvates thereof, preferably in the form the hydrates thereof, using conventional methods known to the person skilled in the art.

If the substituted 4,5,6,7-tetrahydro-isoxazolo[4,5-c]pyridine compounds according to the invention of the above-stated general formula I are obtained after the production thereof in the form of a mixture of the stereoisomers thereof, preferably in the form of the racemates thereof or other mixtures of their various enantiomers and/or diastereomers, these may be separated and optionally isolated by conventional methods known to the person skilled in the art. Examples which may be mentioned are chromatographic separation processes, in particular liquid chromatography processes at standard pressure or at elevated pressure, preferably MPLC and HPLC processes, and fractional crystallisation processes. Individual enantiomers, for example diastereomeric salts formed by means of HPLC on a chiral stationary phase or by means of crystallisation with chiral acids, such as (+)-tartaric acid, (−)-tartaric acid or (+)-10-camphorsulfonic acid, may here in particular be separated from one another.

The substituted 4,5,6,7-tetrahydro-isoxazolo[4,5-c]pyridine compounds according to the invention of the above-stated general formula I and corresponding stereoisomers as well as in each case the corresponding acids, bases, salts and solvates are toxicologically safe and are therefore suitable as pharmaceutical active ingredients in medicaments.

The present invention accordingly also provides a medicament containing at least one 4,5,6,7-tetrahydro-isoxazolo[4,5-c]pyridine compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

The medicament according to the invention is suitable for noradrenalin receptor regulation, in particular for inhibiting noradrenalin reuptake (noradrenalin uptake), for 5-HT receptor regulation, in particular for inhibiting 5-hydroxy-tryptophan reuptake (5-HT uptake) and/or for batrachotoxin (BTX) receptor regulation.

The medicament according to the invention is preferably suitable for the prevention and/or treatment of disorders and/or diseases, which are mediated at least in part by noradrenalin receptors, 5-HT receptors and/or batrachotoxin receptors.

The medicament according to the invention is therefore preferably for the prevention and/or treatment of pain, preferably of pain selected from the group consisting of acute pain, chronic pain and neuropathic pain, for the prevention and/or treatment of one or more diseases selected from the group consisting of migraine; depression; inflammation; lack of drive; urinary incontinence; neurodegenerative diseases, preferably selected from the group consisting of Parkinson's disease, Huntington's chorea, Alzheimer's disease and multiple sclerosis; disorders of food intake, preferably selected from the group consisting of bulimia, anorexia, obesity and cachexia; anxiety states; cognitive dysfunction, preferably memory disorders; cognitive deficiency states (attention deficit syndrome, ADS); epilepsy; catalepsy; diarrhoea and pruritus; for anxiolysis, for the prevention and/or treatment of the abuse of alcohol and/or drugs and/or medicines and dependency on alcohol and/or drugs and/or medicines, preferably for prevention and/or reduction of withdrawal symptoms associated with dependency on alcohol and/or drugs and/or medicines; for regulating food intake; for modulating locomotor activity; for regulating the cardiovascular system; for local anaesthesia; for increasing vigilance; for increasing libido; for diuresis; for antinatriuresis; for use as a local anaesthetic and/or antiarrhythmic and/or antiemetic and/or nootropic (neurotropic).

The medicament according to the invention is very particularly preferably suitable for the treatment and/or prevention of one or more diseases selected from the group consisting of pain, preferably of pain selected from the group consisting of acute pain, chronic pain and neuropathic pain, depression and anxiety states.

The present invention also provides the use of at least one 4,5,6,7-tetrahydro-isoxazolo[4,5-c]pyridine derivative according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a medicament for the noradrenalin receptor regulation, in particular for inhibiting noradrenalin reuptake (NA uptake), for 5-HT receptor regulation, in particular for inhibiting 5-hydroxy-tryptophan reuptake (5-HT uptake) and/or for batrachotoxin (BTX) receptor regulation.

It is preferred to use at least one substituted 4,5,6,7-tetrahydro-isoxazolo[4,5-c]pyridine derivative of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a medicament for the prevention and/or treatment of disorders and/or diseases which are mediated at least in part by noradrenalin receptors, 5-HT receptors and/or batrachotoxin receptors.

Is particularly preferred to use at least one substituted 4,5,6,7-tetrahydro-isoxazolo[4,5-c]pyridine derivative of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for producing a medicament for the treatment and/or prevention of pain, preferably of pain selected from the group consisting of acute pain, chronic pain and neuropathic pain, for the prevention and/or treatment of one or more diseases selected from the group consisting of migraine; depression; inflammation; lack of drive; urinary incontinence; neurodegenerative diseases, preferably selected from the group consisting of Parkinson's disease, Huntington's chorea, Alzheimer's disease and multiple sclerosis; disorders of food intake, preferably selected from the group consisting of bulimia, anorexia, obesity and cachexia; anxiety states; cognitive dysfunction, preferably memory disorders; cognitive deficiency states (attention deficit syndrome, ADS); epilepsy; catalepsy; diarrhoea and pruritus; for the prevention and/or treatment of the abuse of alcohol and/or drugs and/or medicines and dependency on alcohol and/or drugs and/or medicines, preferably for the prevention and/or reduction of withdrawal symptoms associated with dependency on alcohol and/or drugs and/or medicines; for regulating food intake; for modulating locomotor activity; for regulating the cardiovascular system; for local anaesthesia; for increasing vigilance; for increasing libido; for diuresis; for antinatriuresis; for use as a local anaesthetic and/or antiarrhythmic and/or antiemetic and/or nootropic (neurotropic).

It is very particularly preferred to use at least one substituted 4,5,6,7-tetrahydro-isoxazolo[4,5-c]pyridine derivative of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a medicament for the treatment and/or prevention of pain, preferably pain selected from the group consisting of acute pain, chronic pain and neuropathic pain, for the prevention and/or treatment of one or more diseases selected from the group consisting of migraine; depression; inflammation; lack of drive; urinary incontinence; neurodegenerative diseases, preferably selected from the group consisting of Parkinson's disease, Huntington's chorea, Alzheimer's disease and multiple sclerosis; disorders of food intake, preferably selected from the group consisting of bulimia, anorexia, obesity and cachexia; anxiety states; cognitive dysfunction, preferably memory disorders; cognitive deficiency states (attention deficit syndrome, ADS); epilepsy and for the prevention and/or treatment of the abuse of alcohol and/or drugs and/or medicines and dependency on alcohol and/or drugs and/or medicines, preferably for prevention and/or reduction of withdrawal symptoms associated with dependency on alcohol and/or drugs and/or medicines.

It is very particularly preferred to use at least one substituted 4,5,6,7-tetrahydro-isoxazolo[4,5-c]pyridine derivative of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a medicament for the treatment and/or prevention of pain, preferably pain selected from the group consisting of acute pain, chronic pain and neuropathic pain, depression and anxiety states.

The medicament according to the invention is suitable for administration to adults and children including small children and babies.

The medicament according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted 4,5,6,7-tetrahydro-isoxazolo[4,5-c]pyridine derivative of the above-stated general formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the medicament according to the invention conventionally contains further physiologically acceptable pharmaceutical auxiliary substances, which may preferably be selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the medicament is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

The substituted 4,5,6,7-tetrahydro-isoxazolo[4,5-c]pyridine compounds according to the invention used in the medicament according to the invention in a depot in dissolved form or in a dressing, optionally with the addition of skin penetration promoters, are suitable percutaneous administration preparations.

Orally or percutaneously administrable formulations may also release the particular substituted 4,5,6,7-tetrahydro-isoxazolo[4,5-c]pyridine compounds according to the invention in delayed manner.

Production of the medicaments according to the invention proceeds with the assistance of conventional means, devices, methods and processes known from the prior art, as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure.

The quantity of the particular substituted 4,5,6,7-tetrahydro-isoxazolo[4,5-c]pyridine compounds of the above-stated general formula I to be administered to patients may vary and is for example dependent on the weight or age of the patient and on the mode of administration, the indication and the severity of the complaint. Conventionally, at least one such compound according to the invention is administered in a quantity of 0.005 to 100 mg/kg, preferably of 0.05 to 75 mg/kg, of patient body weight.

Pharmacological Methods:

b) Method for Determining Noradrenalin and 5-HT Uptake Inhibition:

Synaptosomes from rat brain regions are freshly isolated for in vitro studies, as described in the publication "The isolation of nerve endings from brain" by E. G. Gray and V. P. Whittaker, J. Anatomy 96, pages 79-88, 1962. The corresponding literature description is hereby introduced as a reference and is deemed to be part of the disclosure.

The tissue (hypothalamus for the determination of noradrenalin uptake inhibition and medulla and pons for the determination of 5-HT uptake inhibition) is homogenised in ice-cooled 0.32 M sucrose (100 mg of tissue/1 mL) in a glass homogeniser with Teflon pestle using five complete up and down strokes at 840 revolutions/minute.

The homogenate is centrifuged at 4° C. for 10 minutes at 1000 g. After subsequent centrifugation at 17000 g for 55 minutes, the synaptosomes ($P_2$ fraction) are obtained, which are resuspended in 0.32 M glucose (0.5 mL/100 mg of original weight).

The particular uptake is measured in a 96-well microtitre plate. The volume is 250 µL and the incubation proceeds at room temperature (approx. 20-25° C.) under an $O_2$ atmosphere.

The incubation time is 7.5 minutes for [$^3$H]-NA and 5 minutes for [$^3$H]-5-HT. The 96 samples are then filtered through a Unifilter GF/B® microtitre plate (Packard) and washed with 200 mL of incubated buffer using a "Brabdel MPXRI-96T Cell-Harvester". The Unifilter GF/B plate is dried for 1 hour at 55° C. The plate is then sealed with a Back Seal® (Packard) and 35 µL of scintillation fluid are added per well (Ultima Gold®, Packard). After sealing with a top Seal® (Packard) and establishing an equilibrium (around 5 hours), radioactivity is determined in a "Trilux 1450 Microbeta" (Wallac).

The quantity of protein used in the above determination corresponds to the values known from the literature, as for example described in "Protein measurement with the folin phenol reagent", Lowry et al., J. Biol. Chem., 193, 265-275, 1951.

A detailed description of the method may additionally be found in the literature, for example in M. Ch. Frink, H.-H. Hennies, W. Engelberger, M. Haurand and B. Wilffert (1996) Arzneim.-Forsch./Drug Res. 46 (III), 11, 1029-1036.

The corresponding literature descriptions are hereby introduced in each case as a reference and are deemed to be part of the present disclosure.

The following characteristics were determined for the NA or 5-HT transporter:

NA uptake: Km=0.32±0.11 µM

5HT uptake: Km=0.084±0.011 µM b) Method for Determining Affinity for the Batrachotoxin (BTX) Binding Site of the Sodium Channel Binding site 2 of the sodium channel is the so-called batrachotoxin (BTX) binding site. [$^3$H]-Batrachotoxin in A20 α-benzoate (10 nM in the batch) is used as the ligand. The ion channel particles (synaptosomes) are enriched from rat cerebrocortex, as described in the publication by Gray and Whittaker (E. G. Gray and V. P. Whittaker, 1962, J. Anat. 76, 79-88. The corresponding description is hereby introduced as a reference and is deemed to be part of the present disclosure. The radioactivity measured in the presence of veratridine ($3 \times 10^{-4}$ M in the batch) is defined as non-specific binding.

The assay conditions are as published by Pauwels, Leysen and Laduron, as described in Eur. J. Pharmacol. 124, 291-298. The corresponding description is hereby introduced as a reference and is deemed to be part of the present disclosure.

At variance with this method, the total batch is reduced to 250 µL, such that the assay may be performed on 96-well microtitre plates. The incubation time in these microtitre plates amounts to two hours at room temperature (approx. 20-25° C.).

The following characteristics were determined for the $K_D$ value of the binding site:

$K_D$: 24.63±1.56 nM

The invention is explained below with reference to Examples. These explanations are given merely by way of example and do not restrict the general concept of the invention.

EXAMPLES

The yields of the compounds produced have not been optimised.

All temperatures are uncorrected.

"Ether" means diethyl ether, "EtOAc" ethyl acetate, "DCM" dichloromethane, "DMF" N,N-dimethylformamide, "EtOH" ethanol, "MeOH" methanol. "Equivalents" means molar equivalents, "m.p." melting point or melting range, "RT" room temperature, i.e. approx. 20° C., "min" minutes, "h" hours, "sat." saturated and aq. "aqueous".

Further abbreviations:

Boc tert-butoxy-carbonyl

BOP benzotriazol-1-yl-oxy-tris-dimethylaminophosphonium hexafluorophosphate

DMAP 4,4-dimethylaminopyridine

The chemicals and solvents used were purchased from conventional suppliers (Acros, Avocado, Aldrich, Bachem, Fluka, Lancaster, Maybridge, Merck, Sigma, TCI etc.) or synthesised by conventional methods familiar to the person skilled in the art.

Silica gel 60 (0.040-0.063 mm) from E. Merck, Darmstadt, was used as the stationary phase for the column chromatography.

Thin-layer chromatography was performed with pre-coated silica gel 60 F 254 HPTLC plates from E. Merck, Darmstadt.

The mobile solvent mixture ratios for chromatographic investigations are always stated in volume/volume. Analysis was carried out by NMR and HPLC-MS.

Synthesis of 6,7-dihydro-4H-isoxazolo[4,5-c]pyridine-3,5-dicarboxylic acid 5-tert-butyl ester (F)

Synthesis of the starting substance 6,7-dihydro-4H-isoxazolo[4,5-c]pyridine-3,5-dicarboxylic acid 5-tert-butyl ester (F) for the preparation of the substituted 4,5,6,7-tetrahydro-isoxazolo[4,5-c]pyridine compounds of the general formula I according to the invention is shown in Scheme 1.

Scheme 1.

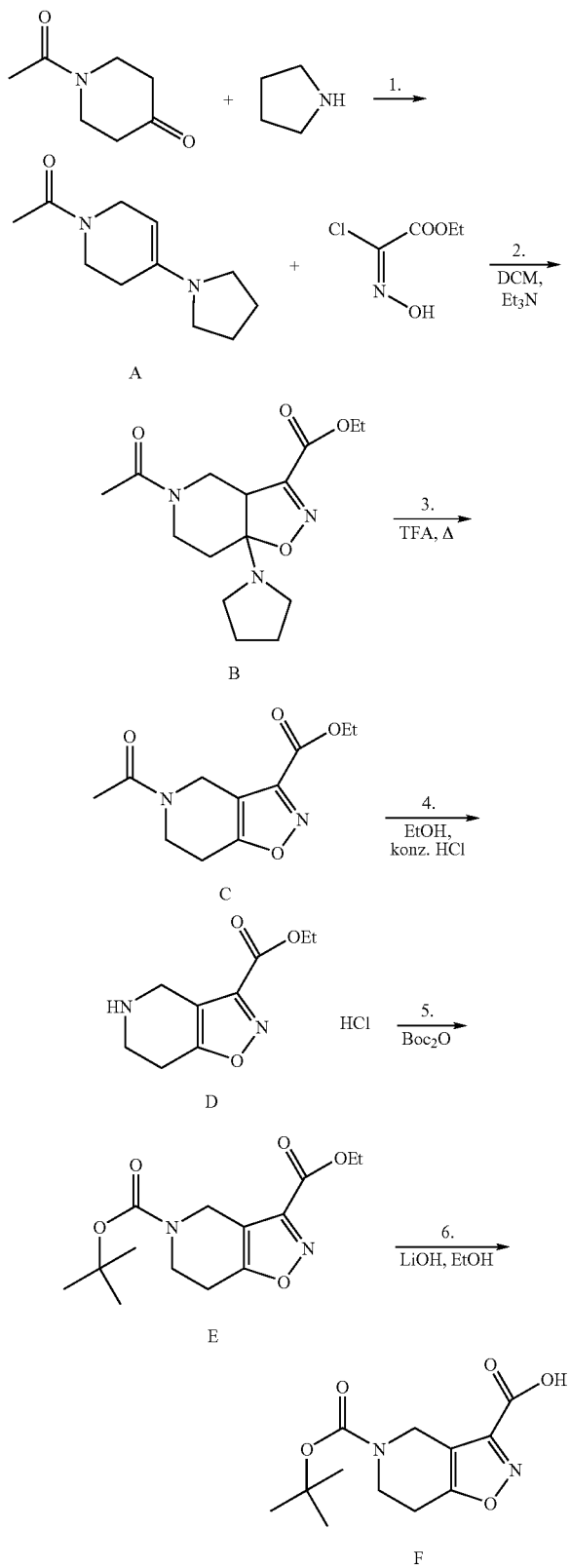

[Key: Stufe = stage; konz. = conc.]

Stage 1

Synthesis of 1-(4-pyrrolidin-1-yl-3,6-dihydro-2H-pyridin-1-yl)-ethanone (A)

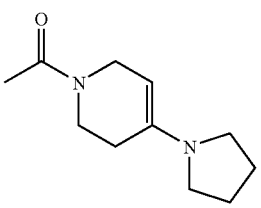

A mixture of 4.95 mL (40 mmol) of 1-acetyl-4-piperidinone, 3.64 mL (44 mmol) of pyrrolidine, 15 mL of toluene and a catalytic quantity of p-toluenesulfonic acid was heated for 12 h with refluxing on a water separator. After removal of the solvent under a vacuum, 7.7 g (99% of theoretical) of the desired product 1-(4-pyrrolidin-1-yl-3,6-dihydro-2H-pyridin-1-yl)-ethanone (A) were obtained in the form of a brown-red oil.

Stage 2

Synthesis of 5-acetyl-7a-pyrrolidin-1-yl-3a,4,5,6,7,7a-hexahydro-isoxazolo[4,5-c]pyridine-3-carboxylic acid ethyl ester (B)

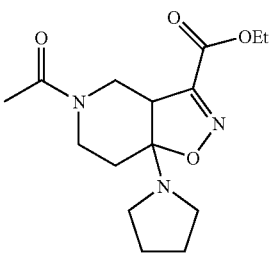

A solution of 17.9 g (0.118 mol) of 2-chlorohydroxyiminoacetic acid ethyl ester in 20 mL of DCM was added to a solution of 16.3 g (84 mmol) of 1-(4-pyrrolidin-1-yl-3,6-dihydro-2H-pyridin-1-yl)-ethanone (A) in 150 mL of DCM. On so doing, the solution warmed up and turned red. After cooling to 0° C. (ice bath), 16.4 g (0.118 mol) of triethylamine were slowly added dropwise with stirring. The mixture was stirred for 12 h at RT and then washed, firstly with 10% (weight percent) citric acid solution in water, and then with sat. aq. common salt solution. After removal of the solvent under a vacuum, the residue was purified by column chromatography ($SiO_2$, EtOAc/EtOH 9:1). 18.5 g (71% of theoretical) of the desired product 5-acetyl-7a-pyrrolidin-1-yl-3a,4,5,6,7,7a-hexahydro-isoxazolo[4,5-c]pyridine-3-carboxylic acid ethyl ester (B) were obtained in the form of a brown oil.

Stage 3

Synthesis of 5-acetyl-4,5,6,7-tetrahydro-isoxazolo[4,5-c]pyridine-3-carboxylic acid ethyl ester (C)

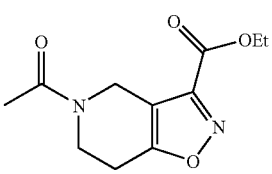

A mixture of 18.0 g (58 mmol) of 5-acetyl-7a-pyrrolidin-1-yl-3a,4,5,6,7,7a-hexahydro-isoxazolo[4,5-c]pyridine-3-carboxylic acid ethyl ester (B) in 150 mL of DCM and 6.47 mL (87 mmol) of trifluoroacetic acid was heated to reflux for 8 h. After addition of 100 mL of water, the organic phase was dried over MgSO$_4$ and the solvent removed under a vacuum. The remaining brown oil was purified by column chromatography (SiO$_2$, EtOAc/EtOH 10:1). 12.5 g (90% of theoretical) of the desired product 5-acetyl-4,5,6,7-tetrahydro-isoxazolo[4,5-c]pyridine-3-carboxylic acid ethyl ester (C) were obtained in the form of a brown-yellow oil.

Stage 4

Synthesis of 4,5,6,7-tetrahydro-isoxazolo[4,5-c]pyridine-3-carboxylic acid ethyl ester hydrochloride (D)

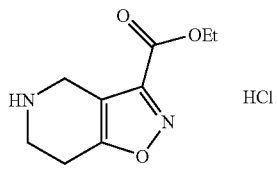

31.1 g (130 mmol) of 5-acetyl-4,5,6,7-tetrahydro-isoxazolo[4,5-c]pyridine-3-carboxylic acid ethyl ester (C) were dissolved in 30 mL of EtOH and combined at RT with 30 mL (260 mmol) of 32% (weight percent) hydrochloric acid solution in water. After two hours' heating with refluxing, the solution was evaporated and introduced into 500 mL of cooled EtOAc (ice bath). The resultant precipitate was separated and dried under a vacuum. 8.13 g (27% of theoretical) of the desired product 4,5,6,7-tetrahydro-isoxazolo[4,5-c]pyridine-3-carboxylic acid ethyl ester hydrochloride (D) were obtained.

m.p.: 74° C.

Stage 5

Synthesis of 6,7-dihydro-4H-isoxazolo[4,5-c]pyridine-3,5-dicarboxylic acid 3-ethyl ester 5-tert-butyl ester (E)

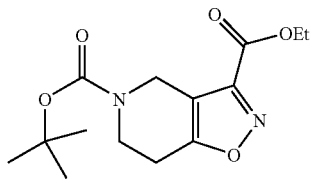

300 mg (1.21 mmol) of 4,5,6,7-tetrahydro-isoxazolo[4,5-c]pyridine-3-carboxylic acid ethyl ester hydrochloride (D) were dissolved in 20 mL of a dioxane/water mixture (2:1) and combined with 505 µl (3.63 mmol) of triethylamine and then, with ice cooling, with 290 mg (1.33 mmol) of di-tert-butyl dicarbonate [(Boc)$_2$O]. The mixture was stirred at RT for 12 h and the solvent removed under a vacuum. The residue was purified by column chromatography (SiO$_2$, EtOAc/EtOH 20:1). 90 mg (25% of theoretical) of the desired product 6,7-dihydro-4H-isoxazolo[4,5-c]pyridine-3,5-dicarboxylic acid 3-ethyl ester 5-tert-butyl ester (E) were obtained in the form of a colourless oil.

Stage 6

Synthesis of 6,7-dihydro-4H-isoxazolo[4,5-c]pyridine-3,5-dicarboxylic acid 5-tert-butyl ester (F)

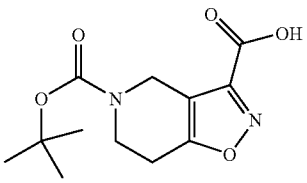

A mixture of 7.31 g (25 mmol) of 6,7-dihydro-4H-isoxazolo[4,5-c]pyridine-3,5-dicarboxylic acid 3-ethyl ester 5-tert-butyl ester (E), 43 g (30 mmol) of lithium hydroxide and 75 mL of EtOH was stirred at RT for 12 h. The solvent was removed under a vacuum and the residue redissolved in a mixture of water/citric acid (pH=4) and ether. The organic phase was separated off, dried over magnesium sulfate and the solvent was removed under a vacuum. 6.65 g (99% of theoretical) of the desired product 6,7-dihydro-4H-isoxazolo[4,5-c]pyridine-3,5-dicarboxylic acid 5-tert-butyl ester (F) were obtained in the form of a yellow oil which crystallised at RT.

General Method 1

Reaction of 6,7-dihydro-4H-isoxazolo[4,5-c]pyridine-3,5-dicarboxylic acid 5-tert-butyl Ester (F) with Primary or Secondary Amines

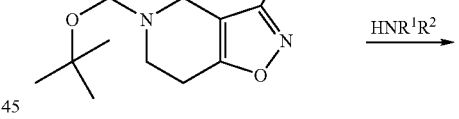

F

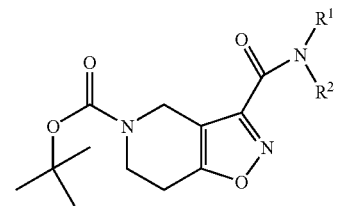

G

A mixture of 1.0 equivalent of the compound 6,7-dihydro-4H-isoxazolo[4,5-c]pyridine-3,5-dicarboxylic acid 5-tert-butyl ester (F), 1.0 equivalent of the particular primary or secondary amine HNR$^1$R$^2$, 2.7 equivalents of N-methylmorpholine and 1.8 equivalents of BOP in DMF was stirred at RT for 12 h. After removal of the solvent under a vacuum, the residue was combined with water and EtOAc. The organic phase was washed with water, 10% (weight percent) citric acid solution in water, sat. aq. Na$_2$CO$_3$ and sat. aq. NaCl solution, dried over MgSO$_4$ and the solvent was removed

47 under a vacuum. After purification by column chromatography on silica gel (ether/hexane 10:1), the desired coupling product of the general formula G was obtained.

General Method 2

Elimination of the Boc Group from Compounds of the General Formula G

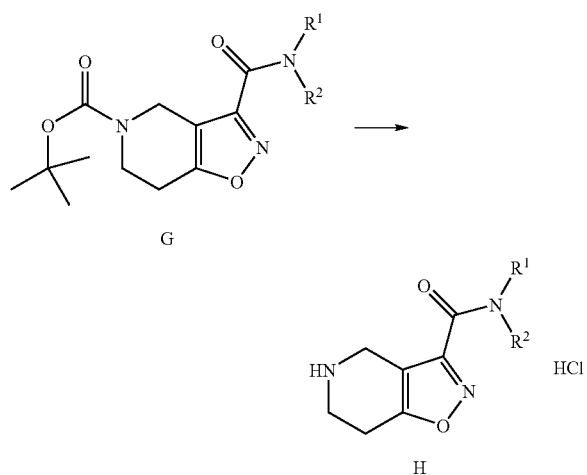

Compound G was dissolved in a 4 M hydrochloric acid solution in MeOH and stirred at RT until conversion of the starting compound was complete. The solvent was removed under a vacuum until the solution became cloudy and the reaction mixture was left to stand overnight at 4° C. The precipitate was filtered out, washed with a little ether and dried under a vacuum in order to obtain the desired product of the general formula H, optionally in the form of the corresponding hydrochloride.

General Method 3

Reaction of Compounds of the General Formula H with Carboxylic Acid Halides or Sulfonic Acid Halides

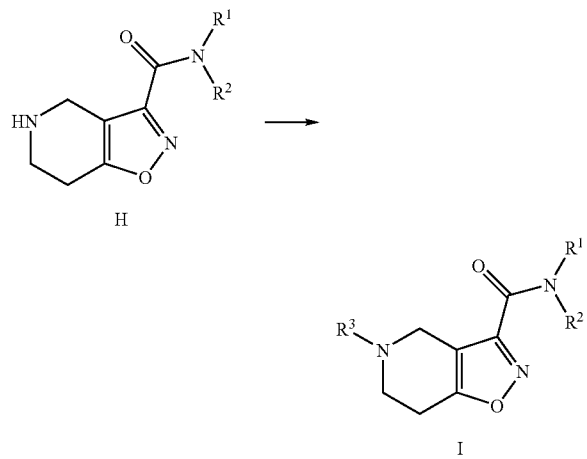

The compound of the general formula H (1.0 equivalent) was added at 0° C. to a solution of the particular acid halide

48

(1.5 equivalents), triethylamine (2.0 equivalents) and a catalytic quantity of DMAP in DCM. The reaction solution was heated to RT and stirred overnight. After addition of 10% (weight percent) aq. $NH_4Cl$ solution, the organic phase was separated and dried over $MgSO_4$. The solvent was removed under a vacuum and the residue purified by column chromatography on silica gel with EtOAc/hexane mixtures as eluent in order to obtain the desired product of the general formula I.

Example 66

5-Pent-4-enoyl-4,5,6,7-tetrahydro-isoxazolo[4,5-c] pyridine-3-carboxylic acid cyclopropylmethyl amide

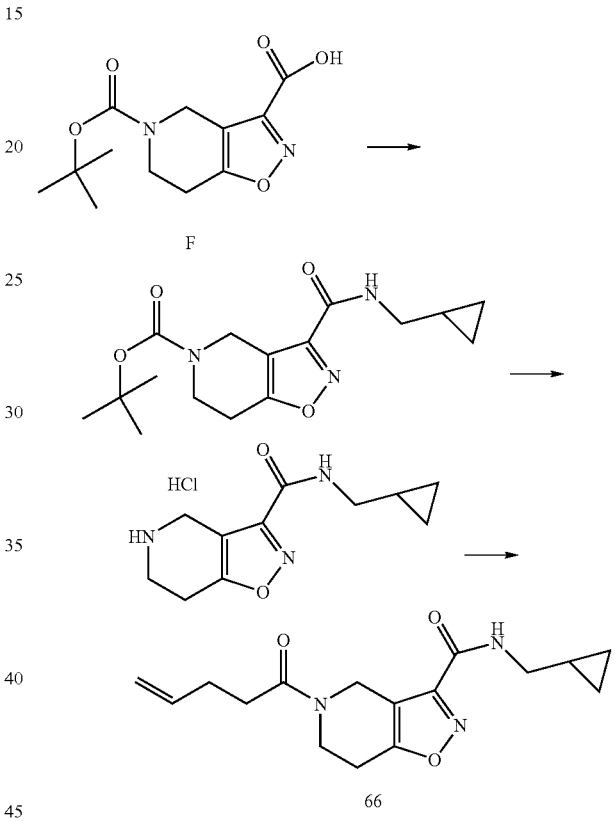

Synthesis of 3-(cyclopropylmethyl-carbamoyl)-6,7-dihydro-4H-isoxazolo[4,5-c]pyridine-5-carboxylic acid tert-butyl ester In a manner similar to general method 1, 280 mg (1.0 mmol) of 6,7-dihydro-4H-isoxazolo[4,5-c]pyridine-3,5-dicarboxylic acid 5-tert-butyl ester were reacted with 90 µL of cyclopropylmethylamine to yield 260 mg (78% of theoretical) of 3-(cyclopropylmethyl-carbamoyl)-6,7-dihydro-4H-isoxazolo[4,5-c]pyridine-5-carboxylic acid tert-butyl ester, which were obtained in the form of a yellow oil.

Synthesis of 4,5,6,7-tetrahydro-isoxazolo[4,5-c]pyridine-3-carboxylic acid cyclopropylmethyl amide hydrochloride In a manner similar to general method 2, 260 mg of 3-(cyclopropylmethyl-carbamoyl)-6,7-dihydro-4H-isoxazolo[4, 5-c]pyridine-5-carboxylic acid tert-butyl ester were reacted to yield 160 mg (77% of theoretical) of 4,5,6,7-tetrahydroisoxazolo[4,5-c]pyridine-3-carboxylic acid cyclopropylmethyl amide hydrochloride, which were obtained as a colourless solid.

m.p.: 227.6° C.

Synthesis of 5-pent-4-enoyl-4,5,6,7-tetrahydro-isoxazolo[4,5-c]pyridine-3-carboxylic acid cyclopropylmethyl amide The corresponding base was released from 4,5,6,7-tetrahydro-isoxazolo[4,5-c]pyridine-3-carboxylic acid cyclopropylmethyl amide hydrochloride. In a manner similar to general method 3, 170 mg (0.42 mmol) of 4,5,6,7-tetrahydro-isoxazolo[4,5-c]pyridine-3-carboxylic acid cyclopropylmethyl amide were reacted with 89 µL (0.89 mmol) of 4-pentenoyl chloride to yield 150 mg (84% of theoretical) of 5-pent-4-enoyl-4,5,6,7-tetrahydro-isoxazolo[4,5-c]pyridine-3-carboxylic acid cyclopropylmethyl amide (66), which were obtained in the form of a brown oil.

Example 86

1-(4-{4-[5-(Toluene-4-sulfonyl)-4,5,6,7-tetrahydro-isoxazolo[4,5-c]pyridine-3-carbonyl]-piperazin-1-yl}-phenyl)-ethanone

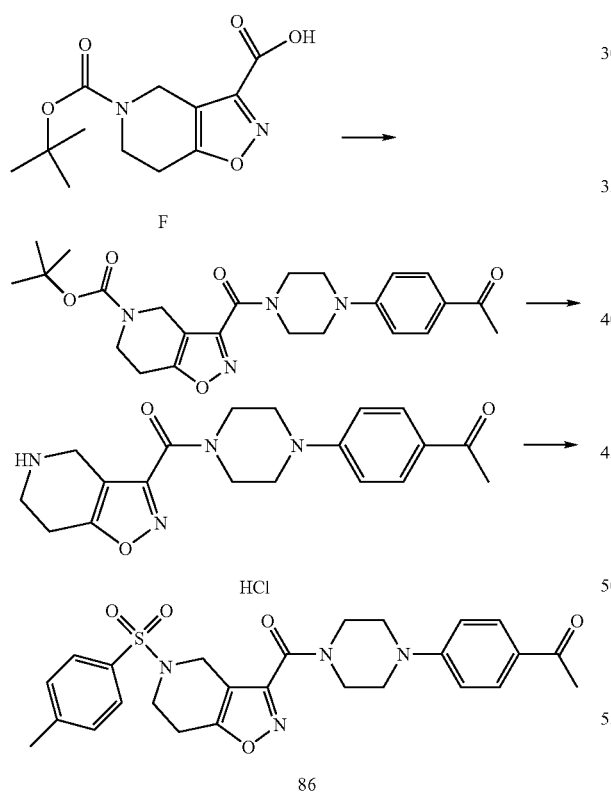

86

Synthesis of 3-[4-(4-acetyl-phenyl)-piperazine-1-carbonyl]-6,7-dihydro-4H-isoxazolo[4,5-c]pyridine-5-carboxylic acid tert-butyl ester In a manner similar to general method 1, 1.1 g (4.1 mmol) of 6,7-dihydro-4H-isoxazolo[4,5-c]pyridine-3,5-dicarboxylic acid 5-tert-butyl ester were reacted with 838 mg (4.1 mmol) of 4-piperazinoacetophenone to yield 790 mg (42% of theoretical) of 3-[4-(4-acetyl-phenyl)-piperazine-1-carbonyl]-6,7-dihydro-4H-isoxazolo[4,5-c]pyridine-5-carboxylic acid tert-butyl ester, which were obtained in the form of a yellow-orange oil.

Synthesis of 1-[4-[4-(4,5,6,7-tetrahydro-isoxazolo[4,5-c]pyridine-3-carbonyl)-piperazin-1-yl]-phenyl]-ethanone hydrochloride In a manner similar to general method 2, 160 mg (0.35 mmol) of 3-[4-(4-acetyl-phenyl)-piperazine-1-carbonyl]-6,7-dihydro-4H-isoxazolo[4,5-c]pyridine-5-carboxylic acid tert-butyl ester were reacted to yield 90 mg (63% of theoretical) of 1-[4-[4-(4,5,6,7-tetrahydro-isoxazolo[4,5-c]pyridine-3-carbonyl)-piperazin-1-yl]-phenyl]-ethanone hydrochloride, which were obtained in the form of a white solid.

m.p.: 189.5° C.

Synthesis of 1-(4-{4-[5-(toluene-4-sulfonyl)-4,5,6,7-tetrahydro-isoxazolo[4,5-c]pyridine-3-carbonyl]-piperazin-1-yl}-phenyl)-ethanone The corresponding base was released from 1-[4-[4-(4,5,6,7-tetrahydro-isoxazolo[4,5-c]pyridine-3-carbonyl)-piperazin-1-yl]-phenyl]-ethanone hydrochloride, p-toluenesulfonic acid chloride was purified by means of HPLC on Multospher 120 RP18 AQ 5 µm (CS-Chromatographie, Langerwehe, Germany) using the mobile solvent MeOH/water 7:3 with 0.1 vol. % triethylamine.

In a manner similar to the general method, 170 mg (0.42 mmol) of 1-[4-[4-(4,5,6,7-tetrahydro-isoxazolo[4,5-c]pyridine-3-carbonyl)-piperazin-1-yl]-phenyl]-ethanone were reacted with 120 mg (0.63 mmol) of p-toluenesulfonic acid chloride to yield 60 mg (28% of theoretical) of 1-(4-{4-[5-(toluene-4-sulfonyl)-4,5,6,7-tetrahydro-isoxazolo[4,5-c]pyridine-3-carbonyl]-piperazin-1-yl}-phenyl)-ethanone (86), which were obtained in the form of a colourless solid.

m.p.: 187.8° C.

General Method 4

Reaction of Compounds of the General Formula H with Isocyanates or Thioisocyanates

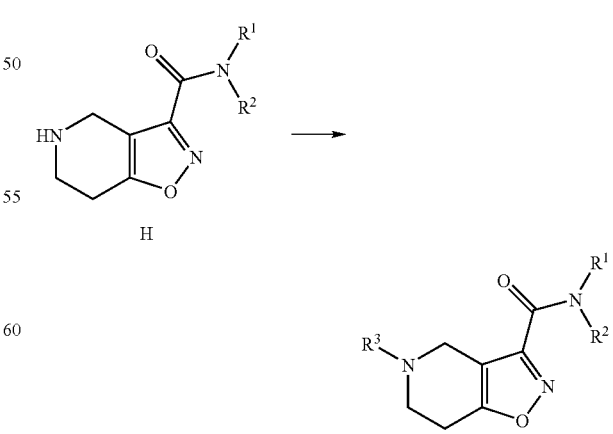

The particular isocyanate or thioisocyanate (100 μmol in 1 mL of toluene, 1.0 equivalent) was added at RT to a solution of the compound of the general formula H (100 μmol in 1 mL of toluene) in toluene (3 mL). The reaction mixture was stirred at 50° C. for at least 8 hours. The solvent was removed under a vacuum and the residue purified by means of preparative HPLC in order to obtain the desired product of the general formula I.

General Method 5

Reaction of Compounds of the General Formula H with Aldehydes

The particular aldehyde (120 μmol in 0.5 mL of MeOH) and then borane-pyridine complex ($BH_3 \cdot C_5H_5N$, 100 μmol in 0.5 mL MeOH) were added at RT with stirring to a solution of the compound of the general formula H (120 μmol in 0.5 mL of MeOH). The reaction mixture was stirred for at least 16 hours at 64° C. and then combined with stirring with 5% (weight percent) hydrochloric acid solution in water (0.5 mL). 10% (weight percent) sodium hydroxide solution in water (1 mL) was added to the reaction mixture and the mixture was extracted three times with DCM (in each case 2 mL). The combined organic phases were dried over $MgSO_4$ cartridges, the solvent removed under a vacuum and the residue purified by means of preparative HPLC in order obtain the desired product of the general formula I.

The production, not described in detail above, of the other compounds according to the Examples stated below also proceeded in a similar manner to the above-stated production methods, the educts used in each case being known to the person skilled in the art on the basis of these methods.

| Example | Name |
|---|---|
| 1 | 6,7-dihydro-4H-isoxazolo[4,5-c]pyridine-3,5-dicarboxylic acid 3-[(2-methoxy-ethyl) amide] 5-[(3-methoxyphenyl) amide] |
| 2 | 6,7-dihydro-4H-isoxazolo[4,5-c]pyridine-3,5-dicarboxylic acid 3-cyclopentyl amide 5-(4-fluorobenzyl amide) |
| 3 | 6,7-dihydro-4H-isoxazolo[4,5-c]pyridine-3,5-dicarboxylic acid 3-phenyl amide 5-[(4-trifluoromethoxy-phenyl) amide] |
| 4 | 6,7-dihydro-4H-isoxazolo[4,5-c]pyridine-3,5-dicarboxylic acid 5-[(4-methyl-3-nitro-phenyl) amide] 3-(phenethyl amide) |
| 5 | 6,7-dihydro-4H-isoxazolo[4,5-c]pyridine-3,5-dicarboxylic acid 3-[(2-methoxy-ethyl) amide]5-[(4-methyl-3-nitro-phenyl) amide] |
| 6 | [3-{[5-(2,5-difluoro-phenylcarbamoyl)-4,5,6,7-tetrahydro-isoxazolo[4,5-c]pyridine-3-carbonyl]-amino}-propionic acid ethyl ester |
| 7 | 6,7-dihydro-4H-isoxazolo[4,5-c]pyridine-3,5-dicarboxylic acid 5-[(4-butoxy-phenyl) amide] 3-[(2-methoxy-ethyl) amide] |
| 8 | 6,7-dihydro-4H-isoxazolo[4,5-c]pyridine-3,5-dicarboxylic acid 5-[(3-fluorophenyl) amide] 3-(phenethyl amide) |
| 9 | 6,7-dihydro-4H-isoxazolo[4,5-c]pyridine-3,5-dicarboxylic acid 5-[(4-methyl-3-nitro-phenyl) amide] 3-[(thiophen-2-ylmethyl) amide] |
| 10 | 6,7-dihydro-4H-isoxazolo[4,5-c]pyridine-3,5-dicarboxylic acid 3-benzyl amide 5-(phenethyl amide) |
| 11 | 6,7-dihydro-4H-isoxazolo[4,5-c]pyridine-3,5-dicarboxylic acid 3-[(2-ethylsulfanyl-ethyl) amide]5-[(3-methoxyphenyl) amide] |
| 12 | 6,7-dihydro-4H-isoxazolo[4,5-c]pyridine-3,5-dicarboxylic acid 5-[(3-cyano-phenyl) amide]3-[(thiophen-2-ylmethyl) amide] |
| 13 | 6,7-dihydro-4H-isoxazolo[4,5-c]pyridine-3,5-dicarboxylic acid 5-[(4-ethoxy-phenyl) amide] 3-phenyl amide |
| 14 | 6,7-dihydro-4H-isoxazolo[4,5-c]pyridine-3,5-dicarboxylic acid 3-(4-fluorobenzyl amide) 5-[(4-methyl-3-nitro-phenyl) amide] |
| 15 | 6,7-dihydro-4H-isoxazolo[4,5-c]pyridine-3,5-dicarboxylic acid 5-[(3-acetyl-phenyl) amide] 3-[(5-methyl-furan-2-ylmethyl) amide] |
| 16 | 6,7-dihydro-4H-isoxazolo[4,5-c]pyridine-3,5-dicarboxylic acid 5-[(4-methyl-3-nitro-phenyl) amide]3-prop-2-ynyl amide |
| 17 | 6,7-dihydro-4H-isoxazolo[4,5-c]pyridine-3,5-dicarboxylic acid 3-benzyl amide 5-phenyl amide |
| 18 | 6,7-dihydro-4H-isoxazolo[4,5-c]pyridine-3,5-dicarboxylic acid 5-[(1-naphthalen-1-yl-ethyl) amide]3-(phenethyl amide) |
| 19 | 6,7-dihydro-4H-isoxazolo[4,5-c]pyridine-3,5-dicarboxylic acid 5-[(3-fluorophenyl) amide] 3-prop-2-ynyl amide |
| 20 | 3-{[5-(2,5-dimethoxy-phenylcarbamoyl)-4,5,6,7-tetrahydro-isoxazolo[4,5-c]pyridine-3-carbonyl]-amino}-propionic acid ethyl ester |
| 21 | 6,7-dihydro-4H-isoxazolo[4,5-c]pyridine-3,5-dicarboxylic acid 5-[(4-ethoxy-phenyl) amide] 3-(4-fluorobenzyl amide) |
| 22 | 6,7-dihydro-4H-isoxazolo[4,5-c]pyridine-3,5-dicarboxylic acid 5-[(5-chloro-2-methoxyphenyl) amide] 3-(phenethyl amide) |
| 23 | 3-({3-[(5-methyl-furan-2-ylmethyl)-carbamoyl]-6,7-dihydro-4H-isoxazolo[4 5-c]pyridine-5-carbonyl}-amino)-benzoic acid ethyl ester |
| 24 | 6,7-dihydro-4H-isoxazolo[4,5-c]pyridine-3,5-dicarboxylic acid 5-[(5-chloro-2-methoxyphenyl) amide] 3-(isobutyl-amide) |
| 25 | [2-oxo-2-(3-prop-2-ynylcarbamoyl-6,7-dihydro-4H-isoxazolo[4,5-c]pyridin-5-yl)-ethoxy]acetic acid |
| 26 | 3-ethyl-5-[3-(2-methoxy-ethylcarbamoyl)-6,7-dihydro-4H-isoxazolo[4,5-c]pyridin-5-yl]-3-methyl-5-oxo-pentanoic acid |
| 27 | (1-benzyloxymethyl-2-oxo-2-{3-[(pyridin-3-ylmethyl)-carbamoyl]-6,7-dihydro-4H-isoxazolo[4,5-c]pyridin-5-yl}-ethyl)-carbamic acid tert-butyl ester |
| 28 | {1-[2-oxo-2-(3-phenylcarbamoyl-6,7-dihydro-4H-isoxazolo[4,5-c]pyridin-5-yl)-ethyl]-cyclopentyl}acetic acid |

-continued

| Example | Name |
|---|---|
| 29 | 3-ethyl-3-methyl-5-oxo-5-(3-phenylcarbamoyl-6,7-dihydro-4H-isoxazolo[4,5-c]pyridin-5-yl)-pentanoic acid |
| 30 | (2-oxo-2-{3-[(thiophen-2-ylmethyl)-carbamoyl]-6,7-dihydro-4H-isoxazolo[4,5-c]pyridin-5-yl}-ethoxy)acetic acid |
| 31 | 3,3-dimethyl-4-{3-[(5-methyl-furan-2-ylmethyl)-carbamoyl]-6,7-dihydro-4H-isoxazolo[4,5-c]pyridin-5-yl}-4-oxo-butanoic acid |
| 32 | 5-(4-trifluoromethoxy-benzenesulfonyl)-4,5,6,7-tetrahydro-isoxazolo[4,5-c]pyridine-3-carboxylic acid benzyl-phenethyl amide |
| 33 | 5-benzenesulfonyl-4,5,6,7-tetrahydro-isoxazolo[4,5-c]pyridine-3-carboxylic acid (1-naphthalen-2-ylmethyl-pyrrolidin-3-yl) amide |
| 34 | 5-(4-fluoro-benzenesulfonyl)-4,5,6,7-tetrahydro-isoxazolo[4,5-c]pyridin-3-yl]-(4-thieno[2,3-d]pyrimidine-4-yl-piperazin-1-yl)-methanone |
| 35 | 5-(4-fluoro-benzenesulfonyl)-4,5,6,7-tetrahydro-isoxazolo[4,5-c]pyridine-3-carboxylic acid (3-phenyl-propyl) amide |
| 36 | 5-(3-phenyl-acryloyl)-4,5,6,7-tetrahydro-isoxazolo[4,5-c]pyridine-3-carboxylic acid (2-dimethylamino-ethyl) amide |
| 37 | 5-(2-phenoxy-acetyl)-4,5,6,7-tetrahydro-isoxazolo[4,5-c]pyridine-3-carboxylic acid (2-dimethylamino-ethyl) amide |
| 38 | 5-(4-fluoro-benzenesulfonyl)-4,5,6,7-tetrahydro-isoxazolo[4,5-c]pyridine-3-carboxylic acid (1-methyl-3-phenyl-propyl) amide |
| 39 | 5-(4-fluoro-benzenesulfonyl)-4,5,6,7-tetrahydro-isoxazolo[4,5-c]pyridine-3-carboxylic acid [1-(4-trifluoromethyl-benzyl)-pyrrolidin-3-yl]amide |
| 40 | 5-(2,5-dichloro-benzenesulfonyl)-4,5,6,7-tetrahydro-isoxazolo[4,5-c]pyridine-3-carboxylic acid (2-benzyloxy-cyclopentyl) amide |
| 41 | 5-(5-tert-butyl-2-methyl-2H-pyrazole-3-carbonyl)-4,5,6,7-tetrahydro-isoxazolo[4,5-c]pyridine-3-carboxylic acid (2-dimethylamino-ethyl) amide |
| 42 | [5-(4-fluoro-benzenesulfonyl)-4,5,6,7-tetrahydro-isoxazolo[4,5-c]pyridin-3-yl]-[4-(4-fluorophenyl)-3,6-dihydro-2H-pyridin-1-yl]-methanone |
| 43 | 4-{[5-(4-fluoro-benzenesulfonyl)-4)5,6,7-tetrahydro-isoxazolo[4,5-c]pyridine-3-carbonyl]-amino}-piperidine-1-carboxylic acid ethyl ester |
| 44 | 5-(3-phenyl-acryloyl)-4,5,6,7-tetrahydro-isoxazolo[4,5-c]pyridine-3-carboxylic acid cyclopentyl amide |
| 45 | 5-(4-acetylamino-benzoyl)-4,5,6,7-tetrahydro-isoxazolo[4,5-c]pyridine-3-carboxylic acid cyclopropylmethyl amide |
| 46 | 5-(5-methyl-2-phenyl-2H-[1,2,3]triazole-4-carbonyl)-4,5,6,7-tetrahydro-isoxazolo[4,5-c]pyridine-3-carboxylic acid (pyridin-3-ylmethyl) amide |
| 47 | 5-benzenesulfonyl-4,5,6,7-tetrahydro-isoxazolo[4,5-c]pyridine-3-carboxylic acid 3,4-dimethoxy-benzyl amide |
| 48 | 2-(3,4-difluoro-phenyl)-1-{4-[5-(4-fluoro-benzenesulfonyl)-4,5,6,7-tetrahydro-isoxazolo[4,5-c]pyridine-3-carbonyl]-piperazin-1-yl}-ethanone |
| 49 | 3-(morpholine-4-carbonyl)-6,7-dihydro-4H-isoxazolo[4,5-c]pyridine-5-sulfonic acid dimethyl amide |
| 50 | 5-(furan-2-carbonyl)-4,5,6,7-tetrahydro-isoxazolo[4,5-c]pyridine-3-carboxylic acid (thiophen-2-ylmethyl) amide |
| 51 | 5-(4,7,7-trimethyl-3-oxo-2-oxa-bicyclo[2.2.1]heptane-1-carbonyl)-4,5,6,7-tetrahydro-isoxazolo[4,5-c]pyridine-3-carboxylic acid (2-pyrrolidin-1-yl-ethyl) amide |
| 52 | 5-(2,5-dichloro-benzenesulfonyl)-4,5,6,7-tetrahydro-isoxazolo[4,5-c]pyridine-3-carboxylic acid [2-(2-chlorophenyl)-ethyl] amide |
| 53 | 5-(4-methoxy-benzenesulfonyl)-4,5,6,7-tetrahydro-isoxazolo[4,5-c]pyridine-3-carboxylic acid p-tolyl amide |
| 54 | 5-(2-phenoxy-acetyl)-4,5,6,7-tetrahydro-isoxazolo[4,5-c]pyridine-3-carboxylic acid 4-fluorobenzyl amide |
| 55 | 1-{4-[5-(4-methoxy-benzenesulfonyl)-4,5,6,7-tetrahydro-isoxazolo[4,5-c]pyridine-3-carbonyl]-piperazin-1-yl}-ethanone |
| 56 | 5-(toluene-4-sulfonyl)-4,5,6,7-tetrahydro-isoxazolo[4,5-c]pyridine-3-carboxylic acid 4-sulfamoyl-benzyl amide |
| 57 | 5-(thiophene-2-sulfonyl)-4,5,6,7-tetrahydro-isoxazolo[4,5-c]pyridine-3-carboxylic acid (2-morpholin-4-yl-ethyl) amide |
| 58 | 5-(4-methoxy-benzoyl)-4,5,6,7-tetrahydro-isoxazolo[4,5-c]pyridine-3-carboxylic acid (2-dimethylamino-ethyl) amide |
| 59 | 5-(2,5-dichloro-benzenesulfonyl)-4,5,6,7-tetrahydro-isoxazolo[4,5-c]pyridine-3-carboxylic acid benzyl-phenethyl amide |
| 60 | 5-dimethylsulfamoyl-4,5,6,7-tetrahydro-isoxazolo[4,5-c]pyridine-3-carboxylic acid (2,6,6-trimethyl-bicyclo[3.1.1]hept-3-yl) amide |
| 61 | 5-benzenesulfonyl-4,5,6,7-tetrahydro-isoxazolo[4,5-c]pyridine-3-carboxylic acid indan-1-yl amide |
| 62 | 5-(4-methoxy-benzenesulfonyl)-4,5,6,7-tetrahydro-isoxazolo[4,5-c]pyridine-3-carboxylic acid (3-methoxy-propyl) amide |

| Example | Name |
|---|---|
| 63 | 5-(4,5-dichloro-thiophene-2-sulfonyl)-4,5,6,7-tetrahydro-isoxazolo[4,5-c]pyridine-3-carboxylic acid (2-morpholin-4-yl-ethyl) amide |
| 64 | 5-(2-benzyloxy-acetyl)-4,5,6,7-tetrahydro-isoxazolo[4,5-c]pyridine-3-carboxylic acid (2-pyrrolidin-1-yl-ethyl) amide |
| 65 | [5-(2,5-dichloro-benzenesulfonyl)-4,5,6,7-tetrahydro-isoxazolo[4,5-c]pyridin-3-yl]-[4-(2,4-dimethyl-phenyl)-piperazin-1-yl]-methanone |
| 67 | 3-methyl-2-{[5-(3-trifluoromethyl-benzenesulfonyl)-4,5,6,7-tetrahydro-isoxazolo[4,5-c]pyridine-3-carbonyl]-amino}-butanoic acid tert-butyl ester |
| 68 | 5-(3-trifluoromethyl-benzenesulfonyl)-4,5,6,7-tetrahydro-isoxazolo[4,5-c]pyridine-3-carboxylic acid benzyl-phenethyl amide |
| 69 | 5-(3-trifluoromethyl-benzenesulfonyl)-4,5,6,7-tetrahydro-isoxazolo[4,5-c]pyridine-3-carboxylic acid 2,4-dichloro-benzyl amide |
| 70 | 5-dimethylsulfamoyl-4,5,6,7-tetrahydro-isoxazolo[4,5-c]pyridine-3-carboxylic acid (2-cyano-ethyl)-pyridin-3-ylmethyl-amide |
| 71 | 5-(2-cyclopentyl-acetyl)-4,5,6,7-tetrahydro-isoxazolo[4,5-c]pyridine-3-carboxylic acid (2-pyrrolidin-1-yl-ethyl) amide |
| 72 | 5-(5-methyl-2-phenyl-2H-[1,2,3]triazole-4-carbonyl)-4,5,6,7-tetrahydro-isoxazolo[4,5-c]pyridine-3-carboxylic acid 4-fluorobenzyl amide |
| 73 | 5-(3-trifluoromethyl)-benzo)sulfonyl)-4,5,6,7-tetrahydro-isoxazolo[4,5-c]pyridine-3-carboxylic acid (2-ethyl-hexyl) amide |
| 74 | 5-(2,3-difluoro-4-methyl-benzoyl)-4)5,6,7-tetrahydro-isoxazolo[4,5-c]pyridine-3-carboxylic acid (2-dimethylamino-ethyl) amide |
| 75 | 5-(4-trifluoromethoxy-benzenesulfonyl)-4,5,6,7-tetrahydro-isoxazolo[4,5-c]pyridine-3-carboxylic acid 2,3-dichloro-benzyl amide |
| 76 | 5-dimethylsulfamoyl-4,5,6,7-tetrahydro-isoxazolo[4,5-c]pyridine-3-carboxylic acid [2-(4-chlorophenyl)-ethyl] amide |
| 77 | 5-(6-chloro-pyridine-3-carbonyl)-4,5,6,7-tetrahydro-isoxazolo[4,5-c]pyridine-3-carboxylic acid (2-pyrrolidin-1-yl-ethyl) amide |
| 78 | 5-[3-(4-fluoro-benzylcarbamoyl)-6,7-dihydro-4H-isoxazolo[4,5-c]pyridin-5-yl]-5-oxo-pentanoic acid methyl ester |
| 79 | 5-[2-(4-methoxyphenyl)-acetyl]-4,5,6,7-tetrahydro-isoxazolo[4,5-c]pyridine-3-carboxylic acid benzyl amide |
| 80 | 5-(4-trifluoromethoxy-benzenesulfonyl)-4,5,6,7-tetrahydro-isoxazolo[4,5-c]pyridine-3-carboxylic acid [3-(methylphenyl-amino)-propyl] amide |
| 81 | 5-[2-(4-chlorophenoxy)-acetyl]-4,5,6,7-tetrahydro-isoxazolo[4,5-c]pyridine-3-carboxylic acid cyclopentyl amide |
| 82 | [4-(2-cyclohexyl-ethyl)-piperazin-1-yl]-[5-(toluene-4-sulfonyl)-4,5,6,7-tetrahydro-isoxazolo[4,5-c]pyridin-3-yl]-methanone |
| 83 | N-{1-[5-(2,5-dichloro-benzenesulfonyl)-4,5,6,7-tetrahydro-isoxazolo[4,5-c]pyridine-3-carbonyl]-piperidin-4-ylmethyl}-2,2,2-trifluoroacetamide |
| 84 | 5-(4-methoxy-benzenesulfonyl)-4,5,6,7-tetrahydro-isoxazolo[4,5-c]pyridine-3-carboxylic acid [1-(4-methoxyphenyl)-ethyl] amide |
| 85 | 2-{[5-(thiophene-2-sulfonyl)-4,5,6,7-tetrahydro-isoxazolo[4,5-c]pyridine-3-carbonyl]-amino}-propionic acid ethyl ester |
| 87 | 5-(3-trifluoromethyl-benzenesulfonyl)-4,5,6,7-tetrahydro-isoxazolo[4,5-c]pyridine-3-carboxylic acid (4-allyloxy-benzyl)-furan-2-ylmethyl amide |
| 88 | 4-carbamoyl-4-{[5-(4-methoxy-benzenesulfonyl)-4,5,6,7-tetrahydro-isoxazolo[4,5-c]pyridine-3-carbonyl]-amino}-butanoic acid tert-butyl ester |
| 89 | 5-dimethylsulfamoyl-4,5,6,7-tetrahydro-isoxazolo[4,5-c]pyridine-3-carboxylic acid furan-2-ylmethyl-(4-methylsulfanyl-benzyl) amide |
| 90 | 5-(4-bromo-3-methyl-benzoyl)-4,5,6,7-tetrahydro-isoxazolo[4,5-c]pyridine-3-carboxylic acid (2-morpholin-4-yl-ethyl) amide |
| 91 | 5-(toluene-4-sulfonyl)-4,5,6,7-tetrahydro-isoxazolo[4,5-c]pyridine-3-carboxylic acid [1-(2,6-dichloro-benzyl)-pyrrolidin-3-yl] amide |
| 92 | 5-benzenesulfonyl-4,5,6,7-tetrahydro-isoxazolo[4,5-c]pyridine-3-carboxylic acid [2-(3,4-dichloro-phenyl)-ethyl] amide |
| 93 | 5-(3-difluoromethylsulfanyl-benzoyl)-4,5,6,7-tetrahydro-isoxazolo[4,5-c]pyridine-3-carboxylic acid (2-dimethylamino-ethyl) amide |
| 94 | 5-[2-(3-chlorophenoxy)-acetyl]-4,5,6,7-tetrahydro-isoxazolo[4,5-c]pyridine-3-carboxylic acid (2-pyrrolidin-1-yl-ethyl) amide |
| 95 | 5-(4-methoxy-benzenesulfonyl)-4,5,6,7-tetrahydro-isoxazolo[4,5-c]pyridine-3-carboxylic acid 2,3-dimethoxy-benzyl amide |

| Example | Name |
|---|---|
| 96 | 5-(4-trifluoromethoxy-benzenesulfonyl)-4,5,6,7-tetrahydro-isoxazolo[4,5-c]pyridine-3-carboxylic acid (1-methyl-3-phenyl-propyl) amide |
| 97 | (5-benzenesulfonyl-4,5,6,7-tetrahydro-isoxazolo[4,5-c]pyridin-3-yl)-[4-(3-phenyl-allyl)-piperazin-1-yl]-methanone |
| 98 | 3-{[5-(4-methoxy-benzoyl)-4,5,6,7-tetrahydro-isoxazolo[4,5-c]pyridine-3-carbonyl]-amino}-propionic acid ethyl ester |
| 99 | 5-(4-phenoxy-butyryl)-4,5,6,7-tetrahydro-isoxazolo[4,5-c]pyridine-3-carboxylic acid (2-dimethylamino-ethyl) amide |
| 100 | 5-(4-trifluoromethoxy-benzenesulfonyl)-4,5,6,7-tetrahydro-isoxazolo[4,5-c]pyridine-3-carboxylic acid [2-(7-methyl-1H-indol-3-yl)-ethyl] amide |
| 101 | [4-(3-phenyl-allyl)-piperazin-1-yl]-[5-(thiophene-2-sulfanyl)-4,5,6,7-tetrahydro-isoxazolo[4,5-c]pyridin-3-yl]-methanone |
| 102 | 5-(4-bromo-3-methyl-benzoyl)-4,5,6,7-tetrahydro-isoxazolo[4,5-c]pyridine-3-carboxylic acid (2-pyrrolidin-1-yl-ethyl) amide |
| 103 | 5-benzenesulfonyl-4,5,6,7-tetrahydro-isoxazolo[4,5-c]pyridine-3-carboxylic acid [1-(4-trifluoromethyl-benzyl)-pyrrolidin-3-yl] amide |
| 104 | 5-(thiophene-2-sulfonyl)-4,5,6,7-tetrahydro-isoxazolo[4,5-c]pyridine-3-carboxylic acid (2-phenyl-propyl) amide |
| 105 | 5-(3-chloro-4-fluoro-benzoyl)-4,5,6,7-tetrahydro-isoxazolo[4,5-c]pyridine-3-carboxylic acid phenethyl amide |
| 106 | 5-benzenesulfonyl-4,5,6,7-tetrahydro-isoxazolo[4,5-c]pyridine-3-carboxylic acid [2-(4-methoxy-phenoxy)-ethyl] amide |
| 107 | 5-dimethylsulfamoyl-4,5,6,7-tetrahydro-isoxazolo[4,5-c]pyridine-3-carboxylic acid 3-fluoro-4-trifluoromethyl-benzyl amide |
| 108 | 5-(3-methyl-benzoyl)-4,5,6,7-tetrahydro-isoxazolo[4,5-c]pyridine-3-carboxylic acid prop-2-ynyl amide |
| 109 | 5-(toluene-4-sulfonyl)-4,5,6,7-tetrahydro-isoxazolo[4,5-c]pyridine-3-carboxylic acid [2-(4-methoxy-phenoxy)-ethyl] amide |
| 110 | [4-(2-chlorophenyl)-piperazin-1-yl]-[5-(2,5-dichloro-benzenesulfonyl)-4,5,6,7-tetrahydro-isoxazolo[4,5-c]pyridin-3-yl]-methanone |
| 111 | 3-{[5-(2,6-difluoro-3-methyl-benzoyl)-4,5,6,7-tetrahydro-isoxazolo[4,5-c]pyridine-3-carbonyl]-amino}-propionic acid ethyl ester |
| 112 | 5-(2,5-dichloro-benzenesulfonyl)-4,5,6,7-tetrahydro-isoxazolo[4,5-c]pyridine-3-carboxylic acid 2,4-difluoro-benzyl amide |
| 113 | 5-benzenesulfonyl-4,5,6,7-tetrahydro-isoxazolo[4,5-c]pyridine-3-carboxylic acid 3-fluoro-4-trifluoromethyl-benzyl amide |
| 114 | 5-(4-butoxy-benzenesulfonyl)-4,5,6,7-tetrahydro-isoxazolo[4,5-c]pyridine-3-carboxylic acid isobutyl amide |
| 115 | 5-(3-fluoro-4-methyl-benzoyl)-4,5,6,7-tetrahydro-isoxazolo[4,5-c]pyridine-3-carboxylic acid (2-pyrrolidin-1-yl-ethyl) amide |
| 116 | 5-(2-chloro-5-trifluoromethyl-benzoyl)-4,5,6,7-tetrahydro-isoxazolo[4,5-c]pyridine-3-carboxylic acid isobutyl amide |
| 117 | 5-(4-trifluoromethoxy-benzenesulfonyl)-4,5,6,7-tetrahydro-isoxazolo[4,5-c]pyridine-3-carboxylic acid (1-benzyl-pyrrolidin-3-yl)-amide |
| 118 | 5-(3-chloro-benzenesulfonyl)-4,5,6,7-tetrahydro-isoxazolo[4,5-c]pyridine-3-carboxylic acid (2-pyrrolidin-1-yl-ethyl) amide |
| 119 | 5-(3-trifluoromethoxy-benzoyl)-4,5,6,7-tetrahydro-isoxazolo[4,5-c]pyridine-3-carboxylic acid (2-dimethylamino-ethyl) amide |
| 120 | 2-{[5-(toluene-4-sulfonyl)-4,5,6,7-tetrahydro-isoxazolo[4,5-c]pyridine-3-carbonyl]-amino}-propionic acid tert-butyl ester |
| 121 | 3-{[5-(4-chloro-benzenesulfonyl)-4,5,6,7-tetrahydro-isoxazolo[4,5-c]pyridine-3-carbonyl]-amino}-propionic acid ethyl ester |
| 122 | 5-dimethylsulfamoyl-4,5,6,7-tetrahydro-isoxazolo[4,5-c]pyridine-3-carboxylic acid [2-(3,4-dichloro-phenyl)-ethyl] amide |
| 123 | 5-(thiophene-2-sulfonyl)-4,5,6,7-tetrahydro-isoxazolo[4,5-c]pyridine-3-carboxylic acid cyclopropyl methyl amide |
| 124 | 5-(quinoline-6-carbonyl)-4,5,6,7-tetrahydro-isoxazolo[4,5-c]pyridine-3-carboxylic acid 4-fluorobenzyl amide |
| 125 | 3-{[5-(2-naphthalen-2-yl-acetyl)-4,5,6,7-tetrahydro-isoxazolo[4,5-c]pyridine-3-carbonyl]-amino}-propionic acid ethyl ester |
| 126 | [2-(3-isobutylcarbamoyl-6,7-dihydro-4H-isoxazolo[4,5-c]pyridin-5-yl)-2-oxo-1-phenyl-ethyl]-carbamic acid benzyl ester |
| 127 | 5-(4-methoxy-benzylthiocarbamoyl)-4,5,6,7-tetrahydro-isoxazolo[4,5-c]pyridine-3-carboxylic acid cyclopentyl amide |

-continued

| Example | Name |
|---|---|
| 128 | 5-benzoylaminocarbothioyl-4,5,6,7-tetrahydro-isoxazolo[4,5-c]pyridine-3-carboxylic acid (2-pyrrolidin-1-yl-ethyl) amide |
| 129 | 5-(4-chloro-benzylthiocarbamoyl)-4,5,6,7-tetrahydro-isoxazolo[4,5-c]pyridine-3-carboxylic acid cyclopropylmethyl amide |
| 130 | 5-(2-methoxy-ethylthiocarbamoyl)-4,5,6,7-tetrahydro-isoxazolo[4,5-c]pyridine-3-carboxylic acid phenethyl amide |
| 131 | 5-pentafluorophenylthiocarbamoyl-4,5,6,7-tetrahydro-isoxazolo[4,5-c]pyridine-3-carboxylic acid phenethyl amide |
| 132 | 5-(1-phenyl-ethylthiocarbamoyl)-4,5,6,7-tetrahydro-isoxazolo[4,5-c]pyridine-3-carboxylic acid phenethyl amide |
| 133 | 5-pentafluorophenylthiocarbamoyl-4,5,6,7-tetrahydro-isoxazolo[4,5-c]pyridine-3-carboxylic acid (5-methyl-furan-2-ylmethyl) amide |
| 134 | 3-{[5-(cyclohexylmethyl-thiocarbamoyl)-4,5,6,7-tetrahydro-isoxazolo[4,5-c]pyridine-3-carbonyl]-amino}-propionic acid ethyl ester |
| 135 | 5-(1-bromo-naphthalen-2-ylmethyl)-4,5,6,7-tetrahydro-isoxazolo[4,5-c]pyridine-3-carboxylic acid phenyl amide |
| 136 | $N^5$-(4-methoxyphenyl)-$N^3$-(4-sulfamoylbenzyl)-6,7-dihydroisoxazolo[4,5-c]pyridine-3,5(4H)-dicarboxamide |
| 137 | 5-(2-(3-chlorophenoxy)acetyl)-N-(2-(pyrrolidin-1-yl)ethyl)-4,5,6,7-tetrahydroisoxazolo[4,5-c]pyridino-3-carboxamide |
| 138 | 5-(2-fluorobenzoyl)-N-phenyl-4,5,6,7-tetrahydroisoxazolo[4,5-c]pyridine-3-carboxamide |
| 139 | N-(4-sulfamoylbenzyl)-5-tosyl-4,5,6,7-tetrahydroisoxazolo[4,5-c]pyridine-3-carboxamide |
| 140 | (5-(3,4-dichlorophenylsulfonyl)-4,5,6,7-tetrahydroisoxazolo[4,5-c]pyridin-3-yl)(4-(thiazol-2-yl)piperazin-1-yl)methanone |
| 141 | (5-(mesitylsulfonyl)-4,5,6,7-tetrahydroisoxazolo[4,5-c]pyridin-3-yl)(4-(thiazol-2-yl)piperazin-1-yl)methanone |
| 142 | (5-(naphthalen-1-ylsulfonyl)-4,5,6,7-tetrahydroisoxazolo[4,5-c]pyridin-3-yl)(4-(thiazol-2-yl)piperazin-1-yl)methanone |
| 143 | (5-(naphthalen-2-ylsulfonyl)-4,5,6,7-tetrahydroisoxazolo[4,5-c]pyridin-3-yl)(4-(thiazol-2-yl)piperazin-1-yl)methanone |
| 144 | (4-(3-(dimethylamino)propyl)piperazin-1-yl)(5-(mesitylsulfonyl)-4,5,6,7-tetrahydroisoxazolo[4,5-c]pyridin-3-yl)methanone dihydrochloride |
| 145 | (5-(3,4-dichlorophenylsulfonyl)-4,5,6,7-tetrahydroisoxazolo[4,5-c]pyridin-3-yl)(4-(3-(dimethylamino)propyl)piperazin-1-yl)methanone dihydrochloride |
| 146 | (5-(mesitylsulfonyl)-4,5,6,7-tetrahydroisoxazolo[4,5-c]pyridin-3-yl)(4-(2-(pyrrolidin-1-yl)ethyl)piperidin-1-yl)methanone |
| 147 | (5-(3,4-dichlorophenylsulfonyl)-4,5,6,7-tetrahydroisoxazolo[4,5-c]pyridin-3-yl)(4-(2-(pyrrolidin-1-yl)ethyl)piperidin-1-yl)methanone |
| 148 | (5-(naphthalen-2-ylsulfonyl)-4,5,6,7-tetrahydroisoxazolo[4,5-c]pyridin-3-yl)(4-(2-(pyrrolidin-1-yl)ethyl)piperidin-1-yl)methanone |
| 149 | (5-(Naphthalene-1-ylsulfonyl)-4,5,6,7-tetrahydroisoxazolo[4,5-c]pyridin-3-yl)(4-(2-(pyrrolidin-1-yl)ethyl)piperidin-1-yl)methanone hydrochloride |
| 150 | $N^3$-benzyl-$N^5$-(1-phenylethyl)-6,7-dihydroisoxazolo[4,5-c]pyridine-3,5(4H)-dicarboxamide |
| 151 | $N^3$-benzyl-$N^5$-(4-methoxyphenyl)-6,7-dihydroisoxazolo[4,5-c]pyridine-3,5(4H)-dicarboxamide |
| 152 | N-p-tolyl-5-tosyl-4,5,6,7-tetrahydroisoxazolo[4,5-c]pyridine-3-carboxamide |
| 153 | 5-(3-fluoro-4-(trifluoromethyl)benzoyl)-N-(2-methoxyethyl)-4,5,6,7-tetrahydroisoxazolo[4,5-c]pyridine-3-carboxamide |
| 154 | $N^5$-(4-methoxyphenyl)-$N^3$-(4-sulfamoylbenzyl)-6,7-dihydroisoxazolo[4,5-c]pyridine-3,5(4H)-dicarboxamide |
| 155 | 5-(2-(3-chlorophenoxy)acetyl)-N-(2-(pyrrolidin-1-yl)ethyl)-4,5,6,7-tetrahydroisoxazolo[4,5-c]pyridine-3-carboxamide |
| 156 | 5-(2-fluorobenzoyl)-N-phenyl-4,5,6,7-tetrahydroisoxazolo[4,5-c]pyridine-3-carboxamide |
| 157 | N-(4-sulfamoylbenzyl)-5-tosyl-4,5,6,7-tetrahydroisoxazolo[4,5-c]pyridine-3-carboxamide |

Pharmacological Data:

The 5-HT uptake inhibition and noradrenalin uptake inhibition of the substituted 4,5,6,7-tetrahydro-isoxazolo[4,5-c]pyridine compounds according to the invention of the general formula I were determined as described above.

The investigated 4,5,6,7-tetrahydro-isoxazolo[4,5-c]pyridine compounds of the general formula I exhibit excellent inhibition of 5-HT and noradrenalin reuptake.

The affinity of the substituted 4,5,6,7-tetrahydro-isoxazolo[4,5-c]pyridine compounds according to the invention for the batrachotoxin (BTX) binding site was likewise determined as described above.

The compounds according to the invention also exhibit an excellent affinity for the batrachotoxin (BTX) binding site of the sodium channel.

| Compound according to Example | 5-HT uptake (rat), 10 µM, % inhibition | NA Uptake (rat), 10 µM, % inhibition | BTX inhibition (rat) % inhibition |
|---|---|---|---|
| 1 | 47 | | |
| 2 | 41 | | 83 |
| 3 | 45 | | 73 |
| 4 | 45 | 57 | 80 |
| 5 | 47 | | |
| 6 | 43 | | |
| 7 | 44 | | |
| 8 | 54 | 66 | 72 |
| 9 | 45 | | 43 |
| 10 | 51 | 42 | 64 |
| 11 | 54 | | |
| 12 | 51 | 46 | 47 |
| 13 | 48 | 51 | 58 |
| 14 | 53 | | 70 |
| 15 | 58 | | |
| 16 | 55 | | |
| 17 | 64 | | |
| 18 | 42 | 47 | 75 |
| 19 | 50 | | |
| 20 | 51 | | |
| 21 | 56 | | 68 |
| 22 | 60 | | 56 |
| 23 | 52 | | 46 |
| 24 | | 51 | |
| 25 | | | |
| 26 | 54 | | |
| 27 | 41 | | |
| 28 | 55 | 44 | 60 |
| 29 | | 44 | |
| 30 | 57 | | |
| 31 | 57 | | |
| 32 | | 82 | 59 |
| 33 | 74 | 88 | 93 |
| 34 | 74 | | 42 |
| 35 | | 73 | 59 |
| 36 | 72 | | |
| 37 | 61 | | |
| 38 | | 66 | |
| 39 | | 61 | 79 |
| 40 | | 71 | 65 |
| 41 | 76 | | |
| 42 | 69 | | 54 |
| 43 | | 63 | |
| 44 | | 76 | |
| 45 | 85 | | |
| 46 | 79 | | |
| 47 | 68 | 67 | |
| 48 | | 61 | |
| 49 | | 73 | |
| 50 | | 71 | |
| 51 | | 73 | 42 |
| 52 | 83 | | 44 |
| 53 | 89 | | |
| 54 | 84 | | |
| 55 | 68 | | |
| 56 | 96 | | |
| 57 | 63 | | |
| 58 | 81 | | |
| 59 | 71 | 79 | 58 |
| 60 | 81 | | |
| 61 | 64 | | |
| 62 | 67 | | |
| 63 | | 77 | 55 |
| 64 | 77 | | |
| 65 | 88 | | 49 |
| 66 | 62 | | |
| 67 | 73 | | |
| 68 | 63 | 84 | 51 |
| 69 | 64 | | |
| 70 | 63 | | |
| 71 | 69 | | |
| 72 | 70 | | |
| 73 | 63 | | |
| 74 | 62 | | |
| 75 | 65 | | |
| 76 | 63 | | 41 |
| 77 | 62 | | |
| 78 | 70 | | |
| 79 | 71 | | |
| 80 | 65 | | |
| 81 | | 68 | 65 |
| 82 | 62 | | 69 |
| 83 | 61 | | |
| 84 | 69 | | |
| 85 | 67 | | |
| 86 | 86 | | |
| 87 | 66 | | 41 |
| 88 | 62 | | |
| 89 | 64 | | |
| 90 | 65 | | 42 |
| 91 | 67 | | 61 |
| 92 | 61 | | |
| 93 | 88 | | |
| 94 | 94 | | 60 |
| 95 | 68 | | |
| 96 | | 63 | |
| 97 | 67 | 75 | 70 |
| 98 | 75 | | |
| 99 | 69 | | |
| 100 | 83 | | |
| 101 | 66 | 75 | 78 |
| 102 | 70 | | 73 |
| 103 | | 91 | 92 |
| 104 | | 77 | 50 |
| 105 | | 62 | |
| 106 | 76 | | |
| 107 | 61 | | |
| 108 | 88 | | |
| 109 | | 64 | 56 |
| 110 | | 86 | 55 |
| 111 | | 66 | |
| 112 | 71 | | |
| 113 | 83 | | 60 |
| 114 | 85 | | 58 |
| 115 | 65 | | |
| 116 | 77 | | |
| 117 | 68 | 75 | |
| 118 | | 63 | 76 |
| 119 | 73 | | |
| 120 | | 62 | |
| 121 | | 61 | |
| 122 | | 63 | |
| 123 | | 70 | |
| 124 | 65 | | |
| 125 | | 63 | |
| 126 | 80 | | 88 |
| 127 | | 63 | 74 |
| 128 | 80 | | 74 |
| 129 | 75 | | 53 |
| 130 | | 67 | 68 |
| 131 | | 73 | 58 |
| 132 | | 76 | 90 |

-continued

| Compound according to Example | 5-HT uptake (rat), 10 µM, % inhibition | NA Uptake (rat), 10 µM, % inhibition | BTX inhibition (rat) % inhibition |
|---|---|---|---|
| 133 | 63 | | |
| 134 | 61 | | 55 |
| 135 | | 60 | 61 |
| 140 | 47 | 46 | 55 |
| 141 | 58 | 41 | 67 |
| 142 | 30 | 31 | 54 |
| 143 | 29 | 44 | 48 |
| 144 | 21 | 24 | |
| 146 | 53 | 42 | 81 |
| 147 | 35 | 34 | 70 |
| 148 | 67 | 49 | 74 |
| 149 | 68 | 54 | 86 |
| 150 | 58 | 27 | 49 |
| 151 | 36 | 34 | 36 |
| 152 | 29 | 24 | 29 |
| 153 | 37 | −12 | 28 |
| 154 | −8 | −4 | 4 |
| 155 | 92 | 70 | 64 |
| 156 | 10 | 23 | 26 |
| 157 | 15 | 45 | 17 |

The invention claimed is:

1. A 4,5,6,7-tetrahydro-isoxazolo[4,5-c]pyridine compound corresponding to formula I

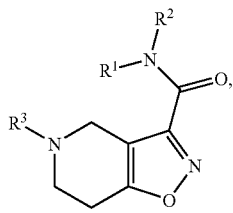

wherein
$R^1$ represents —(CHR$^4$)—(CH$_2$)$_c$—(CH$_2$)$_d$—C(=O)—OR$^5$ with c=0 or 1 and d=0 or 1;
—(CHR$^6$)—(CHR$^7$)$_e$—V$_f$—(CH$_2$)$_g$—W$_h$—(CH$_2$)$_i$—R$^8$ with e=0 or 1, f=0 or 1, g=0 or 1, h=0 or 1 and i=0 or 1, in which V and W mutually independently in each case represent O, S, NH, N(CH$_3$) or N(C$_2$H$_5$);
a linear or branched, saturated or unsaturated, optionally substituted C$_{1-10}$ aliphatic group;
an unsaturated or saturated, optionally substituted 3-, 4-, 5-, 6-, 7-, 8- or 9-membered cycloaliphatic group, which may be fused with a saturated or unsaturated, optionally aromatic, optionally substituted mono- or polycyclic ring system and/or be bridged with a linear or branched, optionally substituted C$_{1-5}$ alkylene group,
or an optionally substituted 5- to 14-membered aryl or heteroaryl group, which may be fused with a saturated or unsaturated, optionally substituted mono- or polycyclic ring system;
$R^2$ represents hydrogen;
—(CH$_2$)—R$^9$
or a linear or branched, saturated or unsaturated, optionally substituted C$_{1-10}$ aliphatic group;
or
$R^1$ and $R^2$, together with the nitrogen atom joining them together as a ring member, form a saturated or unsaturated, optionally substituted 4-, 5-, 6-, 7-, 8- or 9-membered heterocycloaliphatic group, wherein the heterocycloaliphatic group may in each case be substituted with 1, 2, 3, 4 or 5 substituents mutually independently selected from the group consisting of R$^{10}$, —C(=O)—R$^{11}$ and —(CH$_2$)—NH—C(=O)—R$^{12}$ and/or may in each case comprise a further 1, 2, 3, 4 or 5 heteroatom(s) mutually independently selected from the group consisting of oxygen, nitrogen and sulfur as ring member(s);
$R^3$ represents —C(=O)—NR$^{13}$R$^{14}$;
—C(=O)—R$^{15}$;
—C(=O)—(CH$_2$)$_j$—X$_k$—(CH$_2$)$_m$—(CH$_2$)$_n$—C(=O)—OR$^{16}$ with j=0 or 1, k=0 or 1, m=0 or 1 and n=0 or 1, in which X represents O, S, NH, N(CH$_3$), N(C$_2$H$_5$) or CR$^{17}$R$^{18}$;
—C(=O)—(CHR$^{19}$)—NH—C(=O)—OR$^{20}$;
—C(=O)—(CH$_2$)—(CH$_2$)$_p$—(CH$_2$)$_q$Y$_r$(CH$_2$)$_s$—R$^{21}$ with p=0 or 1, q=0 or 1, r=0 or 1 and s=0 or 1, in which Y represents O, S, NH, N(CH$_3$) or N(C$_2$H$_5$);
—C(=O)—(CH=CH)—R$^{22}$;
—S(=O)$_2$—R$^{23}$;
—S(=O)$_2$—NR$^{24}$R$^{25}$;
—C(=S)—NR$^{26}$—(CH$_2$)$_t$(CH$_2$)$_u$—Z$_v$—R$^{27}$ with t=0 or 1, u=0 or 1 and v=0 or 1, in which Z represents O, S, NH, N(CH$_3$) or N(C$_2$H$_5$);
—C(=S)—NR$^{26}$—(CHR$^{28}$)—R$^{29}$;
—C(=S)—NR$^{26}$—C(=O)—R$^{30}$;
or —(CH$_2$)—R$^{31}$;
$R^4$ represents —C(=O)—NH$_2$;
hydrogen;
or a linear or branched, saturated or unsaturated, optionally substituted C$_{1-10}$ aliphatic group;
$R^5$, $R^{17}$, $R^{18}$, $R^{24}$ and $R^{25}$, mutually independently, in each case represent a linear or branched, saturated or unsaturated, optionally substituted C$_{1-10}$ aliphatic group,
$R^6$, $R^7$, $R^{13}$, $R^{16}$ and $R^{26}$, mutually independently, in each case represent hydrogen;
or a linear or branched, saturated or unsaturated, optionally substituted C$_{1-10}$ aliphatic group;
$R^8$, $R^9$, $R^{21}$, $R^{22}$, $R^{23}$, $R^{30}$ and $R^{31}$, mutually independently, in each case represent
an unsaturated or saturated, optionally substituted 3-, 4-, 5-, 6-, 7-, 8- or 9-membered cycloaliphatic group, which may be fused with a saturated or unsaturated, optionally aromatic, optionally substituted mono- or polycyclic ring system,
or an optionally substituted 5- to 14-membered aryl or heteroaryl group, which may be fused with a saturated or unsaturated, optionally substituted mono- or polycyclic ring system;
$R^{10}$, $R^{11}$, $R^{12}$, $R^{14}$ and $R^{20}$, mutually independently, in each case represent a linear or branched, saturated or unsaturated, optionally substituted C$_{1-10}$ aliphatic group,
an unsaturated or saturated, optionally substituted 3-, 4-, 5-, 6-, 7-, 8- or 9-membered cycloaliphatic group, which may be fused with a saturated or unsaturated, optionally aromatic, optionally substituted mono- or polycyclic ring system and/or be attached via a linear or branched, optionally substituted C$_{1-5}$ alkylene, C$_{2-5}$ alkenylene or C$_{2-5}$ alkynylene group,
or an optionally substituted 5- to 14-membered aryl or heteroaryl group, which may be attached via a linear or branched, optionally substituted C$_{1-5}$ alkylene, C$_{2-5}$ alkenylene or C$_{2-5}$ alkynylene group;
$R^{15}$ and $R^{27}$, mutually independently, in each case represent
a linear or branched, saturated or unsaturated, optionally substituted C$_{1-10}$ aliphatic group, an unsaturated or saturated, optionally substituted 3-, 4-, 5-, 6-, 7-, 8- or 9-membered cycloaliphatic group, which may be bridged with a linear or branched, optionally substituted $C_{1-5}$ alkylene group, or an optionally substituted 5- to 14-membered aryl or heteroaryl group, which may be fused with a saturated or unsaturated, optionally substituted mono- or polycyclic ring system;

$R^{19}$ represents an optionally substituted 5- to 14-membered aryl or heteroaryl group, which may be attached via a linear or branched, optionally substituted $C_{1-5}$ alkylene, $C_{2-5}$ alkenylene or $C_{2-5}$ alkynylene group optionally comprising 1 or 2 heteroatom(s) as chain link(s)

$R^{28}$ and $R^{29}$, mutually independently, in each case represent a linear or branched, saturated or unsaturated, optionally substituted $C_{1-10}$ aliphatic group;

or an optionally substituted 5- to 14-membered aryl or heteroaryl group, which may be fused with a saturated or unsaturated, optionally substituted mono- or polycyclic ring system;

wherein the above-stated $C_{1-10}$ aliphatic groups may in each case be substituted with 1, 2, 3, 4 or 5 substituents mutually independently selected from the group consisting of F, Cl, Br, I, —CN, —NO₂, —OH, —O—$C_{1-5}$ alkyl, —SH, —S—$C_{1-5}$ alkyl, —NH₂, —NH—$C_{1-5}$ alkyl and —N($C_{1-5}$ alkyl)($C_{1-5}$ alkyl);

the above-stated cycloaliphatic groups may in each case be substituted with 1, 2, 3, 4 or 5 substituents mutually independently selected from the group consisting of oxo (=O), thioxo (=S), F, Cl, Br, I, —CN, —CF₃, —SF₅, —OH, —O—$C_{1-5}$ alkyl, —NH₂, —NO₂, —O—CF₃, —S—CF₃, —SH, —S—$C_{1-5}$ alkyl, —$C_{1-5}$ alkyl, —C(=O)—H, —C(=O)—$C_{1-5}$ alkyl, —C(=O)—OH, —C(=O)—O—$C_{1-5}$ alkyl, —(CH₂)—C(=O)—OH, —(CH₂)—C(=O)—O—$C_{1-5}$ alkyl, —NH—$C_{1-5}$ alkyl, —N($C_{1-5}$ alkyl)₂, —(CH₂)-benzo[b]furanyl, —O-phenyl, —O-benzyl, phenyl, benzyl, naphthyl and —(CH₂)-naphthyl, wherein in each case the cyclic moiety of the groups —O-phenyl, —O-benzyl, phenyl, —(CH₂)-benzo[b]furanyl, benzyl, naphthyl and —(CH₂)-naphthyl may be substituted with 1, 2, 3, 4 or 5 substituents mutually independently selected from the group consisting of F, Cl, Br, —OH, —CF₃, —SF₅, —CN, —NO₂, —O—$C_{1-5}$ alkyl, —$C_{1-5}$ alkyl, —O—CF₃, —S—CF₃, phenyl and —O-benzyl, and the above-stated cycloaliphatic groups may in each case optionally comprise 1, 2, 3, 4 or 5 heteroatom(s) mutually independently selected from the group consisting of oxygen, nitrogen and sulfur ring member(s);

the above-stated $C_{1-5}$ alkylene, $C_{2-5}$ alkenylene or $C_{2-5}$ alkynylene groups may in each case be substituted with 1, 2, 3, 4 or 5 substituents mutually independently selected from the group consisting of F, Cl, Br, —OH, —SH, —NH₂, —CN, NO₂ and phenyl, and the above-stated $C_{1-5}$ alkylene, $C_{2-5}$ alkenylene or $C_{2-5}$ alkynylene groups may optionally in each case comprise 1 or 2 heteroatom(s) selected from the group consisting of oxygen, nitrogen and sulfur as chain link(s);

the rings of the above-stated mono- or polycyclic ring systems may optionally in each case be substituted with 1, 2, 3, 4 or 5 substituents mutually independently selected from the group consisting of oxo (=O), thioxo (=S), F, Cl, Br, I, —CN, —CF₃, —SF₅, —OH, —O—$C_{1-5}$ alkyl, —O—$C_{2-5}$ alkenyl, —NH₂, —NO₂, —O—CF₃, —O—CHF₂, —O—CH₂F, —S—CF₃, —S—CHF₂, —S—CH₂F, —SH, —S—$C_{1-5}$ alkyl, —$C_{1-5}$ alkyl, —C(=O)—OH, —C(=O)—O—$C_{1-5}$ alkyl, —NH—$C_{1-5}$ alkyl, —N($C_{1-5}$ alkyl)₂, —NH—C(=O)—O—$C_{1-5}$ alkyl, —NH—C(=O)—$C_{1-5}$ alkyl, —C(=O)—H, —C(=O)—$C_{1-5}$ alkyl, —C(=O)—NH₂, —C(=O)—NH—$C_{1-5}$ alkyl, —C(=O)—N—($C_{1-5}$ alkyl)₂, —S(=O)₂—NH₂, —S(=O)₂—NH—$C_{1-5}$ alkyl, —(CH₂)-benzo[b]furanyl, —O-phenyl, —O—benzyl, phenyl and benzyl, wherein in each case the cyclic moiety of the groups —O-phenyl, —O-benzyl, phenyl, —(CH₂)-benzo[b]furanyl and benzyl may be substituted with 1, 2, 3, 4 or 5 substituents mutually independently selected from the group consisting of F, Cl, Br, —OH, —CF₃, —SF₅, —CN, —NO₂, —O—$C_{1-5}$ alkyl, —$C_{1-5}$ alkyl, —O—CF₃, —S—CF₃, phenyl and —O-benzyl, and the rings of the above-stated mono- or polycyclic ring systems are in each case 5-, 6- or 7-membered and may in each case comprise 1, 2, 3, 4 or 5 heteroatom(s) as ring member(s) which are mutually independently selected from the group consisting of oxygen, nitrogen and sulfur;

and the above-stated aryl or heteroaryl groups are in each case optionally substituted by 1, 2, 3, 4 or 5 substituents mutually independently selected from the group consisting of F, Cl, Br, I, —CN, —CF₃, —SF₅, —OH, —O—$C_{1-5}$ alkyl, —O—$C_{2-5}$ alkenyl, —NH₂, —NO₂, —O—CF₃, —O—CHF₂, —O—CH₂F, —S—CF₃, —S—CHF₂, —S—CH₂F, —SH, —S—$C_{1-5}$ alkyl, —$C_{1-5}$ alkyl, —C(=O)—O—$C_{1-5}$ alkyl, —NH—$C_{1-5}$ alkyl, —N($C_{1-5}$ alkyl)₂, —NH—C(=O)—O—$C_{1-5}$ alkyl, —NH—C(=O)—$C_{1-5}$ alkyl, —C(=O)—H, —C(=O)—$C_{1-5}$ alkyl, —C(=O)—NH₂, —C(=O)—NH—$C_{1-5}$ alkyl, —C(=O)—N—($C_{1-5}$ alkyl)₂, —S(=O)₂—NH₂, —S(=O)₂—NH—$C_{1-5}$ alkyl, —(CH₂)— benzo[b]furanyl, —O-phenyl, —O-benzyl, phenyl and benzyl, wherein in each case the cyclic moiety of the groups —O-phenyl, —O-benzyl, phenyl, —(CH₂)— benzo[b]furanyl and benzyl may be substituted with 1, 2, 3, 4 or 5 substituents mutually independently selected from the group consisting of F, Cl, Br, —OH, —CF₃, —SF₅, —CN, —NO₂, —O—$C_{1-5}$ alkyl, —$C_{1-5}$ alkyl, —O—CF₃, —S—CF₃, phenyl and —O-benzyl, and the above-stated heteroaryl groups may in each case comprise 1, 2, 3, 4 or 5 heteroatom(s) mutually independently selected from the group consisting of oxygen, nitrogen and sulfur as ring member(s);

or a corresponding salt thereof.

2. A compound according to claim 1, wherein said compound is in the form of a pure enantiomer or pure diastereomer or a racemic mixture.

3. A compound according to claim 1, wherein said compound is in the form of a mixture of stereoisomers.

4. A compound according to claim 1, wherein $R^1$ represents —(CHR⁴)—(CH₂)$_c$—(CH₂)$_d$—C(=O)—OR⁵ with c=0 or 1 and d=0 or 1;

—(CHR⁶)—(CHR⁷)$_e$—V$_f$—(CH₂)$_g$—W$_h$—(CH₂)$_i$R⁸ with e=0 or 1, f=0 or 1, g=0 or 1, h=0 or 1 and i=0 or 1, in which V and W mutually independently in each case represent O, S, NH, N(CH₃) or N(C₂H₅);

an alkyl group selected from the group consisting of methyl, ethyl, n-propyl, isopropyl, n-butyl, sec-butyl, isobutyl, tert-butyl, n-pentyl, sec-pentyl, —(CH₂)—(CH₂)—(C(CH₃)₃), n-hexyl, n-heptyl, n-octyl and —(CH₂)—(CH)(C₂H₅)—(CH₂)—(CH₂)—(CH₂)—

(CH$_3$), wherein the alkyl group may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, alkyl, —NH$_2$, —NH—C$_{1-5}$ alkyl and —N(C$_{1-5}$ alkyl)(C$_{1-5}$ alkyl);

an alkenyl group selected from the group consisting of vinyl, 1-propenyl, 2-propenyl, 1-butenyl, 2-butenyl and 3-butenyl, wherein the alkenyl-group may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);

an alkynyl group selected from the group consisting of ethynyl, 1-propynyl, 2-propynyl, 1-butynyl, 2-butynyl and 3-butynyl, wherein the alkynyl group may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);

a (hetero)cycloaliphatic group selected from the group consisting of cyclopropyl, cyclobutyl, cyclopentyl, cyclohexyl, cycloheptyl, (6,6)-dimethyl-[3.1.1]-bicycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, wherein the (hetero)cycloaliphatic group may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—OH, —C(=O)—O—C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —(CH$_2$)-benzo[b]furanyl, —O-phenyl, —O-benzyl, phenyl, benzyl, naphthyl and —(CH$_2$)-naphthyl, wherein in each case the cyclic moiety of the groups —O-phenyl, —O-benzyl, phenyl, —(CH$_2$)— benzo[b]furanyl, benzyl, naphthyl and —(CH$_2$)-naphthyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

or a group selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrimidinyl, indazolyl, quinazolinyl, quinolinyl and isoquinolinyl, wherein the group may in each case be substituted with 1, 2, 3, 4 or 5 substituents mutually independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—O—C$_{1-5}$ alkyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —S(=O)$_2$—NH$_2$, —S(=O)$_2$—NH—C$_{1-5}$ alkyl, —(CH$_2$)-benzo[b]furanyl, —O-phenyl, —O-benzyl, phenyl and benzyl, wherein in each case the cyclic moiety of the groups —O-phenyl, —O-benzyl, phenyl, —(CH$_2$)— benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

$R^2$ represents hydrogen;

—(CH$_2$)—R$^9$ or an alkyl group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

or $R^1$ and $R^2$, together with the nitrogen atom joining them together as a ring member, form a heterocycloaliphatic group selected from the group consisting of imidazolidinyl, (1,3)-thiazolidinyl, piperazinyl, morpholinyl, thiomorpholinyl, pyrrolidinyl; piperidinyl; (1,2,3,6)-tetrahydropyridinyl and (1,2,3,4)-tetrahydropyridinyl, wherein the heterocycloaliphatic group may in each case be substituted with 1, 2 or 3 substituents mutually independently selected from the group consisting of R$^{10}$, —C(=O)—R$^{11}$ and —(CH$_2$)—NH—C(=O)—R$^{12}$;

$R^3$ represents —C(=O)—NR$^{13}$R$^{14}$;

—C(=O)—R$^{15}$;

—C(=O)—(CH$_2$)—X—(CH$_2$)—C(=O)—OR$^{16}$, —C(=O)—X—(CH$_2$)—C(=O)—OR$^{16}$ or —C(=O)—(CH$_2$)—(CH$_2$)—(CH$_2$)—C(=O)—OR$^{16}$, in which X represents O, S, NH, N(CH$_3$), N(C$_2$H$_5$) or CR$^{17}$R$^{18}$;

—C(=O)—(CHR$^{19}$)—NH—C(=O)—OR$^{20}$;

—C(=O)—(CH$_2$)—R$^{21}$, —C(=O)—(CH$_2$)—Y—R$^{21}$, —C(=O)—(CH$_2$)—Y—(CH$_2$)—R$^{21}$ or —C(=O)—(CH$_2$)—(CH$_2$)—(CH$_2$)—Y—R$^{21}$, in which Y represents O, S, NH, N(CH$_3$) or N(C$_2$H$_5$);

—C(=O)—(CH=CH)—R$^{22}$;

—S(=O)$_2$—R$^{23}$;

—S(=O)$_2$—NR$^{24}$R$^{25}$;

—C(=S)—NR$^{26}$—R$^{27}$, —C(=S)—NR$^{26}$—(CH$_2$)—R$^{27}$, —C(=S)—NR$^{26}$—(CH$_2$)—(CH$_2$)—R$^{27}$ or —C(=S)—NR$^{26}$—(CH$_2$)—(CH$_2$)—Z—R$^{27}$, in which Z represents O, S, NH, N(CH$_3$) or N(C$_2$H$_5$);

—C(=S)—NR$^{26}$—(CHR$^{28}$)—R$^{29}$;

—C(=S)—NR$^{26}$—C(=O)—R$^{30}$;

or —(CH$_2$)—R$^{31}$;

$R^4$ represents —C(=O)—NH$_2$;
hydrogen;
an alkyl group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl group may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);
or an alkenyl group selected from the group consisting of vinyl, 1-propenyl, 2-propenyl, 1-butenyl, 2-butenyl and 3-butenyl, wherein the alkenyl group may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);

$R^5$, $R^{17}$, $R^{18}$, $R^{24}$ and $R^{25}$, mutually independently, in each case represent an alkyl group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CHs, —NH—C$_2$H$_5$, —N(CH$_3$)$_2$, —N(C$_2$H$_5$)$_2$ and —N(CH$_3$)(C$_2$H$_5$),
or an alkenyl group selected from the group consisting of vinyl, 1-propenyl, 2-propenyl, 1-butenyl, 2-butenyl and 3-butenyl, wherein the alkenyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CHs, —NH—C$_2$H$_5$, —N(CH$_3$)$_2$, —N(C$_2$H$_5$)$_2$ and —N(CH$_3$)(C$_2$H$_5$);

$R^6$, $R^7$, $R^{13}$, $R^{16}$ and $R^{26}$, mutually independently, in each case represent hydrogen;
an alkyl group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CHs, —NH—C$_2$H$_5$, —N(CH$_3$)$_2$, —N(C$_2$H$_5$)$_2$ and —N(CH$_3$)(C$_2$H$_5$),
or an alkenyl group selected from the group consisting of vinyl, 1-propenyl, 2-propenyl, 1-butenyl, 2-butenyl and 3-butenyl, wherein the alkenyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

$R^8$, $R^9$, $R^{21}$, $R^{22}$, $R^{23}$, $R^{30}$ and $R^{31}$, mutually independently, in each case represent
a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, wherein the (hetero)cycloaliphatic group may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—OH, —C(=O)—O—C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —(CH$_2$)-benzo[b]furanyl, —O-phenyl, —O-benzyl, phenyl, benzyl, naphthyl and —(CH$_2$)-naphthyl, wherein in each case the cyclic moiety of the groups —O-phenyl, —O-benzyl, phenyl, —(CH$_2$)-benzo[b]furanyl, benzyl, naphthyl and —(CH$_2$)— naphthyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;
or a group selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrimidinyl, indazolyl, quinazolinyl, quinolinyl and isoquinolinyl, wherein the group may in each case be substituted with 1, 2, 3, 4 or 5 substituents mutually independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, alkyl, —C$_{1-5}$ alkyl, —C(=O)—O—C$_{1-5}$ alkyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —S(=O)$_2$—NH$_2$, —S(=O)$_2$—NH—C$_{1-5}$ alkyl, —(CH$_2$)-benzo[b]furanyl, —O-phenyl, —O-benzyl, phenyl and benzyl, wherein in each case the cyclic moiety of the groups —O-phenyl, —O-benzyl, phenyl, —(CH$_2$)— benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

$R^{10}$, $R^{11}$, $R^{12}$, $R^{14}$ and $R^{20}$, mutually independently, in each case represent
an alkyl group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl group may in each case be substituted with 1, 2, 3, 4 or 5 substituents mutually independently selected from the group consisting of F, Cl, Br, I, —CN, —NO$_2$, —OH, —O—C$_{1-5}$ alkyl, —SH, —S—C$_{1-5}$ alkyl, —NH$_2$, —NH—C$_{1-5}$ alkyl and —N(C$_{1-5}$ alkyl)(C$_{1-5}$ alkyl);

a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl and indenyl, wherein the (hetero)cycloaliphatic group may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—OH, —C(=O)-β-C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —(CH$_2$)-benzo[b]furanyl, —O-phenyl, —O-benzyl, phenyl, benzyl, naphthyl and —(CH$_2$)-naphthyl, wherein in each case the cyclic moiety of the substituents —O-phenyl, —O-benzyl, phenyl, —(CH$_2$)-benzo[b]furanyl, benzyl, naphthyl and —(CH$_2$)-naphthyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —C$_{1-5}$ alkyl, —S—CF$_3$, phenyl and —O-benzyl and/or wherein the (hetero)cycloaliphatic group may be attached via a —(CH$_2$)—, —CH(CH$_3$)—, —(CH$_2$)—(CH$_2$)—, —(CH$_2$)—(CH$_2$)—(CH$_2$)— or —(CH$_2$)—(CH=CH)-group;

or a group selected from the group consisting of phenyl, naphthyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrimidinyl, indazolyl, quinazolinyl, quinolinyl, isoquinolinyl and thieno[2,3-d]pyrimidinyl, wherein the group may in each case be substituted with 1, 2, 3, 4 or 5 substituents mutually independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—O—C$_{1-5}$ alkyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —S(=O)$_2$—NH$_2$, —S(=O)$_2$—NH—C$_{1-5}$ alkyl, —(CH$_2$)-benzo[b]furanyl, —O-phenyl, —O-benzyl, phenyl and benzyl and/or be attached via a —(CH$_2$)—, —CH(CH$_3$)—, —(CH$_2$)—(CH$_2$)—, —(CH$_2$)—(CH$_2$)—(CH$_2$)— or —(CH$_2$)—(CH=CH)— group, wherein in each case the cyclic moiety of the substituents —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

R$^{15}$ and R$^{27}$, mutually independently, in each case represent an alkyl group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

an alkenyl group selected from the group consisting of vinyl, 1-propenyl, 2-propenyl, 1-butenyl, 2-butenyl and 3-butenyl, wherein the alkenyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl and 7,7-dimethyl-2-oxa-bicyclo[2.2.1]heptyl, wherein the (hetero)cycloaliphatic group may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—OH, —C(=O)—O—C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —O-phenyl, —O-benzyl, phenyl and benzyl, wherein in each case the cyclic moiety of the groups —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

or a group selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrimidinyl, indazolyl, quinazolinyl, quinolinyl and isoquinolinyl, wherein the group may in each case be substituted with 1, 2, 3, 4 or 5 substituents mutually independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—O—C$_{1-5}$ alkyl, —NH—C$_{1-5}$ alkyl, —N(C$_{1-5}$ alkyl)$_2$, —NH—C(=O)—O—

C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —S(=O)$_2$—NH$_2$, —S(=O)$_2$—NH—C$_{1-5}$ alkyl, —O-phenyl, —O-benzyl, phenyl and benzyl, wherein in each case the cyclic moiety of the groups —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

R$^{19}$ represents a group selected from the group consisting of phenyl, naphthyl, thiophenyl, furanyl and pyridinyl, wherein the group may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —NH$_2$—, —NO$_2$, —O—CF$_3$, —O—CHF$_2$, —O—CH$_2$F, —S—CF$_3$, —S—CHF$_2$, —S—CH$_2$F, —SH, —S—CHs, —S—C$_2$H$_5$, methyl, ethyl, n-propyl, isopropyl, n-butyl, sec-butyl, isobutyl, tert-butyl, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —NH—C(=O)—CHs, —NH—C(=O)—C$_2$H$_5$, —C(=O)—H, —C(=O)—CHs, —C(=O)—C$_2$H$_5$, —C(=O)—NH$_2$, —C(=O)—NH—CHs, —C(=O)—N—(CH$_3$)$_2$, phenyl and benzyl and/or be attached via a —(CH$_2$)—, —(CH$_2$)—(CH$_2$)— or —(CH$_2$)—O—(CH$_2$)— group;

and

R$^{28}$ and R$^{29}$, mutually independently, in each case represent an alkyl group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CHs, —NH—C$_2$H$_5$, —N(CH$_3$)$_2$, —N(C$_2$H$_5$)$_2$ and —N(CH$_3$)(C$_2$H$_5$);

or a group selected from the group consisting of phenyl, naphthyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrimidinyl, indazolyl, quinazolinyl, quinolinyl and isoquinolinyl, wherein the group may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, -5-C$_2$H$_5$, methyl, ethyl, n-propyl, isopropyl, n-butyl, sec-butyl, isobutyl, tert-butyl, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —NH—C(=O)—CHs, —NH—C(=O)—C$_2$H$_5$, —C(=O)—H, —C(=O)—CH$_3$, —C(=O)—C$_2$H$_5$, —C(=O)—NH$_2$, —C(=O)—NH—CH$_3$, —C(=O)—N—(CH$_3$)$_2$, —S(=O)$_2$—NH$_2$, —S(=O)$_2$—CH$_3$, phenyl and benzyl;

or a corresponding salt thereof.

5. A compound according to claim 1, wherein

R$^1$ represents —(CHR$^4$)—C(=O)—OR$^5$, —(CHR$^4$)—(CH$_2$)—C(=O)—OR$^5$ or —(CHR$^4$)—(CH$_2$)—(CH$_2$)—C(=O)—OR$^6$;

—(CHR$^6$)—R$^8$, —(CHR$^6$)—(CHR$^7$)—R$^8$, —(CHR$^6$)—(CHR$^7$)—V—R$^8$, —(CHR$^6$)—(CHR$^7$)—(CH$_2$)—R$^8$, —(CHR$^6$)—(CHR$^7$)—(CH$_2$)—W—R$^8$ or —(CHR$^6$)—(CHR$^7$)—(CH$_2$)—W—(CH$_2$)—R$^8$, in which V and W mutually independently in each case represent O, S, NH, N(CH$_3$) or N(C$_2$H$_5$);

an alkyl group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$), wherein the alkyl group may in each case be substituted with 1, 2, 3, 4 or 5 substituents mutually independently selected from the group consisting of F, Cl, Br, I, —CN, —NO$_2$, —OH, —O—CH$_3$, —O—C$_2$H$_5$, —SH, —S—CH$_3$, —S—C$_2$H$_5$, —NH$_2$, —NH—CH$_3$, —NH—C$_2$H$_5$, —N(CH$_3$)$_2$, —N(C$_2$H$_5$)$_2$ and —N(CH$_3$)(C$_2$H$_5$);

an alkynyl group selected from the group consisting of ethynyl, 1-propynyl, 2-propynyl, 1-butynyl, 2-butynyl and 3-butynyl;

a (hetero)cycloaliphatic group selected from the group consisting of cyclopropyl, cyclobutyl, cyclopentyl, cyclohexyl, cycloheptyl, (6,6)-dimethyl-[3.1.1]-bicycloheptyl, pyrrolidinyl, piperidinyl, morpholinyl, thiomorpholinyl, indanyl and indenyl, wherein the (hetero)cycloaliphatic group may in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —CO=O)—H, —CO=O)—CH$_3$, —C(=O)—C$_2$H$_5$, —C(=O)—C(CH$_3$)$_3$, —C(=O)—OH, —C(=O)—O—CH$_3$, —C(=O)—O—C$_2$H$_5$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), —(CH$_2$)-benzo[b]furanyl, —O-phenyl, —O-benzyl, phenyl, benzyl, naphthyl and —(CH$_2$)-naphthyl, wherein the cyclic moiety of the benzyl group may be substituted with 1, 2, 3, 4 or 5 substituents mutually independently selected from the group consisting of F, Cl, Br, —OH, —CF$_3$, —SF$_5$, —CN, —NO$_2$, —O—CH$_3$, —O—C$_2$H$_5$ and —O—CF$_3$, or a group selected from the group consisting of phenyl, naphthyl, (1,3)-benzodioxolyl, (1,4)-benzodioxanyl, thiophenyl, furanyl, pyridinyl, imidazolyl and indolyl, wherein the group may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —O—CHF$_2$, —O—CH$_2$F, —S—CF$_3$, —S—CHF$_2$, —S—CH$_2$F, —SH, methyl, ethyl, n-propyl, isopropyl, n-butyl, sec-butyl, isobutyl and tert-butyl;

R² represents hydrogen or
—(CH₂)—R⁹,
or
R¹ and R², together with the nitrogen atom joining them together as a ring member, form a group which is selected from the group consisting of

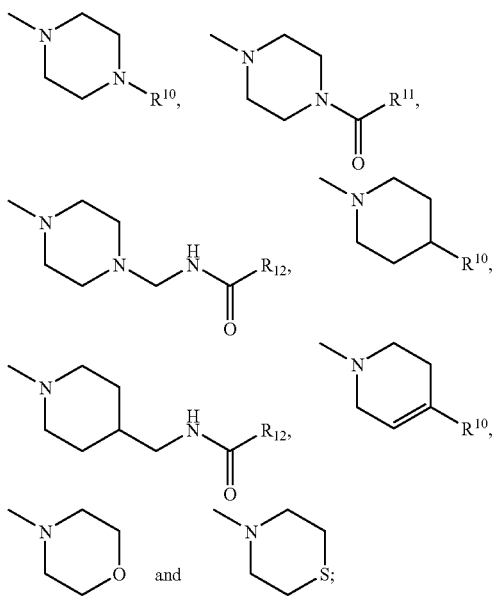

R³ represents —C(=O)—NR¹³R¹⁴;
—C(=O)—R¹⁵;
—C(=O)—(CH₂)—O—(CH₂)—C(=O)—OR⁶,
—C(=O)—(CH₂)—CR¹⁷R¹⁸—(CH₂)—C(=O)—OR¹⁶, —C(=O)—CR¹⁷R¹⁸—(CH₂)—C(=O)—OR¹⁶ or —C(=O)—(CH₂)—(CH₂)—(CH₂)—C(=O)—OR¹⁶;
—C(=O)—(CHR¹⁹)—NH—C(=O)—OR²⁰;
—C(=O)—(CH₂)—R²¹, —C(=O)—(CH₂)—O—R²¹, —C(=O)—(CH₂)—O—(CH₂)—R²¹ or —C(=O)—(CH₂)—(CH₂)—(CH₂)—O—R²¹;
—C(=O)—(CH=CH)—R²²;
—S(=O)₂—R²³;
—S(=O)₂—NR²⁴R²⁵;
—C(=S)—NR²⁶—R²⁷, —C(=S)—NR²⁶—(CH₂)—R²⁷, —C(=S)—NR²⁶—(CH₂)—(CH₂)—R²⁷ or —C(=S)—NR²⁶—(CH₂)—(CH₂)—O—R²⁷;
—C(=S)—NR²⁶—(CHR²⁸)—R²⁹;
—C(=S)—NR²⁶—C(=O)—R³⁰;
or —(CH₂)—R³¹;
R⁴ represents —C(=O)—NH₂;
hydrogen or
an alkyl group selected from the group consisting of methyl, ethyl, n-propyl, isopropyl, n-butyl, sec-butyl, isobutyl, tert-butyl, n-pentyl, sec-pentyl, —(CH₂)—(CH₂)—(C(CH₃)₃), n-hexyl, n-heptyl, n-octyl and —(CH₂)—(CH)(C₂H₅)—(CH₂)—(CH₂)—(CH₂)—(CH₃), wherein the alkyl group may in each case be substituted with 1, 2, 3, 4 or 5 substituents mutually independently selected from the group consisting of F, Cl, Br, I, —CN, —NO₂, —OH, —O—CH₃, —O—C₂H₅, —SH, —S—CH₃, —S—C₂H₅, —NH₂, —NH—CH₃, —NH—C₂H₅, —N(CH₃)₂, —N(C₂H₅)₂ and —N(CH₃)(C₂H₅));

R⁵ represents an alkyl group selected from the group consisting of methyl, ethyl, n-propyl, isopropyl, n-butyl, sec-butyl, isobutyl and tert-butyl;
R⁶, R⁷ and R¹⁶, mutually independently, in each case represent
hydrogen or an alkyl group selected from the group consisting of methyl, ethyl, n-propyl and isopropyl;
R⁸, R⁹, R²¹, R²², R²³, R³⁰ and R³¹, mutually independently, in each case represent
a (hetero)cycloaliphatic group selected from the group consisting of cyclopropyl, cyclobutyl, cyclopentyl, cyclohexyl, cycloheptyl, pyrrolidinyl, piperidinyl, morpholinyl, thiomorpholinyl, indanyl and indenyl, wherein the (hetero)cycloaliphatic group may in each case be substituted with 1, 2, 3, 4 or 5 substituents mutually independently selected from the group consisting of oxo (=O), thioxo (=S), F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, -isopropyl, n-butyl, sec-butyl, isobutyl, tert-butyl, —C(=O)—H, —C(=O)—CH₃, —C(=O)—C₂H₅, —C(=O)—C(CH₃)₃, —C(=O)—OH, —C(=O)—O—CH₃, —C(=O)—O—C₂H₅, —(CH₂)—C(=O)—OH, —(CH₂)—C(=O)—O—CH₃, —(CH₂)—C(=O)—O—C₂H₅, —N(CH₃)₂, —N(C₂H₅)₂, —N(H)(CH₃), —N(H)(C₂H₅), phenyl and benzyl;
or a group selected from the group consisting of phenyl, naphthyl, (1,3)-benzodioxolyl, (1,4)-benzodioxanyl, thiophenyl, furanyl, pyridinyl, imidazolyl, indolyl and isoindolyl, wherein the group may in each case be substituted with 1, 2, 3, 4 or 5 substituents mutually independently selected from the group consisting of F, Cl, Br, I, —CN, —CF₃, —SF₅, —OH, —O—CH₃, —O—C₂H₅, —O—CH(CH₃)₂, —O—CH₂—CH₂—CH₂—CH₃, —O—CH₂—CH=CH₂, —NH₂, —NO₂, —O—CF₃, —O—CHF₂, —O—CH₂F, —S—CF₃, —S—CHF₂, —S—CH₂F, —SH, —S—CH₃, —S—C₂H₅, methyl, ethyl, n-propyl, isopropyl, n-butyl, sec-butyl, isobutyl, tert-butyl, —(CH₂)—C(=O)—O—CH₃, —(CH₂)—C(=O)—O—C₂H₅, —N(CH₃)₂, —N(C₂H₅)₂, —N(H)(CH₃), —N(H)(C₂H₅), —C(=O)—H, —C(=O)—CH₃, —C(=O)—C₂H₅, —C(=O)—NH₂, —S(=O)₂—NH₂, —S(=O)₂—NH—CH₃, —O-phenyl, —O-benzyl, phenyl and benzyl;
R¹⁰, R¹¹, R¹², R¹⁴ and R²⁰, mutually independently, in each case represent
an alkyl group selected from the group consisting of methyl, ethyl, n-propyl, isopropyl, n-butyl, sec-butyl, isobutyl, tert-butyl, n-pentyl, sec-pentyl, —(CH₂)—(CH₂)(C(CH₃)₃), n-hexyl, n-heptyl and n-octyl, wherein the alkyl group may in each case be substituted with 1, 2, 3, 4 or 5 substituents mutually independently selected from the group consisting of —N(CH₃)₂, —N(C₂H₅)₂, F, Cl and Br;
a cycloaliphatic group selected from the group consisting of pyrrolidinyl, piperidinyl, piperazinyl, morpholinyl, cyclopropyl, cyclobutyl, cyclopentyl and cyclohexyl, wherein the cycloaliphatic group may in each case be substituted with 1, 2 or 3 substituents mutually independently selected from the group consisting of F, Cl, Br, I, —CN, —CF₃, —SF₅, —OH, —O—CH₃, —O—C₂H₅, —NH₂, —NO₂, —O—CF₃, —S—CF₃, —SH, —S—CH₃, —S—C₂H₅, methyl, ethyl, n-propyl, isopropyl, n-butyl, sec-butyl, isobutyl, tert-butyl, —C(=O)—H, —C(=O)—CH$_s$, —C(=O)—C$_2$H$_5$, —C(=O)—C(CH$_3$)$_3$, —C(=O)—OH, —C(=O)—O—CH$_3$, —C(=O)-β-C$_2$H$_5$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), phenyl and benzyl substituted and/or be attached via a —(CH$_2$)— or —(CH$_2$)—(CH$_2$)— group;

or a group selected from the group consisting of phenyl, naphthyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrimidinyl, indazolyl, quinazolinyl, quinolinyl, isoquinolinyl and thieno[2,3-d]pyrimidinyl, wherein the group may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_s$, —S—C$_2$H$_5$, methyl, ethyl, n-propyl, isopropyl, n-butyl, sec-butyl, isobutyl, tert-butyl, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —C(=O)—H, —C(=O)—CH$_s$, —C(=O)—C$_2$H$_5$, —C(=O)—NH$_2$, —C(=O)—NH—CH$_s$, —C(=O)—N—(CH$_3$)$_2$, —S(=O)$_2$—NH$_2$, —S(=O)$_2$—CH$_3$, phenyl and benzyl and/or be attached via a —(CH$_2$)—, —CH(CH$_3$)—, —(CH$_2$)—(CH$_2$)—, —(CH$_2$)—(CH$_2$)—(CH$_2$)— or —(CH$_2$)—(CH=CH)— group;

R$^{13}$ and R$^{26}$ represent hydrogen;

R$^{15}$ and R$^{27}$, mutually independently, in each case represent a group selected from the group consisting of methyl, ethyl, n-propyl, isopropyl, n-butyl, sec-butyl, isobutyl, tert-butyl, vinyl, 1-propenyl, 2-propenyl, 1-butenyl, 2-butenyl and 3-butenyl;

a (hetero)cycloaliphatic group selected from the group consisting of cyclopropyl, cyclobutyl, cyclopentyl, cyclohexyl and 7,7-dimethyl-2-oxa-bicyclo[2.2.1]heptyl, wherein the (hetero)cycloaliphatic group may in each case be substituted with 1, 2 or 3 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_s$, —S—C$_2$H$_5$, methyl, ethyl, n-propyl, isopropyl, n-butyl, sec-butyl, isobutyl, tert-butyl, —C(=O)—H, —C(=O)—CH$_3$, —C(=O)—C$_2$H$_5$, —C(=O)—C(CH$_3$)$_3$, —C(=O)—OH, —C(=O)—O—CH$_3$, —C(=O)—O—C$_2$H$_5$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), phenyl and benzyl;

or a group selected from the group consisting of phenyl, naphthyl, thiophenyl, furanyl, pyrrolyl, pyrazolyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, wherein the group may in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, methyl, ethyl, n-propyl, isopropyl, n-butyl, sec-butyl, isobutyl, tert-butyl, —C(=O)—O—CH$_3$, —C(=O)—O—C$_2$H$_5$, —N(CH$_3$)$_2$, —N(C$_2$H$_5$)$_2$, —N(H)(CH$_3$), —N(H)(C$_2$H$_5$), —NH—C(=O)—CH$_s$, —NH—C(=O)—C$_2$H$_5$, —C(=O)—H, —C(=O)—CH$_s$, —C(=O)—C$_2$H$_5$, —C(=O)—NH$_2$, —C(=O)—NH—CH$_3$, —C(=O)—N—(CH$_3$)$_2$, —S(=O)$_2$—NH$_2$, —S(=O)$_2$—CH$_3$, phenyl and benzyl;

R$^{17}$ and R$^{18}$, mutually independently, in each case represent a methyl or ethyl group;

R$^{19}$ represents a phenyl group, which may be attached via a —(CH$_2$)—, —(CH$_2$)—(CH$_2$)— or —(CH$_2$)—O—(CH$_2$)— group;

R$^{24}$ and R$^{25}$, mutually independently, in each case represent a methyl or ethyl group;

R$^{28}$ represents a phenyl group, which may be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_s$, —S—C$_2$H$_5$, methyl, ethyl, n-propyl, isopropyl, n-butyl, sec-butyl, isobutyl, tert-butyl;

and

R$^{29}$ represents an alkyl group selected from the group consisting of methyl, ethyl, n-propyl, isopropyl, n-butyl, isobutyl and tert-butyl;

or a corresponding salt thereof.

6. A compound according to claim 1, wherein

R$^1$ represents —(CHR$^4$)—C(=O)—OR$^5$, —(CHR$^4$)—(CH$_2$)—C(=O)—OR$^5$ or —(CHR$^4$)—(CH$_2$)—(CH$_2$)—C(=O)—OR$^5$;

—(CHR$^6$)—R$^8$, —(CHR$^6$)—(CHR$^7$)—R$^8$, —(CHR$^8$)—(CHR$^7$)—O—R$^8$, —(CHR$^8$)—(CHR$^7$)—(CH$_2$)—R$^8$ or —(CHR$^6$)—(CHR$^7$)—(CH$_2$)—N(CH$_3$)—R$^8$;

an optionally substituted alkyl group selected from the group consisting of methyl, ethyl, n-propyl, isopropyl, —(CH$_2$)—(CH$_2$)—CN, —(CH$_2$)—(CH$_2$)—N(CH$_3$)$_2$, —(CH$_2$)—(CH$_2$)—O—CH$_3$, —(CH$_2$)—(CH$_2$)—S—C$_2$H$_5$, n-butyl, sec-butyl, isobutyl, tert-butyl, —(CH$_2$)—(CH$_2$)—(CH$_2$)—O—CH$_s$, n-pentyl, sec-pentyl —(CH$_2$)—(CH$_2$)(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$);

an alkynyl group selected from the group consisting of 1-propynyl and 2-propynyl;

a cycloaliphatic group selected from the group consisting of cyclopropyl, cyclobutyl, cyclopentyl, cyclohexyl, cycloheptyl, (6,6)-dimethyl-[3.1.1]-bicycloheptyl, indanyl and indenyl, wherein the cycloaliphatic group may in each case be substituted with an —O-benzyl group or a methyl group, a pyrrolidinyl or piperidinyl group, which may in each case be substituted on the nitrogen atom with a substituent selected from the group consisting of —C(=O)—CH$_s$, —C(=O)—C$_2$H$_5$, —C(=O)—C(CH$_3$)$_3$, —C(=O)—O—C$_2$H$_5$, benzyl and —(CH$_2$)-naphthyl, wherein the cyclic moiety of the benzyl group may be substituted with 1, 2 or 3 substituents mutually independently selected from the group consisting of F, Cl, Br, —CF$_3$ and —O—CF$_3$,
or a phenyl group, which may be substituted with 1, 2 or 3 substituents mutually independently selected from the group consisting of —O—CH$_3$, —O—C$_2$H$_5$, methyl, ethyl, n-propyl, isopropyl, n-butyl, sec-butyl, isobutyl and tert-butyl;

$R^2$ represents hydrogen or
—(CH$_3$)—R$^5$;
or
$R^1$ and $R^2$, together with the nitrogen atom joining them together as a ring member, form a group which is selected from the group consisting of

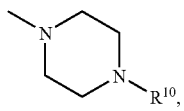 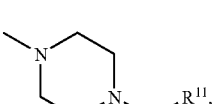

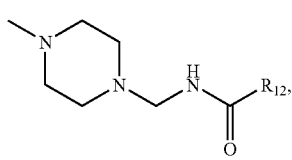

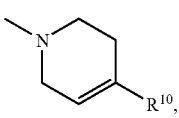

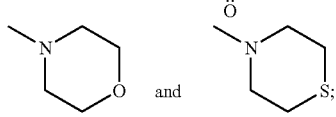

$R^3$ represents —C(=O)—NR$^{13}$R$^{14}$;
—C(=O)—R$^{15}$;
—C(=O)—(CH$_2$)—O—(CH$_2$)—C(=O)—OR$^{16}$,
—C(=O)—(CH$_2$)—CR$^{17}$R$^{18}$—(CH$_2$)—C(=O)—OR$^{16}$,   —C(=O)—CR$^{17}$R$^{18}$—(CH$_2$)—C(=O)—OR$^{16}$  or  —C(=O)—(CH$_2$)—(CH$_2$)—(CH$_2$)—C(=O)—OR$^{16}$;
—C(=O)—(CHR$^{19}$)—NH—C(=O)—OR$^{20}$;
—C(=O)—(CH$_2$)—R$^{21}$,   —C(=O)—(CH$_2$)—O—R$^{21}$, —C(=O)—(CH$_2$)—O—(CH$_2$)—R$^{21}$ or
—C(=O)—(CH$_2$)—(CH$_2$)—(CH$_2$)—O—R$^{23}$;
—C(=O)—(CH=CH)—R$^{22}$;
—S(=O)$_2$—R$^{23}$;
—S(=O)$_2$—NR$^{24}$R$^{25}$;
—C(=S)—NR$^{26}$—R$^{27}$,   —C(=S)—NR$^{26}$—(CH$_2$)—R$^{27}$,   —C(=S)—NR$^{26}$—(CH$_2$)—(CH$_2$)—R$^{27}$ or —C(=S)—NR$^{26}$—(CH$_2$)—(CH$_2$)—O—R$^{27}$;
—C(=S)—NR$^{26}$—(CHR$^{28}$)—R$^{29}$;
—C(=S)—NR$^{26}$—C(=O)—R$^{30}$; or —(CH$_2$)—R$^{31}$;

$R^4$ represents —C(=O)—NH$_2$;
hydrogen; or
an alkyl group selected from the group consisting of methyl, ethyl, n-propyl, isopropyl and n-butyl;

$R^5$ represents an alkyl group selected from the group consisting of methyl, ethyl, n-propyl, isopropyl, n-butyl, sec-butyl, isobutyl and tert-butyl;

$R^6$, $R^7$ and $R^{16}$, mutually independently, in each case represent hydrogen or an alkyl group selected from the group consisting of methyl, ethyl, n-propyl and isopropyl;

$R^8$ represents a (hetero)cycloaliphatic group selected from the group consisting of cyclopropyl, cyclobutyl, cyclopentyl, cyclohexyl, pyrrolidinyl, piperidinyl, morpholinyl and thiomorpholinyl
or a group selected from the group consisting of phenyl, naphthyl, thiophenyl, furanyl, pyridinyl and indolyl, wherein the group may in each case be substituted with 1, 2 or 3 substituents mutually independently selected from the group consisting of F, Cl, Br, —CF$_3$, —O—CH$_3$, —O—C$_2$H$_5$, —O—CH$_2$—CH=CH$_2$, methyl, ethyl, n-propyl, isopropyl, n-butyl, tert-butyl, —S—CH$_3$, —S—C$_2$H$_5$, —S(=O)$_2$—NH$_2$ and —S(=O)$_2$—NH—CH$_3$;

$R^9$ represents a group selected from the group consisting of phenyl, naphthyl, thiophenyl, furanyl and pyridinyl;

$R^{10}$ represents an optionally substituted alkyl group selected from the group consisting of —(CH$_2$)—N(CH$_3$)$_2$,   —(CH$_2$)—(CH$_2$)—N(CH$_3$)$_2$,   —(CH$_2$)—(CH$_2$)—(CH$_2$)—N(CH$_3$)$_2$,   —(CH$_2$)—N(C$_2$H$_5$)$_2$, —(CH$_2$)—(CH$_2$)—N(C$_2$H$_5$)$_2$ and —(CH$_2$)—(CH$_2$)—(CH$_2$)—N(C$_2$H$_5$)$_2$;
a cycloaliphatic group selected from the group consisting of piperazinyl, pyrrolidinyl, piperidinyl, morpholinyl, cyclopropyl, cyclobutyl, cyclopentyl and cyclohexyl, wherein the cycloaliphatic group may be attached via a —(CH$_2$)— or —(CH$_2$)—(CH$_2$)— or —(CH$_2$)—(CH$_2$)—(CH$_2$)— group;
or a group selected from the group consisting of thiazolyl, phenyl, naphthyl and thieno[2,3-d]pyrimidinyl, wherein the group may in each case be substituted with 1, 2 or 3 substituents mutually independently selected from the group consisting of F, Cl, Br, methyl, ethyl, n-propyl, —C(=O)—CHs and —C(=O)—C$_2$H$_5$ and/or be attached via a —(CH$_2$)—, —CH(CH$_3$)—, —(CH$_2$)—(CH$_2$)—, —(CH$_2$)—(CH$_2$)—(CH$_2$)—  or —(CH$_2$)—(CH=CH)— group;

$R^{11}$ represents an optionally substituted alkyl group selected from the group consisting of methyl, ethyl, n-propyl, —CF$_3$ and —CF$_2$—CF$_3$,
or a group selected from the group consisting of phenyl, and naphthyl, wherein the group may in each case be substituted with 1, 2 or 3 substituents mutually independently selected from the group consisting of F, Cl and Br and/or be attached via a —(CH$_2$)— or —(CH$_2$)—(CH$_2$)— group;

$R^{12}$ represents an optionally substituted alkyl group selected from the group consisting of methyl, ethyl, n-propyl, —CF$_3$ and —CF$_2$—CF$_3$;

$R^{13}$ represents hydrogen;

$R^{14}$ represents a group selected from the group consisting of phenyl and naphthyl, wherein the group may in each case be substituted with 1, 2 or 3 substituents mutually independently selected from the group consisting of F, Cl, Br, —CN, —CF$_3$, —O—CH$_3$, —O—C$_2$H$_5$, —O—CH(CH$_3$)$_2$,   —O—CH$_2$—CH$_2$—CH$_2$—CH$_3$, —NO$_2$, —O—CF$_3$, —O—CHF$_2$, —O—CH$_2$F, —S—CF$_3$, —S—CHF$_2$, —S—CH$_2$F, methyl, ethyl, n-propyl, isopropyl, n-butyl, sec-butyl, isobutyl, tert-butyl,   —C(=O)—O—CH$_3$,   —C(=O)-β-C$_2$H$_5$, —C(=O)—CH$_3$ and —C(=O)—C$_2$H$_5$ and/or be attached via a —(CH$_2$)—, —CH(CH$_3$)— or —(CH$_2$)—(CH$_2$)— group;

$R^{15}$ represents a group selected from the group consisting of 1-butenyl, 2-butenyl and 3-butenyl;
a 4,7,7-trimethyl-3-oxo-2-oxa-bicyclo[2.2.1]heptyl group or a group selected from the group consisting of phenyl, naphthyl, thiophenyl, furanyl, triazolyl, pyridinyl, pyrazolyl, quinolinyl and isoquinolinyl, wherein the group may in each case be substituted with 1, 2 or 3 substituents mutually independently selected from the group consisting of F, Cl, Br, —$CF_3$, —O—$CH_s$, —O—$C_2H_5$, —O—$CH(CH_3)_2$, —O—$CH_2$—$CH_2$—$CH_2$—$CH_3$, —O—$CF_3$, —O—$CHF_2$, —O—$CH_2F$, —S—$CF_3$, —S—$CHF_2$, —S—$CH_2F$, methyl, ethyl, n-propyl, isopropyl, n-butyl, sec-butyl, isobutyl, tert-butyl, phenyl, —NH—C(=O)—$CH_3$ and —NH—C(=O)—$C_2H_5$;

$R^{17}$ and $R^{18}$, mutually independently, in each case represent a methyl or ethyl group;

$R^{19}$ represents a phenyl group, which may be attached via a —$(CH_2)$—, —$(CH_2)$—$(CH_2)$— or —$(CH_2)$—O—$(CH_2)$— group;

$R^{20}$ represents an alkyl group selected from the group consisting of methyl, ethyl, n-propyl, isopropyl, n-butyl, sec-butyl, isobutyl and tert-butyl or a benzyl group;

$R^{21}$ represents a cycloaliphatic group selected from the group consisting of cyclopropyl, cyclobutyl, cyclopentyl, cyclohexyl, cycloheptyl, wherein the cycloaliphatic group may in each case be substituted with 1, 2 or 3 substituents mutually independently selected from the group consisting of —C(=O)—OH and —$(CH_2)$—C(=O)—OH, or a group selected from the group consisting of phenyl, naphthyl, (1,3)-benzodioxolyl and (1,4)-benzodioxanyl, wherein the group may in each case be substituted with 1, 2 or 3 substituents mutually independently selected from the group consisting of F, Cl, Br, —O—$CH_3$ and —O—$C_2H_5$;

$R^{22}$ represents a phenyl group;

$R^{23}$ represents a group selected from the group consisting of phenyl, naphthyl, thiophenyl, furanyl and pyridinyl, wherein the group may in each case be substituted with 1, 2 or 3 substituents mutually independently selected from the group consisting of F, Cl, Br, —$CF_3$, —O—$CH_3$, —O—$C_2H_5$, —O—$CH(CH_3)_2$, —O—$CH_2$—$CH_2$—$CH_2$—$CH_3$, —O—$CF_3$, —O—$CHF2$, —O—$CH_2F$, methyl, ethyl, n-propyl, isopropyl, n-butyl, sec-butyl, isobutyl and tert-butyl;

$R^{24}$ and $R^{25}$, mutually independently, in each case represent a methyl or ethyl group;

$R^{26}$ represents hydrogen;

$R^{27}$ represents an alkyl group selected from the group consisting of methyl, ethyl, n-propyl, isopropyl and n-butyl; a cyclohexyl group;

or a phenyl group, which may be substituted with 1, 2, 3, 4 or 5 substituents mutually independently selected from the group consisting of F, Cl, Br, —O—$CH_3$ and —O—$C_2H_5$;

$R^{28}$ represents a phenyl group, which may be substituted with 1, 2, 3, 4 or 5 substituents mutually independently selected from the group consisting of F, Cl, Br, I, —CN, —$CF_3$, —$SF5$, —OH, —O—$CH_3$, —O—$C_2H_5$, —$NH_2$, —$NO_2$, —O—$CF_3$, —O—$CHF_2$, —O—$CH_2F$, —S—$CF_3$, —S—$CHF_2$, —S—$CH_2F$, —SH, —S—$CH_s$, —S—$C_2H_5$, methyl, ethyl, n-propyl, isopropyl, n-butyl, sec-butyl, isobutyl, tert-butyl;

$R^{29}$ represents an alkyl group selected from the group consisting of methyl, ethyl, n-propyl, isopropyl, n-butyl, isobutyl and tert-butyl;

$R^{30}$ represents a phenyl group and $R^{31}$ represents a group selected from the group consisting of phenyl and naphthyl, wherein the group may in each case be substituted with 1, 2 or 3 substituents mutually independently selected from the group consisting of F, Cl and Br;

or a corresponding salt thereof.

7. A compound according to claim 1, wherein said compound is selected from the group consisting of:

[1] 6,7-dihydro-4H-isoxazolo[4,5-c]pyridine-3,5-dicarboxylic acid 3-[(2-methoxy-ethyl) amide] 5-[(3-methoxyphenyl) amide],

[2] 6,7-dihydro-4H-isoxazolo[4,5-c]pyridine-3,5-dicarboxylic acid 3-cyclopentyl amide 5-(4-fluorobenzyl amide),

[3] 6,7-dihydro-4H-isoxazolo[4,5-c]pyridine-3,5-dicarboxylic acid 3-phenyl amide 5-[(4-trifluoromethoxyphenyl) amide],

[4] 6,7-dihydro-4H-isoxazolo[4,5-c]pyridine-3,5-dicarboxylic acid 5-[(4-methyl-3-nitro-phenyl) amide] 3-(phenethyl amide),

[5] 6,7-dihydro-4H-isoxazolo[4,5-c]pyridine-3,5-dicarboxylic acid 3-[(2-methoxy-ethyl) amide] 5-[(4-methyl-3-nitro-phenyl) amide],

[6] 3-{[5-(2,5-difluoro-phenylcarbamoyl)-4,5,6,7-tetrahydro-isoxazolo[4,5-c]pyridine-3-carbonyl]-amino}-propionic acid ethyl ester,

[7] 6,7-dihydro-4H-isoxazolo[4,5-c]pyridine-3,5-dicarboxylic acid 5-[(4-butoxy-phenyl) amide] 3-[(2-methoxy-ethyl) amide],

[8] 6,7-dihydro-4H-isoxazolo[4,5-c]pyridine-3,5-dicarboxylic acid 5-[(3-fluorophenyl) amide] 3-(phenethyl amide),

[9] 6,7-dihydro-4H-isoxazolo[4,5-c]pyridine-3,5-dicarboxylic acid 5-[(4-methyl-3-nitro-phenyl) amide] 3-[(thiophen-2-ylmethyl) amide],

[10] 6,7-dihydro-4H-isoxazolo[4,5-c]pyridine-3,5-dicarboxylic acid 3-benzyl amide 5-(phenethyl amide),

[11] 6,7-dihydro-4H-isoxazolo[4,5-c]pyridine-3,5-dicarboxylic acid 3-[(2-ethylsulfanyl-ethyl) amide] 5-[(3-methoxyphenyl) amide],

[12] 6,7-dihydro-4H-isoxazolo[4,5-c]pyridine-3,5-dicarboxylic acid 5-[(3-cyano-phenyl) amide] 3-[(thiophen-2-ylmethyl) amide],

[13] 6,7-dihydro-4H-isoxazolo[4,5-c]pyridine-3,5-dicarboxylic acid 5-[(4-ethoxy-phenyl) amide] 3-phenyl amide,

[14] 6,7-dihydro-4H-isoxazolo[4,5-c]pyridine-3,5-dicarboxylic acid 3-(4-fluorobenzyl amide) 5-[(4-methyl-3-nitro-phenyl) amide],

[15] 6,7-dihydro-4H-isoxazolo[4,5-c]pyridine-3,5-dicarboxylic acid 5-[(3-acetyl-phenyl) amide] 3-[(5-methyl-furan-2-ylmethyl) amide],

[16] 6,7-dihydro-4H-isoxazolo[4,5-c]pyridine-3,5-dicarboxylic acid 5-[(4-methyl-3-nitro-phenyl) amide] 3-prop-2-ynyl amide,

[17] 6,7-dihydro-4H-isoxazolo[4,5-c]pyridine-3,5-dicarboxylic acid 3-benzyl amide 5-phenyl amide,

[18] 6,7-dihydro-4H-isoxazolo[4,5-c]pyridine-3,5-dicarboxylic acid 5-[(1-naphthalen-1-yl-ethyl) amide] 3-(phenethyl amide),

[19] 6,7-dihydro-4H-isoxazolo[4,5-c]pyridine-3,5-dicarboxylic acid 5-[(3-fluorophenyl) amide] 3-prop-2-ynyl amide,

[20] 3-{[5-(2,5-dimethoxy-phenylcarbamoyl)-4,5,6,7-tetrahydro-isoxazolo[4,5-c]pyridine-3-carbonyl]-amino}-propionic acid ethyl ester,
[21] 6,7-dihydro-4H-isoxazolo[4,5-c]pyridine-3,5-dicarboxylic acid 5-[(4-ethoxy-phenyl) amide] 3-(4-fluorobenzyl amide),
[22] 6,7-dihydro-4H-isoxazolo[4,5-c]pyridine-3,5-dicarboxylic acid 5-[(5-chloro-2-methoxyphenyl) amide] 3-(phenethyl amide),
[23] 3-({3-[(5-methyl-furan-2-ylmethyl)-carbamoyl]-6,7-dihydro-4H-isoxazolo[4,5-c]pyridine-5-carbonyl}-amino)-benzoic acid ethyl ester,
[24] 6,7-dihydro-4H-isoxazolo[4,5-c]pyridine-3,5-dicarboxylic acid 5-[(5-chloro-2-methoxyphenyl) amide] 3-(isobutyl-amide),
[25] [2-oxo-2-(3-prop-2-ynylcarbamoyl-6,7-dihydro-4H-isoxazolo[4,5-c]pyridin-5-yl)-ethoxy]acetic acid,
[26] 3-ethyl-5-[3-(2-methoxy-ethylcarbamoyl)-6,7-dihydro-4H-isoxazolo[4,5-c]pyridin-5-yl]-3-methyl-5-oxo-pentanoic acid,
[27] (1-benzyloxymethyl-2-oxo-2-{3-[(pyridin-3-ylmethyl)-carbamoyl]-6,7-dihydro-4H-isoxazolo[4,5-c]pyridin-5-yl}-ethyl)-carbamic acid tert-butyl ester,
[28] {1-[2-oxo-2-(3-phenylcarbamoyl-6,7-dihydro-4H-isoxazolo[4,5-c]pyridin-5-yl)-ethyl]-cyclopentyl}acetic acid,
[29] 3-ethyl-3-methyl-5-oxo-5-(3-phenylcarbamoyl-6,7-dihydro-4H-isoxazolo[4,5-c]pyridin-5-yl)-pentanoic acid,
[30] (2-oxo-2-{3-[(thiophen-2-ylmethyl)-carbamoyl]-6,7-dihydro-4H-isoxazolo[4,5-c]pyridin-5-yl}-ethoxy) acetic acid,
[31] 3,3-dimethyl-4-{3-[(5-methyl-furan-2-ylmethyl)-carbamoyl]-6,7-dihydro-4H-isoxazolo[4,5-c]pyridin-5-yl}-4-oxo-butanoic acid,
[32] 5-(4-trifluoromethoxy-benzenesulfonyl)-4,5,6,7-tetrahydro-isoxazolo[4,5-c]pyridine-3-carboxylic acid benzyl-phenethyl amide,
[33] 5-benzenesulfonyl-4,5,6,7-tetrahydro-isoxazolo[4,5-c]pyridine-3-carboxylic acid (1-naphthalen-2-ylmethyl-pyrrolidin-3-yl) amide,
[34] [5-(4-fluoro-benzenesulfonyl)-4,5,6,7-tetrahydro-isoxazolo[4,5-c]pyridin-3-yl]-(4-thieno[2,3-d]pyrimidine-4-yl-piperazin-1-yl)-methanone,
[35] 5-(4-fluoro-benzenesulfonyl)-4,5,6,7-tetrahydro-isoxazolo[4,5-c]pyridine-3-carboxylic acid (3-phenyl-propyl) amide,
[36] 5-(3-phenyl-acryloyl)-4,5,6,7-tetrahydro-isoxazolo[4,5-c]pyridine-3-carboxylic acid (2-dimethylamino-ethyl) amide,
[37] 5-(2-phenoxy-acetyl)-4,5,6,7-tetrahydro-isoxazolo[4,5-c]pyridine-3-carboxylic acid (2-dimethylamino-ethyl) amide,
[38] 5-(4-fluoro-benzenesulfonyl)-4,5,6,7-tetrahydro-isoxazolo[4,5-c]pyridine-3-carboxylic acid (1-methyl-3-phenyl-propyl) amide,
[39] 5-(4-fluoro-benzenesulfonyl)-4,5,6,7-tetrahydro-isoxazolo[4,5-c]pyridine-3-carboxylic acid [1-(4-trifluoromethyl(-benzyl)-pyrrolidin-3-yl] amide,
[40] 5-(2,5-dichloro-benzenesulfonyl)-4,5,6,7-tetrahydro-isoxazolo[4,5-c]pyridine-3-carboxylic acid (2-benzyloxy-cyclopentyl) amide,
[41] 5-(5-tert-butyl-2-methyl-2H-pyrazole-3-carbonyl)-4,5,6,7-tetrahydro-isoxazolo[4,5-c]pyridine-3-carboxylic acid (2-dimethylamino-ethyl) amide,
[42] [5-(4-fluoro-benzenesulfonyl)-4,5,6,7-tetrahydro-isoxazolo[4,5-c]pyridin-3-yl]-[4-(4-fluorophenyl)-3,6-dihydro-2H-pyridin-1-yl]-methanone,
[43] 4-{[5-(4-fluoro-benzenesulfonyl)-4,5,6,7-tetrahydro-isoxazolo[4,5-c]pyridine-3-carbonyl]-amino}-piperidine-1-carboxylic acid ethyl ester,
[44] 5-(3-phenyl-acryloyl)-4,5,6,7-tetrahydro-isoxazolo[4,5-c]pyridine-3-carboxylic acid cyclopentyl amide,
[45] 5-(4-acetylamino-benzoyl)-4,5,6,7-tetrahydro-isoxazolo[4,5-c]pyridine-3-carboxylic acid cyclopropylmethyl amide,
[46] 5-(5-methyl-2-phenyl-2H-[1,2,3]triazole-4-carbonyl)-4,5,6,7-tetrahydro-isoxazolo[4,5-c]pyridine-3-carboxylic acid (pyridin-3-ylmethyl) amide,
[47] 5-benzenesulfonyl-4,5,6,7-tetrahydro-isoxazolo[4,5-c]pyridine-3-carboxylic acid 3,4-dimethoxy-benzyl amide,
[48] 2-(3,4-difluoro-phenyl)-1-{4-[5-(4-fluoro-benzenesulfonyl)-4,5,6,7-tetrahydro-isoxazolo[4,5-c]pyridine-3-carbonyl]-piperazin-1-yl}-ethanone,
[49] 3-(morpholine-4-carbonyl)-6,7-dihydro-4H-isoxazolo[4,5-c]pyridine-5-sulfonic acid dimethyl amide,
[50] 5-(furan-2-carbonyl)-4,5,6,7-tetrahydro-isoxazolo[4,5-c]pyridine-3-carboxylic acid (thiophen-2-ylmethyl) amide,
[51] 5-(4,7,7-trimethyl-3-oxo-2-oxa-bicyclo[2.2.1]heptane-1-carbonyl)-4,5,6,7-tetrahydro-isoxazolo[4,5-c]pyridine-3-carboxylic acid (2-pyrrolidin-1-yl-ethyl) amide,
[52] 5-(2,5-dichloro-benzenesulfonyl)-4,5,6,7-tetrahydro-isoxazolo[4,5-c]pyridine-3-carboxylic acid [2-(2-chlorophenyl)-ethyl]amide,
[53] 5-(4-methoxy-benzenesulfonyl)-4,5,6,7-tetrahydro-isoxazolo[4,5-c]pyridine-3-carboxylic acid p-tolyl amide,
[54] 5-(2-phenoxy-acetyl)-4,5,6,7-tetrahydro-isoxazolo[4,5-c]pyridine-3-carboxylic acid 4-fluorobenzyl amide,
[55] 1-{4-[5-(4-methoxy-benzenesulfonyl)-4,5,6,7-tetrahydro-isoxazolo[4,5-c]pyridine-3-carbonyl]-piperazin-1-yl}-ethanone,
[56] 5-(toluene-4-sulfonyl)-4,5,6,7-tetrahydro-isoxazolo[4,5-c]pyridine-3-carboxylic acid 4-sulfamoyl-benzyl amide,
[57] 5-(thiophene-2-sulfonyl)-4,5,6,7-tetrahydro-isoxazolo[4,5-c]pyridine-3-carboxylic acid (2-morpholin-4-yl-ethyl) amide,
[58] 5-(4-methoxy-benzoyl)-4,5,6,7-tetrahydro-isoxazolo[4,5-c]pyridine-3-carboxylic acid (2-dimethylamino-ethyl) amide,
[59] 5-(2,5-dichloro-benzenesulfonyl)-4,5,6,7-tetrahydro-isoxazolo[4,5-c]pyridine-3-carboxylic acid benzyl-phenethyl amide,
[60] 5-dimethylsulfamoyl-4,5,6,7-tetrahydro-isoxazolo[4,5-c]pyridine-3-carboxylic acid (2,6,6-trimethyl-bicyclo[3.1.1]hept-3-yl) amide,
[61] 5-benzenesulfonyl-4,5,6,7-tetrahydro-isoxazolo[4,5-c]pyridine-3-carboxylic acid indan-1-yl amide,
[62] 5-(4-methoxy-benzenesulfonyl)-4,5,6,7-tetrahydro-isoxazolo[4,5-c]pyridine-3-carboxylic acid (3-methoxy-propyl) amide,
[63] 5-(4,5-dichloro-thiophene-2-sulfonyl)-4,5,6,7-tetrahydro-isoxazolo[4,5-c]pyridine-3-carboxylic acid (2-morpholin-4-yl-ethyl) amide,
[64] 5-(2-benzyloxy-acetyl)-4,5,6,7-tetrahydro-isoxazolo[4,5-c]pyridine-3-carboxylic acid (2-pyrrolidin-1-yl-ethyl) amide,

[65] [5-(2,5-dichloro-benzenesulfonyl)-4,5,6,7-tetrahydro-isoxazolo[4,5-c]pyridin-3-yl]-[4-(2,4-dimethyl-phenyl)-piperazin-1-yl]-methanone,

[66] 5-pent-4-enoyl-4,5,6,7-tetrahydro-isoxazolo[4,5-c]pyridine-3-carboxylic acid cyclopropylmethyl amide,

[67] 3-methyl-2-{[5-(3-trifluoromethyl-benzenesulfonyl)-4,5,6,7-tetrahydro-isoxazolo[4,5-c]pyridine-3-carbonyl]-amino}-butanoic acid tert-butyl ester,

[68] 5-(3-trifluoromethyl-benzenesulfonyl)-4,5,6,7-tetrahydro-isoxazolo[4,5-c]pyridine-3-carboxylic acid benzyl-phenethyl amide,

[69] 5-(3-trifluoromethyl-benzenesulfonyl)-4,5,6,7-tetrahydro-isoxazolo[4,5-c]pyridine-3-carboxylic acid 2,4-dichloro-benzyl amide,

[70] 5-dimethylsulfamoyl-4,5,6,7-tetrahydro-isoxazolo[4,5-c]pyridine-3-carboxylic acid (2-cyano-ethyl)-pyridin-3-ylmethyl-amide,

[71] 5-(2-cyclopentyl-acetyl)-4,5,6,7-tetrahydro-isoxazolo[4,5-c]pyridine-3-carboxylic acid (2-pyrrolidin-1-yl-ethyl) amide,

[72] 5-(5-methyl-2-phenyl-2H-[1,2,3]triazole-4-carbonyl)-4,5,6,7-tetrahydro-isoxazolo[4,5-c]pyridine-3-carboxylic acid 4-fluorobenzyl amide,

[73] 5-(3-trifluoromethyl-benzenesulfonyl)-4,5,6,7-tetrahydro-isoxazolo[4,5-c]pyridine-3-carboxylic acid (2-ethyl-hexyl)-amide,

[74] 5-(2,3-difluoro-4-methyl-benzoyl)-4,5,6,7-tetrahydro-isoxazolo[4,5-c]pyridine-3-carboxylic acid (2-dimethylamino-ethyl) amide,

[75] 5-(4-trifluoromethoxy-benzenesulfonyl)-4,5,6,7-tetrahydro-isoxazolo[4,5-c]pyridine-3-carboxylic acid 2,3-dichloro-benzyl amide,

[76] 5-dimethylsulfamoyl-4,5,6,7-tetrahydro-isoxazolo[4,5-c]pyridine-3-carboxylic acid [2-(4-chlorophenyl)-ethyl]amide,

[77] 5-(6-chloro-pyridine-3-carbonyl)-4,5,6,7-tetrahydro-isoxazolo[4,5-c]pyridine-3-carboxylic acid (2-pyrrolidin-1-yl-ethyl) amide,

[78] 5-[3-(4-fluoro-benzylcarbamoyl)-6,7-dihydro-4H-isoxazolo[4,5-c]pyridin-5-yl]-5-oxo-pentanoic acid methyl ester,

[79] 5-[2-(4-methoxyphenyl)-acetyl]-4,5,6,7-tetrahydro-isoxazolo[4,5-c]pyridine-3-carboxylic acid benzyl amide,

[80] 5-(4-trifluoromethoxy-benzenesulfonyl)-4,5,6,7-tetrahydro-isoxazolo[4,5-c]pyridine-3-carboxylic acid [3-(methylphenyl-amino)-propyl] amide,

[81] 5-[2-(4-chlorophenoxy)-acetyl]-4,5,6,7-tetrahydro-isoxazolo[4,5-c]pyridine-3-carboxylic acid cyclopentyl amide,

[82] [4-(2-cyclohexyl-ethyl)-piperazin-1-yl]-[5-(toluene-4-sulfonyl)-4,5,6,7-tetrahydro-isoxazolo[4,5-c]pyridin-3-yl]-methanone,

[83] N-{1-[5-(2,5-dichloro-benzenesulfonyl)-4,5,6,7-tetrahydro-isoxazolo[4,5-c]pyridine-3-carbonyl]-piperidin-4-ylmethyl}-2,2,2-trifluoroacetamide,

[84] 5-(4-methoxy-benzenesulfonyl)-4,5,6,7-tetrahydro-isoxazolo[4,5-c]pyridine-3-carboxylic acid [1-(4-methoxyphenyl)-ethyl] amide,

[85] 2-{[5-(thiophene-2-sulfonyl)-4,5,6,7-tetrahydro-isoxazolo[4,5-c]pyridine-3-carbonyl]-amino}-propionic acid ethyl ester,

[86] 1-(4-{4-[5-(toluene-4-sulfonyl)-4,5,6,7-tetrahydro-isoxazolo[4,5-c]pyridine-3-carbonyl]-piperazin-1-yl}-phenyl)-ethanone,

[87] 5-(3-trifluoromethyl-benzenesulfonyl)-4,5,6,7-tetrahydro-isoxazolo[4,5-c]pyridine-3-carboxylic acid (4-allyloxy-benzyl)-furan-2-ylmethyl amide,

[88] 4-carbamoyl-4-{[5-(4-methoxy-benzenesulfonyl)-4,5,6,7-tetrahydro-isoxazolo[4,5-c]pyridine-3-carbonyl]-amino}-butanoic acid tert-butyl ester,

[89] 5-dimethylsulfamoyl-4,5,6,7-tetrahydro-isoxazolo[4,5-c]pyridine-3-carboxylic acid furan-2-ylmethyl-(4-methylsulfanyl-benzyl) amide,

[90] 5-(4-bromo-3-methyl-benzoyl)-4,5,6,7-tetrahydro-isoxazolo[4,5-c]pyridine-3-carboxylic acid (2-morpholin-4-yl-ethyl) amide,

[91] 5-(toluene-4-sulfonyl)-4,5,6,7-tetrahydro-isoxazolo[4,5-c]pyridine-3-carboxylic acid [1-(2,6-dichloro-benzyl)-pyrrolidin-3-yl] amide,

[92] 5-benzenesulfonyl-4,5,6,7-tetrahydro-isoxazolo[4,5-c]pyridine-3-carboxylic acid [2-(3,4-dichloro-phenyl)-ethyl]amide,

[93] 5-(3-difluoromethylsulfanyl-benzenesulfonyl)-4,5,6,7-tetrahydro-isoxazolo[4,5-c]pyridine-3-carboxylic acid (2-dimethylamino-ethyl) amide,

[94] 5-[2-(3-chlorophenoxy)-acetyl]-4,5,6,7-tetrahydro-isoxazolo[4,5-c]pyridine-3-carboxylic acid (2-pyrrolidin-1-yl-ethyl) amide,

[95] 5-(4-methoxy-benzenesulfonyl)-4,5,6,7-tetrahydro-isoxazolo[4,5-c]pyridine-3-carboxylic acid 2,3-dimethoxy-benzyl amide,

[96] 5-(4-trifluoromethoxy-benzenesulfonyl)-4,5,6,7-tetrahydro-isoxazolo[4,5-c]pyridine-3-carboxylic acid (1-methyl-3-phenyl-propyl) amide,

[97] (5-benzenesulfonyl-4,5,6,7-tetrahydro-isoxazolo[4,5-c]pyridin-3-yl)-[4-(3-phenyl-allyl)-piperazin-1-yl]-methanone,

[98] {[5-(4-methoxy-benzoyl)-4,5,6,7-tetrahydro-isoxazolo[4,5-c]pyridine-3-carbonyl]-amino}-propionic acid ethyl ester,

[99] 5-(4-phenoxy-butyryl)-4,5,6,7-tetrahydro-isoxazolo[4,5-c]pyridine-3-carboxylic acid (2-dimethylamino-ethyl) amide,

[100] 5-(4-trifluoromethoxy-benzenesulfonyl)-4,5,6,7-tetrahydro-isoxazolo[4,5-c]pyridine-3-carboxylic acid [2-(7-methyl-1H-indol-3-yl)-ethyl]amide,

[101] [4-(3-phenyl-allyl)-piperazin-1-yl]-[5-(thiophene-2-sulfonyl)-4,5,6,7-tetrahydro-isoxazolo[4,5-c]pyridin-3-yl]-methanone,

[102] 5-(4-bromo-3-methyl-benzoyl)-4,5,6,7-tetrahydro-isoxazolo[4,5-c]pyridine-3-carboxylic acid (2-pyrrolidin-1-yl-ethyl) amide,

[103] 5-benzenesulfonyl-4,5,6,7-tetrahydro-isoxazolo[4,5-c]pyridine-3-carboxylic acid [1-(4-trifluoromethyl-benzyl)-pyrrolidin-3-yl] amide,

[104] 5-(thiophene-2-sulfonyl)-4,5,6,7-tetrahydro-isoxazolo[4,5-c]pyridine-3-carboxylic acid (2-phenyl-propyl) amide,

[105] 5-(3-chloro-4-fluoro-benzoyl)-4,5,6,7-tetrahydro-isoxazolo[4,5-c]pyridine-3-carboxylic acid phenethyl amide,

[106] 5-benzenesulfonyl-4,5,6,7-tetrahydro-isoxazolo[4,5-c]pyridine-3-carboxylic acid [2-(4-methoxy-phenoxy)-ethyl]amide,

[107] 5-dimethylsulfamoyl-4,5,6,7-tetrahydro-isoxazolo[4,5-c]pyridine-3-carboxylic acid 3-fluoro-4-trifluoromethyl-benzyl amide,

[108] 5-(3-methyl-benzoyl)-4,5,6,7-tetrahydro-isoxazolo[4,5-c]pyridine-3-carboxylic acid prop-2-ynyl amide,

[109] 5-(toluene-4-sulfonyl)-4,5,6,7-tetrahydro-isoxazolo[4,5-c]pyridine-3-carboxylic acid [2-(4-methoxy-phenoxy)-ethyl]amide,
[110] [4-(2-chlorophenyl)-piperazin-1-yl]-[5-(2,5-dichloro-benzenesulfonyl)-4,5,6,7-tetrahydro-isoxazolo[4,5-c]pyridin-3-yl]-methanone,
[111] 3-{[5-(2,6-difluoro-3-methyl-benzoyl)-4,5,6,7-tetrahydro-isoxazolo[4,5-c]pyridine-3-carbonyl]-amino}-propionic acid ethyl ester,
[112] 5-(2,5-dichloro-benzenesulfonyl)-4,5,6,7-tetrahydro-isoxazolo[4,5-c]pyridine-3-carboxylic acid 2,4-difluoro-benzyl amide,
[113] 5-benzenesulfonyl-4,5,6,7-tetrahydro-isoxazolo[4,5-c]pyridine-3-carboxylic acid 3-fluoro-4-trifluoromethyl-benzyl amide,
[114] 5-(4-butoxy-benzenesulfonyl)-4,5,6,7-tetrahydro-isoxazolo[4,5-c]pyridine-3-carboxylic acid isobutyl amide,
[115] 5-(3-fluoro-4-methyl-benzoyl)-4,5,6,7-tetrahydro-isoxazolo[4,5-c]pyridine-3-carboxylic acid (2-pyrrolidin-1-yl-ethyl) amide,
[116] 5-(2-chloro-5-trifluoromethyl-benzoyl)-4,5,6,7-tetrahydro-isoxazolo[4,5-c]pyridine-3-carboxylic acid isobutyl amide,
[117] 5-(4-trifluoromethoxy-benzenesulfonyl)-4,5,6,7-tetrahydro-isoxazolo[4,5-c]pyridine-3-carboxylic acid (1-benzyl-pyrrolidin-3-yl) amide,
[118] 5-(3-chloro-benzenesulfonyl)-4,5,6,7-tetrahydro-isoxazolo[4,5-c]pyridine-3-carboxylic acid (2-pyrrolidin-1-yl-ethyl) amide,
[119] 5-(3-trifluoromethoxy-benzoyl)-4,5,6,7-tetrahydro-isoxazolo[4,5-c]pyridine-3-carboxylic acid (2-dimethylamino-ethyl) amide,
[120] 2-{[5-(toluene-4-sulfonyl)-4,5,6,7-tetrahydro-isoxazolo[4,5-c]pyridine-3-carbonyl]-amino}-propionic acid tert-butyl ester,
[121] 3-{[5-(4-chloro-benzenesulfonyl)-4,5,6,7-tetrahydro-isoxazolo[4,5-c]pyridine-3-carbonyl]-amino}-propionic acid ethyl ester,
[122] 5-dimethylsulfamoyl-4,5,6,7-tetrahydro-isoxazolo[4,5-c]pyridine-3-carboxylic acid [2-(3,4-dichloro-phenyl)-ethyl]amide,
[123] 5-(thiophene-2-sulfonyl)-4,5,6,7-tetrahydro-isoxazolo[4,5-c]pyridine-3-carboxylic acid cyclopropylmethyl amide,
[124] 5-(quinoline-6-carbonyl)-4,5,6,7-tetrahydro-isoxazolo[4,5-c]pyridine-3-carboxylic acid 4-fluorobenzyl amide,
[125] 3-{[5-(2-naphthalen-2-yl-acetyl)-4,5,6,7-tetrahydro-isoxazolo[4,5-c]pyridine-3-carbonyl]-amino}-propionic acid ethyl ester,
[126] [2-(3-isobutylcarbamoyl-6,7-dihydro-4H-isoxazolo[4,5-c]pyridin-5-yl)-2-oxo-1-phenyl-ethyl]-carbamic acid benzyl ester,
[127] 5-(4-methoxy-benzylthiocarbamoyl)-4,5,6,7-tetrahydro-isoxazolo[4,5-c]pyridine-3-carboxylic acid cyclopentyl amide,
[128] 5-benzoylaminocarbothioyl-4,5,6,7-tetrahydro-isoxazolo[4,5-c]pyridine-3-carboxylic acid (2-pyrrolidin-1-yl-ethyl) amide,
[129] 5-(4-chloro-benzylthiocarbamoyl)-4,5,6,7-tetrahydro-isoxazolo[4,5-c]pyridine-3-carboxylic acid cyclopropylmethyl amide,
[130] 5-(2-methoxy-ethylthiocarbamoyl)-4,5,6,7-tetrahydro-isoxazolo[4,5-c]pyridine-3-carboxylic acid phenethyl amide,
[131] 5-pentafluorophenylthiocarbamoyl-4,5,6,7-tetrahydro-isoxazolo[4,5-c]pyridine-3-carboxylic acid phenethyl amide,
[132] 5-(1-phenyl-ethylthiocarbamoyl)-4,5,6,7-tetrahydro-isoxazolo[4,5-c]pyridine-3-carboxylic acid phenethyl amide,
[133] 5-pentafluorophenylthiocarbamoyl-4,5,6,7-tetrahydro-isoxazolo[4,5-c]pyridine-3-carboxylic acid (5-methyl-furan-2-ylmethyl) amide,
[134] 3-{[5-(cyclohexylmethyl-thiocarbamoyl)-4,5,6,7-tetrahydro-isoxazolo[4,5-c]pyridine-3-carbonyl]-amino}-propionic acid ethyl ester,
[135] 5-(1-bromo-naphthalen-2-ylmethyl)-4,5,6,7-tetrahydro-isoxazolo[4,5-c]pyridine-3-carboxylic acid phenyl amide,
[136] $N^5$-(4-methoxyphenyl)-$N^3$-(4-sulfamoylbenzyl)-6,7-dihydroisoxazolo[4,5-c]pyridine-3,5(4H)-dicarboxamide,
[137] 5-(2-(3-chlorophenoxy)acetyl)-N-(2-(pyrrolidin-1-yl)ethyl)-4,5,6,7-tetrahydroisoxazolo[4,5-c]pyridino-3-carboxamide,
[138] 5-(2-fluorobenzoyl)-N-phenyl-4,5,6,7-tetrahydroisoxazolo[4,5-c]pyridine-3-carboxamide,
[139] N-(4-sulfamoylbenzyl)-5-tosyl-4,5,6,7-tetrahydroisoxazolo[4,5-c]pyridine-3-carboxamide,
[140] (5-(3,4-dichlorophenylsulfonyl)-4,5,6,7-tetrahydroisoxazolo[4,5-c]pyridin-3-yl)(4-(thiazol-2-yppiperazin-1-yl)methanone,
[141] (5-(mesitylsulfonyl)-4,5,6,7-tetrahydroisoxazolo[4,5-c]pyridin-3-yl)(4-(thiazol-2-yl)piperazin-1-yl)methanone,
[142] (5-(naphthalen-1-ylsulfonyl)-4,5,6,7-tetrahydroisoxazolo[4,5-c]pyridin-3-yl)(4-(thiazol-2-yl)piperazin-1-yl)methanone,
[143] (5-(naphthalen-2-ylsulfonyl)-4,5,6,7-tetrahydroisoxazolo[4,5-c]pyridin-3-yl)(4-(thiazol-2-yl)piperazin-1-yl)methanone,
[144] (4-(3-(dimethylamino)propyl)piperazin-1-yl)(5-(mesitylsulfonyl)-4,5,6,7-tetrahydroisoxazolo[4,5-c]pyridin-3-yl)methanone dihydrochloride,
[145] (5-(3,4-dichlorophenylsulfonyl)-4,5,6,7-tetrahydroisoxazolo[4,5-c]pyridin-3-yl)(4-(3-(dimethylamino)propyl)piperazin-1-yl)methanone dihydrochloride,
[146] (5-(mesitylsulfonyl)-4,5,6,7-tetrahydroisoxazolo[4,5-c]pyridin-3-yl)(4-(2-(pyrrolidin-1-yl)ethyl)piperidin-1-yl)methanone,
[147] (5-(3,4-dichlorophenylsulfonyl)-4,5,6,7-tetrahydroisoxazolo[4,5-c]pyridin-3-yl)(4-(2-(pyrrolidin-1-yl)ethyl)piperidin-1-yl)methanone,
[148] (5-(naphthalen-2-ylsulfonyl)-4,5,6,7-tetrahydroisoxazolo[4,5-c]pyridin-3-yl)(4-(2-(pyrrolidin-1-yl)ethyl)piperidin-1-yl)methanone,
[149] (5-(naphthalen-1-ylsulfonyl)-4,5,6,7-tetrahydroisoxazolo[4,5-c]pyridin-3-yl)(4-(2-(pyrrolidin-1-yl)ethyl)piperidin-1-yl)methanone hydrochloride,
[150] $N^3$-benzyl-$N^5$-(1-phenylethyl)-6,7-dihydroisoxazolo[4,5-c]pyridine-3,5(4H)-dicarboxamide,
[151] $N^3$-benzyl-$N^5$-(4-methoxyphenyl)-6,7-dihydroisoxazolo[4,5-c]pyridine-3,5(4H)-dicarboxamide,
[152] N-p-tolyl-5-tosyl-4,5,6,7-tetrahydroisoxazolo[4,5-c]pyridine-3-carboxamide,
[153] 5-(3-fluoro-4-(trifluoromethyl)benzoyl)-N-(2-methoxyethyl)-4,5,6,7-tetrahydroisoxazolo[4,5-c]pyridine-3-carboxamide,

[154] N⁵-(4-methoxyphenyl)-N³-(4-sulfamoylbenzyl)-6,7-dihydroisoxazolo[4,5-c]pyridine-3,5(4H)-dicarboxamide,

[155] 5-(2-(3-chlorophenoxy)acetyl)-N-(2-(pyrrolidin-1-yl)ethyl)-4,5,6,7-tetrahydroisoxazolo[4,5-c]pyridine-3-carboxamide,

[156] 5-(2-fluorobenzoyl)-N-phenyl-4,5,6,7-tetrahydroisoxazolo[4,5-c]pyridine-3-carboxamide and

[157] N-(4-sulfamoylbenzyl)-5-tosyl-4,5,6,7-tetrahydroisoxazolo[4,5-c]pyridine-3-carboxamide, or a corresponding salt or solvate thereof.

8. A method for producing a substituted 4,5,6,7-tetrahydroisoxazolo[4,5-c]pyridine compound corresponding to formula I according to claim 1 comprising the steps of:

reacting at least one compound corresponding to formula II,

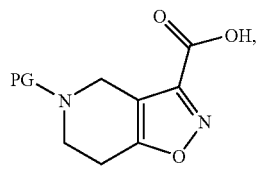

in which PG represents a protective group, in a reaction medium, in the presence of at least one coupling reagent, optionally in the presence of at least one base, with at least one amine of the general formula $HNR^1R^2$, in which the groups $R^1$ and $R^2$ have the meaning according to claim 12, to yield at least one compound corresponding to formula III,

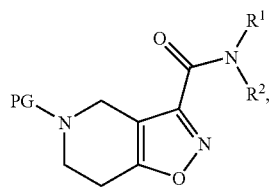

and optionally purifying and/or isolating said compound corresponding to formula III, and reacting said at least one compound corresponding to formula III by elimination in a reaction medium to yield at least one compound corresponding to formula IV, optionally in the form of a corresponding salt,

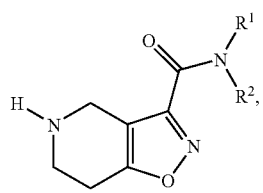

and optionally purifying and/or isolating said compound corresponding to formula IV, and optionally reacting at least one compound corresponding to formula IV in the form of a corresponding salt, in a reaction medium in the presence of at least one base to yield at least one compound corresponding to formula IV, and optionally purifying and/or isolating said compound corresponding to formula IV, and reacting at least one compound corresponding to formula IV in a reaction medium, optionally in the presence of at least one base, with at least one carboxylic acid derivative of the general formula $LG-C(=O)-R^{15}$, $LG-C(=O)-(CH_2)_jX_k-(CH_2)_m-(CH_2)_n-C(=O)-OR^{16}$, $LG-C(=O)-(CHR^{19})-NH-C(=O)-OR^{20}$, $LG-C(=O)-(CH_2)-(CH_2)_p-(CH_2)_q-Y_r-(CH_2)_s-R^{21}$ or $LG-C(=O)-(CH=CH)-R^{22}$, wherein LG represents a leaving group, to yield at least one compound corresponding to formula I, wherein $R^3$ represents $-C(=O)-R^{15}$, $-C(=O)-(CH_2)_j-X_k-(CH_2)_m-(CH_2)_n-C(=O)-OR^{16}$, $-C(=O)-(CHR^{19})-NH-C(=O)-OR^{20}$, $-C(=O)-(CH_2)-(CH_2)_p-(CH_2)_q-Y_r-(CH_2)_s-R^{21}$ or $-C(=O)-(CH=CH)-R^{22}$, and optionally purifying and/or isolating said compound;

or reacting at least one compound corresponding to formula IV in a reaction medium, in the presence of a coupling reagent, optionally in the presence of at least one base, with at least one carboxylic acid of the general formula $HO-C(=O)-R^{15}$, $HO-C(=O)-(CH_2)_jX_k-(CH_2)_m-(CH_2)_n-C(=O)-OR^{16}$, $HO-C(=O)-(CHR^{19})-NH-C(=O)-OR^{20}$, $HO-C(=O)-(CH_2)-(CH_2)_p-(CH_2)_q-Y_r-(CH_2)_s-R^{21}$ or $HO-C(=O)-(CH=CH)-R^{22}$, to yield at least one compound corresponding to formula I, wherein $R^3$ represents $-C(=O)-R^{15}$, $-C(=O)-(CH_2)_jX_k-(CH_2)_n-(CH_2)_n-C(=O)-OR^{16}$, $-C(=O)-(CHR^{19})-NH-C(=O)-OR^{20}$, $-C(=O)-(CH_2)-(CH_2)_p-(CH_2)_q-Y_r-(CH_2)_s-R^{21}$ or $-C(=O)-(CH=CH)-R^{22}$, and optionally purifying and/or isolating said compound;

or reacting at least one compound corresponding to formula IV in a reaction medium, optionally in the presence of at least one base, with at least one sulfonic acid derivative of the general formula $LG-S(=O)_2-R^{23}$ or $LG-S(=O)_2-NR^{24}R^{25}$, wherein LG represents a leaving group, to yield at least one compound corresponding to formula I, wherein $R^3$ represents $-S(=O)_2-R^{23}$ or $-S(=O)_2-NR^{24}R^{25}$, wherein $R^{23}$, $R^{24}$ and $R^{25}$ have the above-stated meaning, and optionally purifying and/or isolating said compound;

or reacting at least one compound corresponding to formula IV in a reaction medium with at least one isocyanate of the general formula $R^{14}-N=C=O$, optionally in the presence of at least one base, to yield at least one compound corresponding to formula I, wherein $R^3$ represents $-C(=O)-NR^{13}R^{14}$, and $R^{13}$ represents hydrogen, and optionally purifying and/or isolating said compound;

or reacting at least one compound corresponding to formula IV in a reaction medium with at least one isothiocyanate of the general formula $S=C=N-(CH_2)_t(CH_2)_u-Z_v-R^{27}$, $S=C=N-(CHR^{28})-R^{29}$ or $S=C=N-C(=O)-R^{30}$, optionally in the presence of at least one base, to yield at least one compound corresponding to formula I, wherein $R^3$ represents $-C(=S)-NR^{26}-(CH_2)_t(CH_2)_u-Z_v-R^{27}$, $-C(=S)-NR^{26}-$ $(CHR^{28})$—$R^{29}$ or —C(=S)—$NR^{26}$—C(=O)—$R^{30}$, and $R^{26}$ represents hydrogen, and optionally purifying and/or isolating said compound;

and optionally reacting at least one compound corresponding to formula I, wherein $R^3$ represents —C(=S)—$NR^{26}$—$(CH_2)_t$—$(CH_2)_u$—$Z_v$—$R^{27}$, —C(=S)—$NR^{26}$—$(CHR^{28})$—$R^{29}$, —C(=S)—$NR^{26}$—C(=O)—$R^{30}$ or —C(=O)—$NR^{13}R^{14}$, and $R^{13}$ and $R^{26}$ represent hydrogen, in a reaction medium, optionally in the presence of at least one base, with at least one compound of the general formula LG-Y or LG-X, wherein Y and X are, independently, a linear or branched, saturated or unsaturated, optionally substituted $C_{1-10}$ aliphatic group and LG represents a leaving group, to yield at least one compound corresponding to formula I, wherein $R^3$ represents —C(=S)—NX—$(CH_2)_t(CH_2)_u$—$Z_v$—$R^{27}$, —C(=S)—NX—$(CHR^{28})$—$R^{29}$, —C(=S)—NX—C(=O)—$R^{30}$ or —C(=O)—$NYR^{14}$, and optionally purifying and/or isolating said compound;

or reacting at least one compound corresponding to formula IV in a reaction medium, optionally in the presence of at least one base, with at least one compound of the general formula LG-$(CH_2)$—$R^{31}$, wherein LG represents a leaving group, to yield at least one compound corresponding to formula I, wherein $R^3$ represents —$(CH_2)$—$R^{31}$, and optionally purifying and/or isolating said compound;

or reacting at least one compound corresponding to formula IV in a reaction medium, in the presence of at least one reducing agent, with at least one compound of the general formula $R^{31}$—C(=O)—H, to yield at least one compound corresponding to formula I, wherein $R^3$ represents —$(CH_2)$—$R^{31}$, and optionally purifying and/or isolating said compound.

9. The method of claim 8, wherein PG represents a tert-butyloxy-carbonyl or benzyloxycarbonyl group.

10. The method of claim 8, wherein said at least one base is selected from the group consisting of pyridine, N-methylmorpholine, diisopropylethylamine, triethylamine and 4,4-dimethylaminopyridine.

11. The method of claim 8, wherein said reaction medium for reacting said at least one compound corresponding to formula III by elimination includes at least one acid or at least one base for the tert-butyloxy-carbonyl group or includes hydrogen and a catalyst for the benzyloxycarbonyl group to yield at least one compound corresponding to formula IV, optionally in the form of a corresponding salt.

12. The method of claim 10, wherein said catalyst is palladium on carbon.

13. The method of claim 11, wherein said salt is a hydrochloride salt.

14. The method of claim 8, comprising reacting at least one compound corresponding to formula IV in the form of a corresponding salt, in a reaction medium in the presence of at least one base, said reaction medium including at least one metal hydroxide to yield at least one compound corresponding to formula IV.

15. The method of claim 14, wherein said at least one metal hydroxide includes potassium hydroxide and/or sodium hydroxide.

16. The method of claim 8, wherein said step of reacting at least one compound corresponding to formula IV in a reaction medium is performed in the presence of at least one base selected from the group consisting of pyridine, triethylamine, 4,4-dimethylaminopyridine, diisopropylethylamine and diisopropylamine.

17. The method of claim 8, wherein said step of reacting at least one compound corresponding to formula IV in a reaction medium is performed in the presence of at least one base selected from the group consisting of triethylamine, 4,4-dimethylaminopyridine and diisopropylethylamine.

18. The method of claim 8, wherein said leaving group is a halogen atom or a chlorine atom.

19. The method of claim 8, wherein said step of reacting at least one compound corresponding to formula I, wherein $R^3$ represents —C(=S)—$NR^{26}$—$(CH_2)_t(CH_2)_u$—$Z_v$—$R^{27}$, —C(=S)—$NR^{26}$—$(CHR^{28})$—$R^{29}$, —C(=S)—$NR^{26}$—C(=O)—$R^{30}$ or —C(=O)—$NR^{13}R^{14}$, and $R^{13}$ and $R^{26}$ represent hydrogen, in a reaction medium, is performed in the presence of at least one metal hydride salt.

20. The method of claim 19, wherein said at least one metal hydride salt includes sodium hydride and/or potassium hydride.

21. The method of claim 8, where said step of reacting at least one compound corresponding to formula IV in a reaction medium, optionally in the presence of at least one base, is performed in the presence of at least one metal hydride salt.

22. The method of claim 21, wherein said at least one metal hydride salt includes sodium hydride and/or potassium hydride.

23. A pharmaceutical formulation comprising at least one compound according to claim 1 and one or more physiologically acceptable auxiliary substances.

24. A method of alleviating pain, said method comprising administering to a patient in need thereof an effective pain alleviating amount of a compound according to claim 1.

* * * * *